(12) United States Patent
Singh et al.

(10) Patent No.: US 7,935,693 B2
(45) Date of Patent: *May 3, 2011

(54) POLYCYCLIC ARYL SUBSTITUTED TRIAZOLES AND POLYCYCLIC HETEROARYL SUBSTITUTED TRIAZOLES USEFUL AS AXL INHIBITORS

(75) Inventors: Rajinder Singh, Belmont, CA (US); Dane Goff, Redwood City, CA (US); Jiaxin Yu, San Carlos, CA (US); Sacha Holland, San Francisco, CA (US); Jing Zhang, Foster City, CA (US); Thilo J. Heckrodt, San Francisco, CA (US); Pingyu Ding, Foster City, CA (US); Joane Litvak, Oakland, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 309 days.

This patent is subject to a terminal disclaimer.

(21) Appl. No.: 11/967,163

(22) Filed: Dec. 29, 2007

(65) Prior Publication Data

US 2009/0111816 A1     Apr. 30, 2009

Related U.S. Application Data

(60) Provisional application No. 60/983,107, filed on Oct. 26, 2007.

(51) Int. Cl.
| | |
|---|---|
| *A61K 31/4196* | (2006.01) |
| *A61K 31/496* | (2006.01) |
| *A61K 31/55* | (2006.01) |
| *A61P 35/00* | (2006.01) |
| *A61P 35/02* | (2006.01) |
| *A61K 31/397* | (2006.01) |
| *C07D 249/14* | (2006.01) |
| *C07D 239/70* | (2006.01) |
| *C07D 403/14* | (2006.01) |

(52) U.S. Cl. ......... 514/210.21; 514/252.16; 514/217.06; 514/383; 544/253; 548/265.2; 548/266.2; 548/266.4

(58) Field of Classification Search ............... 514/383; 544/253; 548/265.2, 266.2, 266.4
See application file for complete search history.

(56) References Cited

U.S. PATENT DOCUMENTS

| | | | | |
|---|---|---|---|---|
| 3,813,400 | A | 5/1974 | Boyle et al. | 260/295 |
| 7,279,469 | B2* | 10/2007 | Pierce et al. | 514/217.09 |
| 2004/0077699 | A1 | 4/2004 | Lin et al. | 514/383 |
| 2004/0214817 | A1 | 10/2004 | Pierce et al. | 514/217.09 |
| 2005/0118604 | A1 | 6/2005 | Lorens et al. | 435/6 |
| 2006/0293256 | A1 | 12/2006 | Yamada et al. | 514/27 |
| 2007/0213375 | A1 | 9/2007 | Singh et al. | 514/341 |
| 2008/0176847 | A1* | 7/2008 | Goff et al. | 514/234.5 |
| 2008/0182862 | A1* | 7/2008 | Ding et al. | 514/260.1 |
| 2008/0188454 | A1* | 8/2008 | Goff et al. | 514/210.21 |
| 2008/0188455 | A1* | 8/2008 | Goff et al. | 514/211.11 |
| 2008/0188474 | A1* | 8/2008 | Goff et al. | 514/236.2 |

FOREIGN PATENT DOCUMENTS

| | | |
|---|---|---|
| EP | 0 710 654 A1 | 5/1996 |
| WO | WO 01/09106 A1 | 2/2001 |
| WO | WO 02/057240 A1 | 7/2002 |
| WO | WO 03/027275 A1 | 4/2003 |
| WO | WO 03/093344 A1 | 11/2003 |
| WO | WO 2004/017997 A1 | 3/2004 |
| WO | WO 2004/039955 A2 | 5/2004 |
| WO | WO 2004/046120 A2 | 6/2004 |
| WO | WO 2004046120 A2 * | 6/2004 |
| WO | WO 2005/013982 A1 | 2/2005 |
| WO | WO 2005/077922 A2 | 8/2005 |
| WO | WO 2006/020767 A2 | 2/2006 |
| WO | WO 2006/034116 A1 | 3/2006 |
| WO | WO 2007/030680 A2 | 3/2007 |
| WO | WO 2008/157131 A1 | 12/2008 |

OTHER PUBLICATIONS

STN_11967163_01202010.*
STN_11967163A_07152010.*
Agrafiotis et al., "SAR Maps: A New SAR Visualization Technique for Medicinal Chemists," *J. Med. Chem.* 50(24): 5926-5937, 2007.
Alexander et al., "Human Parathyroid Hormone 1-34 Reverses Bone Loss in Ovariectomized Mice," *Journal of Bone and Mineral Research* 16(9): 1665-1673, 2001.
Angelillo-Scherrer et al., "Role of Gas6 receptors in platelet signaling during thrombus stabilization and implications for antithrombotic therapy," *Journal of Clinical Investigation* 115(2): 237-246, Feb. 2005.
Bora et al., "Immunotherapy for choroidal neovascularization in a laser-induced mouse model simulating exudative (wet) macular degeneration," *Proc. Natl. Acad. Sci U.S.A.* 100(5): 2679-2684, Mar. 4, 2003.
Brewster et al., "Ro 32/3555, an orally active collagenase selective inhibitor, prevents structural damage in the STR/ORT mouse model of osteoarthritis," *Arthritis & Rheumatism* 41(9): 1639-1644, Sep. 1998.
Fujioka et al., "Equol, a Metabolite of Daidzein, Inhibits Bone Loss in Ovariectomized Mice," *Journal of Nutrition* 134: 2623-2627, 2004.
Holland et al., "Multiple Roles for the Receptor Tyrosine Kinase Axl in Tumor Formation," *Cancer Res.* 65(20): 9294-9303, Oct. 15, 2005.
Holland et al., "Requirement for the Receptor Tyrosine Kinase Axl in Angiogenesis and Tumor Growth", 7th Annual Symposium on Anti-Angiogenic Agents, Feb. 10-13, 2005, San Diego, California, 1 page.
Kadoya et al., "Role of calpain in hydrogen peroxide induced cataract," *Current Eye Research* 12(4): 341-346, 1993.

(Continued)

*Primary Examiner* — Yong Chu
(74) *Attorney, Agent, or Firm* — Seed IP Law Group PLLC

(57) ABSTRACT

Polycyclic aryl and polycyclic heteroaryl substituted triazoles and pharmaceutical compositions containing the compounds are disclosed as being useful in inhibiting the activity of the receptor protein tyrosine kinase Axl. Methods of using the compounds in treating diseases or conditions associated with Axl catalytic activity are also disclosed.

63 Claims, No Drawings

OTHER PUBLICATIONS

Katritzky et al., "Syntheses of 5-(2-arylazenyl)-1,2,4-triazoles and 2-amino-5-aryl-1,3,4-oxadiazoles," *ARKIVOC* 6: 82-90, 2002.

Kim et al., "Novel Oral Formulation of Paclitaxel Inhibits Neointimal Hyperplasia in a Rat Carotid Artery Injury Model," *Circulation* 109: 1558-1563, Mar. 8, 2004.

Kurzer and Douraghi-Zadeh, "Heterocyclic Compounds from Urea Derivatives. Part VI. Synthesis and Cyclisation of 1-Amino-3-(NN'-diarylamidino)guanidines and Some Analogues," *J. Chem. Soc.* 932-937, 1965.

Lebovic et al., "Peroxisome proliferator-activated receptor-gamma induces regression of endometrial explants in a rat model of endometriosis," *Fertility and Sterility* 82(Suppl 3): 1008-1013, Oct. 2004.

Nakashima et al., "ApoE-Deficient Mice Develop Lesions of All Phases of Atherosclerosis Throughout the Arterial Tree," *Arterioscler. Thromb. Vasc. Biol.* 14(1): 133-140, Jan. 1994.

Nickoloff et al., "Severe Combined Immunodeficiency Mouse and Human Psoriatic Skin Chimeras. Validation of a New Animal Model," *American Journal of Pathology* 146(3): 580-588, Mar. 1995.

Phadke et al., "Evaluation of the Effects of Various Anti-Arthritic Drugs on Type II Collagen-Induced Mouse Arthritis Model," *Immunopharmacology* 10: 51-60, 1985.

Reiter and Pongó, "On Triazoles. VI [1]. The Acylation of 5-Amino-1,2,4-triazoles," *J. Heterocyclic Chem.* 24: 127-142, Jan.-Feb. 1987.

Sarayba et al., "Inhibition of corneal neovascularization by a peroxisome proliferator-activated receptor-γ ligand," *Experimental Eye Research* 80: 435-442, 2005.

Sheets et al., "Cataract- and Lens-Specific Upregulation of ARK Receptor Tyrosine Kinase in Emory Mouse Cataract," *Investigative Ophthalmology & Visual Science* 43(6): 1870-1875, Jun. 2002.

Smith et al., "Oxygen-Induced Retinopathy in the Mouse," *Investigative Ophthalmology & Visual Science* 35(1): 101-111, Jan. 1994.

Somigliana et al., "Endometrial ability to implant in ectopic sites can be prevented by interleukin-12 in a murine model of endometriosis," *Human Reproduction* 14(12): 2944-2950, 1999.

Von Der Thüsen et al., "Adenoviral Transfer of Endothelial Nitric Oxide Synthase Attenuates Lesion Formation in a Novel Murine Model of Postangioplasty Restenosis," *Arterioscler. Thromb. Vasc. Biol.* 24: 357-362, Feb. 2004.

Wronski et al., "Endocrine and Pharmacological Suppressors of Bone Turnover Protect against Osteopenia in Ovariectomized Rats," *Endocrinology* 125(2): 810-816, 1989.

Xu et al., "Requirement for the tyrosine kinase Axl in angiogenesis and tumor growth," *Proc. Amer. Assoc. Cancer Res.* 46, 2005. Tumor Biology 14: Signaling and Angiogenesis; Abstract #2019 of observations disclosed at American Association Cancer Research General Meeting, Apr. 16-20, 2005, Anaheim, California, 1 page.

Yin et al., "Expression of growth arrest-specific gene 6 and its receptors in a rat model of chronic renal transplant rejection," *Transplantation* 73(4): 657-660, Feb. 27, 2002.

Modest et al., "2,4-Diaminopyrimidines from Dicyandiamide. III. Reaction with Monocyclic Ketones," *J. Org. Chem.* 30(6): 1837-1840, Jun. 1965.

Sigma-Aldrich Co. Catalog entitled "Aldrich Advancing Science," pp. 739, 752 and 761, 2005.

* cited by examiner

US 7,935,693 B2

POLYCYCLIC ARYL SUBSTITUTED TRIAZOLES AND POLYCYCLIC HETEROARYL SUBSTITUTED TRIAZOLES USEFUL AS AXL INHIBITORS

CROSS-REFERENCE TO RELATED APPLICATION

This application claims the benefit under 35 U.S.C. §119(e) of U.S. Provisional Patent Application No. 60/983,107, filed Oct. 26, 2007, where this provisional application is incorporated herein by reference in its entirety.

FIELD OF THE INVENTION

This invention is directed to polycyclic aryl substituted triazoles and polycyclic heteroaryl substituted triazoles and pharmaceutical compositions thereof which are useful as inhibitors of the receptor protein tyrosine kinase known as Axl. This invention is also directed to methods of using the compounds and compositions in treating diseases and conditions associated with Axl activity, particularly in treating diseases and conditions associated with angiogenesis and/or cell proliferation.

BACKGROUND OF THE INVENTION

All of the protein kinases that have been identified to date in the human genome share a highly conserved catalytic domain of around 300 aa. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (EC's) and vascular smooth muscle cells (VSMC's) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl–/– mice exhibit no overt developmental phenotype and the physiological function of Axl in vivo is not clearly established in the literature.

Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemia's. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl—Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoporosis, osteoarthritis and cataracts.

SUMMARY OF THE INVENTION

This invention is directed to certain polycyclic aryl substituted triazoles and polycyclic heteroaryl substituted triazoles which are useful as Axl inhibitors, methods of using such compounds in treating diseases and conditions associated with Axl activity and pharmaceutical compositions comprising such compounds.

Accordingly, in one aspect this invention is directed to compounds of formula (I):

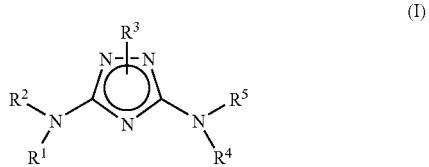

wherein:
R¹, R⁴ and R⁵ are independently selected from hydrogen, alkyl, aryl, aralkyl, —C(O)R⁹ or —C(O)N(R⁶)R⁷;
one of R² and R³ is selected from one of the following and the other is selected from the other two of the following:
a) a bicyclic aryl of formula (II) or a bicyclic heteroaryl of formula (II):

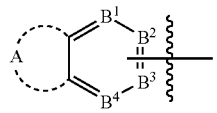

(II)

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by —NR⁹—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R⁶, —R¹⁰—OR⁹, —R¹⁰—O—R¹¹—OR⁹, —R¹⁰—O—R¹¹—O—R¹¹—OR⁹, —R¹⁰—O—R¹¹—CN, —R¹⁰—O—R¹¹—C(O)OR⁹, —R¹⁰—O—R¹¹—C(O)N(R⁶)R⁷, —R¹⁰—O—R¹¹—S(O)$_p$R⁹ (where p is 0, 1 or 2), —R¹⁰—O—R¹¹—N(R⁶)R⁷, —R¹⁰—O—R¹¹—C(NR¹²)N(R¹²)H, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁸, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2); and
B¹, B², B³ and B⁴ are each independently selected from the group consisting of =C(R¹³)— and =N—, provided that one of B¹, B², B³ and B⁴ is a carbon directly bonded to the nitrogen to which its corresponding R² or R³ is attached;
b) a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R¹⁰—OR⁹, —R¹⁰—O—R¹¹—OR⁹, —R¹⁰—O—R¹¹—O—R¹¹—OR⁹, —R¹⁰—O—R¹¹—CN, —R¹⁰—O—R¹¹—C(O)OR⁹, —R¹⁰—O—R¹¹—C(O)N(R⁶)R⁷, —R¹⁰—O—R¹¹—S(O)$_p$R⁹ (where p is 0, 1 or 2), —R¹⁰—O—R¹¹—N(R⁶)R⁷, —R¹⁰—O—R¹¹—C(NR¹²)N(R¹²)H, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁹, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2); or c) a bridged bicyclic aryl of formula (III) or a bridged bicyclic heteroaryl of formula (III):

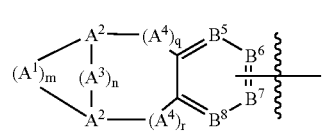

(III)

where:
m and n are independently 1 to 4;
q and r are independently 0 to 3;
each A¹, A³ and A⁴ is independently selected from the group consisting of C(R⁸)₂, O, S(O)$_p$ (where p is 0, 1 or 2), P(O)$_p$ (where p is 0, 1 or 2) and N(R⁹);
each A² is independently selected from the group consisting of C(R⁸) and N;
B⁵, B⁶, B⁷ and B⁸ are each independently selected from the group consisting of =C(R¹³)— and =N—, provided that one of B⁵, B⁶, B⁷ and B⁸ is a carbon directly bonded to the nitrogen to which its corresponding R² or R³ is attached;
each R⁶ and R⁷ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R¹¹—OR⁹, —R¹¹—CN, —R¹¹—NO₂, —R¹¹—N(R⁹)₂, —R¹¹—C(O)OR⁹ and —R¹¹—C(O)N(R⁹)₂, or any R⁶ and R⁷, together with the common nitrogen to which they are both attached, form an optionally substituted N-heteroaryl or an optionally substituted N-heterocyclyl;
each R⁸ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, —R¹⁰—OR⁹, —R¹⁰—O—R¹¹—OR⁹, —R¹⁰—O—R¹¹—O—R¹¹—OR⁹, —R¹⁰—O—R¹¹—CN, —R¹⁰—O—R¹¹—C(O)OR⁹, —R¹⁰—O—R¹¹—C(O)N(R⁶)R⁷, —R¹⁰—O—R¹¹—S(O)$_p$R⁹ (where p is 0, 1 or 2), —R¹⁰—O—R¹¹—N(R⁶)R⁷, —R¹⁰—O—R¹¹—C(NR¹²)N(R¹²)H, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁹, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2), or two R⁸'s on adjacent carbons can combine to form a double bond;
each R⁹ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl;

each $R^{10}$ is independently selected from the group consisting of a direct bond, an optionally substituted straight or branched alkylene chain, an optionally substituted straight or branched alkenylene chain and an optionally substituted straight or branched alkynylene chain;

each $R^{11}$ is independently selected from the group consisting of an optionally substituted straight or branched alkylene chain, an optionally substituted straight or branched alkenylene chain and an optionally substituted straight or branched alkynylene chain;

each $R^{12}$ is hydrogen, alkyl, cyano, nitro or —$OR^9$; and each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2);

as an isolated stereoisomer or a mixture thereof, or as a pharmaceutically acceptable salt thereof.

In another aspect, this invention is directed to pharmaceutical compositions comprising a pharmaceutically acceptable excipient and a compound of formula (I), as described above, as an isolated stereoisomer or mixture thereof, or a pharmaceutically acceptable salt thereof.

In another aspect, this invention is directed to methods of treating a disease or condition associated with Axl activity in a mammal, wherein the methods comprise administering to the mammal a therapeutically effective amount of a compound of formula (I), as described above, as an isolated stereoisomer or mixture thereof, or a pharmaceutically acceptable salt thereof, or a therapeutically effective amount of a pharmaceutical composition comprising a pharmaceutical acceptable excipient and a compound of formula (I), as described above, as an isolated stereoisomer or mixture thereof, or a pharmaceutically acceptable salt thereof.

In another aspect, this invention provides assays to determine a compound of the invention effectiveness in inhibiting Axl activity in a cell-based assay.

DETAILED DESCRIPTION OF THE INVENTION

Definitions

As used in the specification and appended claims, unless specified to the contrary, the following terms have the meaning indicated:

"Amino" refers to the —$NH_2$ radical.
"Carboxy" refers to the —C(O)OH radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms ("lower alkyl"), and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl radical may be optionally substituted by one or more of the following substituents: halo, cyano, nitro, oxo, thioxo, trimethylsilanyl, —$OR^{20}$, —OC(O)—$R^{20}$, —N($R^{20}$)$_2$, —C(O)$R^{20}$, —C(O)$OR^{20}$, —C(O)N($R^{20}$)$_2$, —N($R^{20}$)C(O)$OR^{20}$, —N($R^{20}$)C(O)$R^{20}$, —N($R^{20}$)S(O)$_t$$R^{20}$ (where t is 1 or 2), —S(O)$_t$$OR^{20}$ (where t is 1 or 2), —S(O)$_p$$R^{20}$ (where p is 0, 1 or 2), and —S(O)$_t$N($R^{20}$)$_2$ (where t is 1 or 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl radical may be optionally substituted by one or more of the following substituents: halo, cyano, nitro, oxo, thioxo, trimethylsilanyl, —$OR^{20}$, —OC(O)—$R^{20}$, —N($R^{20}$)$_2$, —C(O)$R^{20}$, —C(O)$OR^{20}$, —C(O)N($R^{20}$)$_2$, —N($R^{20}$)C(O)$OR^{20}$, —N($R^{20}$)C(O)$R^{20}$, —N($R^{20}$)S(O)$_t$$R^{20}$ (where t is 1 or 2), —S(O)$_t$$OR^{20}$ (where t is 1 or 2), —S(O)$_p$$R^{20}$ (where p is 0, 1 or 2), and —S(O)$_t$N($R^{20}$)$_2$ (where t is 1 or 2) where each $R^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkynyl" refers to a straight or branched hydrocarbon chain radical consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, hexynyl, and the like. Unless stated otherwise specifically in the specification, an alkynyl radical may be optionally substituted by one or more of the following substituents: halo, cyano, nitro, oxo, thioxo, trimethylsilanyl, —$OR^{20}$, —OC(O)—$R^{20}$, —N($R^{20}$)$_2$, —C(O)$R^{20}$, —C(O)$OR^{20}$—C(O)N($R^{20}$)$_2$, —N($R^{20}$)C(O)$OR^{20}$, —N($R^{20}$)C(O)$R^{20}$, —N($R^{20}$)S(O)$_t$$R^{20}$ (where t is 1 or 2), —S(O)$_t$$OR^{20}$ (where t is 1 or 2), —S(O)$_p$$R^{20}$ (where p is 0, 1 or 2), and —S(O)$_t$N($R^{20}$)$_2$ (where t is 1 or 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one or more of the following substituents: halo, cyano, nitro, aryl, cycloalkyl, heterocyclyl, heteroaryl, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one or more of the following substituents: halo, cyano, nitro, aryl, cycloalkyl, heterocyclyl, heteroaryl, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one or more of the following substituents: alkyl, alkenyl, halo, haloalkenyl, cyano, nitro, aryl, cycloalkyl, heterocyclyl, heteroaryl, oxo, thioxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{20}$, —N(R$^{20}$)C(O)R$^{20}$, —N(R$^{20}$)S(O)$_t$R$^{20}$ (where t is 1 or 2), —S(O)$_t$OR$^{20}$ (where t is 1 or 2), —S(O)$_p$R$^{20}$ (where p is 0, 1 or 2), and —S(O)$_t$N(R$^{20}$)$_2$ (where t is 1 or 2) where each R$^{20}$ is independently hydrogen, alkyl, haloalkyl, cycloalkyl, cycloalkylalkyl, aryl, aralkyl, heterocyclyl, heterocylylalkyl, heteroaryl or heteroarylalkyl.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —R$_b$—O—R$_a$ where R$_a$ is an alkyl radical as defined above and R$_b$ is an alkylene chain as defined above. The oxygen atom may be bonded to any carbon in the alkyl radical or the alkylene chain. The alkyl part of the alkoxyalkyl radical may be optionally substituted as defined above for an alkyl radical and the alkylene chain part of the alkoxyalkyl radical may be optionally substituted as defined above for an alkylene chain.

"Aryl" refers to a hydrocarbon ring system radical comprising hydrogen, 6 to 14 carbon atoms and at least one aromatic ring. For purposes of this invention, the aryl radical may be a monocyclic, bicyclic, or tricyclic system and which may include spiro ring systems. An aryl radical is commonly, but not necessarily, attached to the parent molecule via an aromatic ring of the aryl radical. Except for bicyclic aryls of formula (II) and bridged bicyclic aryls of formula (III), as described above in the Summary of the Invention, an "aryl" radical as defined herein can not contain rings having more than 7 members and cannot contain rings wherein two non-adjacent members thereof are connected through an atom or a group of atoms (i.e., a bridged ring system). Aryl radicals include, but are not limited to, aryl radicals derived from acenaphthylene, anthracene, azulene, benzene, 6,7,8,9-tetrahydro-5H-benzo[7]annulene, fluorene, as-indacene, s-indacene, indane, indene, naphthalene, phenalene, and phenanthrene. Unless stated otherwise specifically in the specification, the term "optionally substituted aryl" is meant to include aryl radicals optionally substituted by one or more substituents independently selected from the group consisting of alkyl, alkenyl, alkynyl, halo, haloalkyl, haloalkenyl, haloalkynyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocylylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—O—R$^{22}$—C(O)N(R$^{20}$)$_2$, —R$^{21}$—N(R$^{20}$)C(O)OR$^{20}$, —R$^{21}$—N(R$^{20}$)C(O)R$^{20}$, —R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N(R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, may optionally form an optionally substituted N-heterocyclyl or an optionally substituted N-heteroaryl, each R$^{21}$ is independently a direct bond or a straight or branched alkylene or alkenylene chain, and R$^{22}$ is a straight or branched alkylene or alkenylene chain.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl.

"Aralkenyl" refers to a radical of the formula —R$_d$—R$_c$ where R$_d$ is an alkenylene chain as defined above and R$_c$ is one or more aryl radicals as defined above. The aryl part of the aralkenyl radical may be optionally substituted as described above for an aryl. The alkenylene chain part of the aralkenyl radical may be optionally substituted as defined above for an alkenylene group.

"Aralkynyl" refers to a radical of the formula —$R_eR_c$ where $R_e$ is an alkynylene chain as defined above and $R_c$ is one or more aryl radicals as defined above. The aryl part of the aralkynyl radical may be optionally substituted as described above for an aryl. The alkynylene chain part of the aralkynyl radical may be optionally substituted as defined above for an alkynylene chain.

"Aryloxy" refers to a radical of the formula —$OR_c$ where $R_c$ is an aryl as defined above. The aryl part of the aryloxy radical may be optionally substituted as defined above.

"Aralkyloxy" refers to a radical of the formula —$OR_f$ where $R_f$ is an aralkyl radical as defined above. The aralkyl part of the aralkyloxy radical may be optionally substituted as defined above.

"Cycloalkyl" refers to a stable non-aromatic monocyclic or polycyclic hydrocarbon radical consisting solely of carbon and hydrogen atoms, which may include spiro or bridged ring systems, having from three to fifteen carbon atoms, preferably having from three to ten carbon atoms, more preferably from five to seven carbons and which is saturated or unsaturated and attached to the rest of the molecule by a single bond. For purposes of this invention, a bridged ring system is a system wherein two non-adjacent ring atoms thereof are connected through an atom or a group of atoms. Monocyclic cycloalkyl radicals include non-bridged cycloalkyl radicals, for example, cyclopropyl, cyclobutyl, cyclopentyl, cyclohexyl, cycloheptyl, and cyclooctyl. Polycyclic radicals include fused, spiro or bridged cycloalkyl radicals, for example, $C_{10}$ radicals such as adamantanyl (bridged) and decalinyl (fused), and $C_7$ radicals such as bicyclo[3.2.0]heptanyl (fused), norbornanyl and norbornenyl (bridged), as well as substituted polycyclic radicals, for example, substituted $C_7$ radicals such as 7,7-dimethylbicyclo[2.2.1]heptanyl (bridged), and the like. Unless otherwise stated specifically in the specification, the term "optionally substituted cycloalkyl" is meant to include cycloalkyl radicals which are optionally substituted by one or more substituents independently selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{20}$, —$R^{21}$—$N(R^{20})C(O)R^{20}$, —$R^{21}$—$N(R^{20})S(O)_tR^{20}$ (where t is 1 or 2), —$R^{21}$—$S(O)_tOR^{20}$ (where t is 1 or 2), —$R^{21}$—$S(O)_pR^{20}$ (where p is 0, 1 or 2), and —$R^{21}$—$S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"Cycloalkylalkyl" refers to a radical of the formula —$R_bR_g$ where $R_b$ is an alkylene chain as defined above and $R_g$ is a cycloalkyl radical as defined above. The alkylene chain and the cycloalkyl radical may be optionally substituted as defined above.

"Cycloalkylalkenyl" refers to a radical of the formula —$R_dR_g$ where $R_d$ is an alkenylene chain as defined above and $R_g$ is a cycloalkyl radical as defined above. The alkenylene chain and the cycloalkyl radical may be optionally substituted as defined above.

"Cycloalkylalkynyl" refers to a radical of the formula —$R_eR_g$ where $R_e$ is an alkynylene radical as defined above and $R_g$ is a cycloalkyl radical as defined above. The alkynylene chain and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl radical.

"Haloalkoxy" refers to an alkoxy radical, as defined above, that is substituted by one or more halo radicals, as defined above, for example, trifluoromethoxy, difluoromethoxy, trichloromethoxy, 2,2,2-trifluoroethoxy, and the like. The alkoxy part of the haloalkoxy radical may be optionally substituted as defined above for an alkoxy radical.

"Haloalkenyl" refers to an alkenyl radical, as defined above, that is substituted by one or more halo radicals, as defined above. The alkenyl part of the haloalkyl radical may be optionally substituted as defined above for an alkenyl radical.

"Haloalkynyl" refers to an alkynyl radical, as defined above, that is substituted by one or more halo radicals, as defined above. The alkynyl part of the haloalkyl radical may be optionally substituted as defined above for an alkynyl radical.

"Heterocyclyl" refers to a stable 3- to 18-membered non-aromatic ring radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-c]pyridinyl, octahydro-1H-pyrrolo[2,3-b]pyridinyl, octahydro-1H-pyrrolo[3,4-b]pyridinyl, octahydropyrrolo[3,4-c]pyrrolyl, octahydro-1H-pyrido[1,2-a]pyrazinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuranyl, thienyl[1,3] dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a]azepinyl, azepanyl, azabicyclo[3.2.1]octyl, and 2,7-diazaspiro[4.4]nonanyl. Unless stated otherwise specifically in the specification, the term "optionally substituted heterocyclyl" is meant to include heterocyclyl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{20}$, —$R^{21}$—$N(R^{20})C(O)R^{20}$, —$R^{21}$—$N(R^{20})S(O)_tR^{20}$ (where t is 1 or 2), —$R^{21}$—$S(O)_tOR^{20}$ (where t is 1 or 2), —$R^{21}$—$S(O)_pR^{20}$ (where p is 0, 1 or 2), and —$R^{21}$—$S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkylene chain. The heterocyclyl part of the heterocyclylalkyl radical may be optionally substituted as defined above for a heterocyclyl radical.

"Heterocyclylalkenyl" refers to a radical of the formula —$R_dR_h$ where $R_d$ is an alkenylene chain as defined above and $R_h$ is a heterocyclyl radical as defined above, and if the heterocyclyl is a nitrogen-containing heterocyclyl, the heterocyclyl may be attached to the alkenylene chain at the nitrogen atom. The alkenylene chain of the heterocyclylalkenyl radical may be optionally substituted as defined above for an alkenylene chain. The heterocyclyl part of the heterocyclylalkenyl radical may be optionally substituted as defined above for a heterocyclyl radical.

"Heterocyclylalkynyl" refers to a radical of the formula —$R_eR_h$ where $R_e$ is an alkynylene chain as defined above and $R_h$ is a heterocyclyl radical as defined above, and if the heterocyclyl is a nitrogen-containing heterocyclyl, the heterocyclyl may be attached to the alkynyl radical at the nitrogen atom. The alkynylene chain part of the heterocyclylalkynyl radical may be optionally substituted as defined above for an alkynylene chain. The heterocyclyl part of the heterocyclylalkynyl radical may be optionally substituted as defined above for a heterocyclyl radical.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. A heteroaryl radical is commonly, but not necessarily, attached to the parent molecule via an aromatic ring of the heteroaryl radical. For purposes of this invention, the heteroaryl radical may be a monocyclic, bicyclic or tricyclic ring system, which may include spiro ring systems; and the nitrogen, carbon or sulfur atoms in the heteroaryl radical may be optionally oxidized; the nitrogen atom may be optionally quaternized. For purposes of this invention, the aromatic ring of the heteroaryl radical need not contain a heteroatom, as long as one ring of the heteroaryl radical contains a heteroatom. For example, 1,2,3,4-tetrahydroisoquinolin-7-yl is considered a "heteroaryl" for the purposes of this invention. Except for bicyclic heteroaryls of formula (II), bridged bicyclic heteroaryls of formula (III) and polycyclic heteroaryls containing more than 14 ring atoms, as described above in the Summary of the Invention, a "heteroaryl" radical as defined herein can not contain rings having more than 7 members and cannot contain rings wherein two non-adjacent members thereof are connected through an atom or a group of atoms (i.e., a bridged ring system). Examples of heteroaryl radicals include, but are not limited to, azepinyl, acridinyl, benzimidazolyl, benzindolyl, 1,3-benzodioxolyl, benzofuranyl, benzoxazolyl, benzothiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 7',8'-dihydro-5'H-spiro[[1,3]dioxolane-2,6'-quinoline]-3'-yl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, furopyrimidinyl, furopyridazinyl, furopyrazinyl, isothiazolyl, imidazolyl, imidazopyrimidinyl, imidazopyridazinyl, imidazopyrazinyl, indazolyl, indolyl, indazolyl, isoindolyl, indolinyl, isoindolinyl, isoquinolinyl (isoquinolyl), indolizinyl, isoxazolyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, phenanthridinyl, pteridinyl, purinyl, pyrrolyl, pyrazolyl, pyrazolo[3,4-d]pyrimidinyl, pyridinyl (pyridyl), pyrido[3,2-d]pyrimidinyl, pyrido[3,4-d]pyrimidinyl, pyrazinyl, pyrimidinyl, pyridazinyl (pyridazyl), pyrrolyl, pyrrolopyrimidinyl, pyrrolopyridazinyl, pyrrolopyrazinyl, quinazolinyl, quinoxalinyl, quinolinyl, quinuclidinyl, tetrahydroquinolinyl, 5,6,7,8-tetrahydroquinazolinyl, 2,3,4,5-tetrahydrobenzo[b]oxepinyl, 3,4-dihydro-2H-benzo[b][1,4]dioxepinyl, 6,7,8,9-tetrahydro-5H-cyclohepta[b]pyridinyl, 6,7,8,9-tetrahydro-5H-pyrido[3,2-c]azepinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, 1,2,3,4-tetrahydroisoquinolin-7-yl, triazinyl, thieno[2,3-d]pyrimidinyl, thienopyrimidinyl (e.g., thieno[3,2-d]pyrimidinyl), thieno[2,3-c]pyridinyl, thienopyridazinyl, thienopyrazinyl, and thiophenyl (thienyl). Unless stated otherwise specifically in the specification, the term "optionally substituted heteroaryl" is meant to include heteroaryl radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{20}$, —R$^{21}$—N(R$^{20}$)C(O)R$^{20}$, —R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N(R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, may optionally form an optionally substituted N-heterocyclyl or an optionally substituted N-heteroaryl, and each R$^{21}$ is independently a direct bond or a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals. "Polycyclic heteroaryl containing more than 14 ring atoms" refers to a 15- to 20-membered ring system radical comprising hydrogen atoms, one to fourteen carbon atoms, one to eight heteroatoms selected from the group consisting of nitrogen, oxygen and sulfur, and at least one aromatic ring. A "polycyclic heteroaryl containing more than 14 ring atoms" radical is commonly, but not necessarily, attached to the parent molecule via an aromatic ring of the "polycyclic heteroaryl containing more than 14 ring atoms" radical. For purposes of this invention, the "polycyclic heteroaryl containing more than 14 ring atoms" radical may be a bicyclic, tricyclic or tetracyclic ring system, which may include fused or spiro ring systems; and the nitrogen, carbon or sulfur atoms in the "polycyclic heteroaryl containing more than 14 ring atoms" radical may be optionally oxidized and the nitrogen atom may also be optionally quaternized. For purposes of this invention, the aromatic ring of the "polycyclic heteroaryl containing more than 14 ring atoms" radical need not contain a heteroatom, as long as one ring of the "polycyclic heteroaryl containing more than 14 ring atoms" radical contains a heteroatom. Examples of "polycyclic heteroaryl containing more than 14 ring atoms" radicals include, but are not limited to, 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl. Unless stated otherwise specifically in the specification, the term "optionally substituted polycyclic heteroaryl containing more than 14 ring atoms" is meant to include "polycyclic heteroaryl containing more than 14 ring atoms" radicals as defined above which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{20}$, —R$^{21}$—N(R$^{20}$)C(O)R$^{20}$, —R$^{21}$—N(R$^{20}$)S(O)$_t$R$^{20}$ (where t is 1 or 2), —R$^{21}$—S(O)$_t$OR$^{20}$ (where t is 1 or 2), —R$^{21}$—S(O)$_p$R$^{20}$ (where p is 0, 1 or 2), and —R$^{21}$—S(O)$_t$N(R$^{20}$)$_2$ (where t is 1 or 2), where each R$^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two R$^{20}$'s, together with the common nitrogen to which they are both attached, may optionally form an optionally substituted N-heterocyclyl or an optionally substituted N-heteroaryl, and each R$^{21}$ is independently a direct bond or a straight or branched alkylene or alkenylene chain.

"Heteroarylalkyl" refers to a radical of the formula —R$_b$R$_i$ where R$_b$ is an alkylene chain as defined above and R$_i$ is a heteroaryl radical as defined above. The heteroaryl part of the heteroarylalkyl radical may be optionally substituted as defined above for a heteroaryl. The alkylene chain part of the heteroarylalkyl radical may be optionally substituted as defined above for an alkylene chain.

"Heteroarylalkenyl" refers to a radical of the formula —R$_d$R$_i$ where R$_d$ is an alkenylene chain as defined above and R$_i$ is a heteroaryl radical as defined above. The heteroaryl part of the heteroarylalkenyl radical may be optionally substituted as defined above for a heteroaryl. The alkenylene chain part of the heteroarylalkenyl radical may be optionally substituted as defined above for an alkenylene chain.

"Heteroarylalkynyl" refers to a radical of the formula —R$_e$R$_i$ where R$_e$ is an alkynylene chain as defined above and R$_i$ is a heteroaryl radical as defined above. The heteroaryl part of the heteroarylalkynyl radical may be optionally substituted as defined above for a heteroaryl. The alkynylene chain part of the heteroarylalkynyl radical may be optionally substituted as defined above for an alkynylene chain.

"Hydroxyalkyl" refers to an alkyl radical as defined above which is substituted by one or more hydroxy radicals (—OH).

"Hydroxyalkenyl" refers to an alkenyl radical as defined above which is substituted by one or more hydroxy radicals (—OH).

"Hydroxyalkenyl" refers to an alkynyl radical as defined above which is substituted by one or more hydroxy radicals (—OH).

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substituents on the functional group are also "optionally substituted" and so on, for the purposes of this invention, such iterations are limited to five, preferably such iterations are limited to two.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)— or (S)— or, as (D)- or (L)- for amino acids. The present invention is meant to include all such possible isomers, as well as their racemic and optically pure forms. Optically active (+) and (−), (R)— and (S)—, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"Atropisomers" are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation around the single bonds emanating from the core triazole structure, atropisomers are also possible and are also specifically included in the compounds of the invention.

The chemical naming protocol and structure diagrams used herein are a modified form of the I.U.P.A.C. nomenclature system wherein the compounds of the invention are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For purposes of this invention, the depiction of the bond attaching the $R^3$ substituent to the parent triazole moiety in formula (I), as shown below:

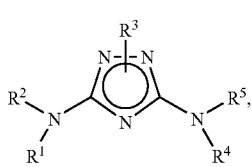
(I)

is intended to include only the two regioisomers shown below, i.e., compounds of formula (Ia) and (Ib):

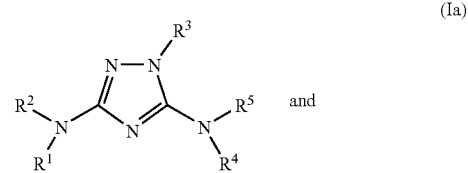
(Ia)

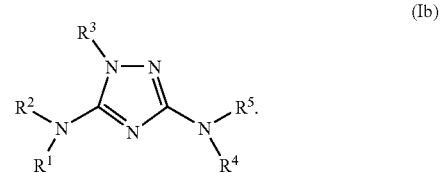
(Ib)

The numbering system of the ring atoms in compounds of formula (Ia) is shown below:

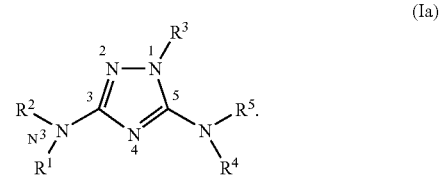
(Ia)

For example, a compound of formula (Ia) wherein $R^1$, $R^4$ and $R^5$ are each hydrogen, $R^2$ is 4(1H)-oxo-2,3,5,6-tetrahydrobenzo[d]azocin-8-yl and $R^3$ is 6,7-dihydro-5H-benzo[6,7]cyclohepta[1,2-c]pyridazin-3-yl; i.e., a compound of the following formula:

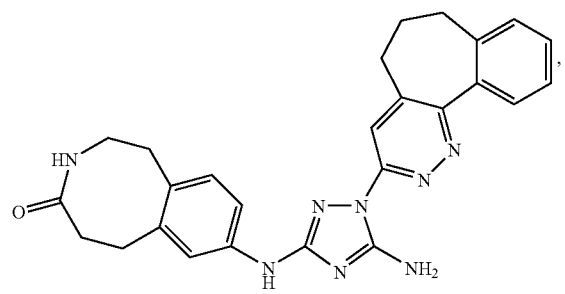

is named herein as 1-(6,7-dihydro-5H-benzo[6,7]cyclohepta[1,2-c]pyridazin-3-yl)-$N^3$-(4(1H)-oxo-2,3,5,6-tetrahydrobenzo[d]azocin-8-yl)-1H-1,2,4-triazole-3,5-diamine.

The numbering system of the ring atoms in compounds of formula (Ib) is shown below:

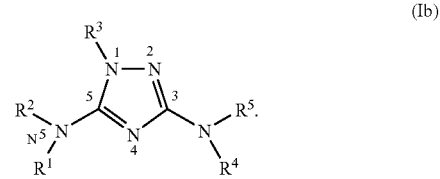
(Ib)

Compounds of formula (Ib) are similarly named herein.

For purposes of this invention the following structure in the bicyclic aryls of formula (II) and the bicyclic heteroaryls of formula (II):

herein designated as "A", is intended to illustrate an alkylene, alkenylene or alkynylene chain connecting the carbon at the alpha (α) position of the ring containing $B^1$, $B^2$, $B^3$ and $B^4$, to the carbon at the beta (β) position of the ring, as noted below:

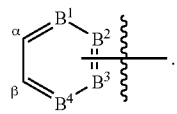

Embodiments of the Invention

Of the various aspects of the compounds of formula (I), as set forth above in the Summary of the Invention, certain embodiments are preferred.

Accordingly, one embodiment of the compounds of formula (I), as set forth above in the Summary of the Invention, is wherein the compound of formula (I) is a compound of formula (Ia):

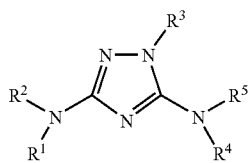

wherein:
$R^1$, $R^4$ and $R^5$ are independently selected from hydrogen, alkyl, aryl, aralkyl, —C(O)$R^9$ or —C(O)N($R^6$)$R^7$;
one of $R^2$ and $R^3$ is selected from one of the following and the other is selected from the other two of the following:
a) a bicyclic aryl of formula (II) or a bicyclic heteroaryl of formula (II):

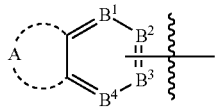

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by —N$R^9$—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that one of $B^1$, $B^2$, $B^3$ and $B^4$ is a carbon directly bonded to the nitrogen to which its corresponding $R^2$ or $R^3$ is attached;

b) a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); or c) a bridged bicyclic aryl of formula (III) or a bridged bicyclic heteroaryl of formula (III):

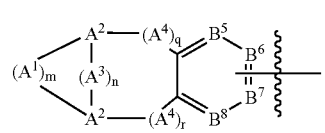

where:
m and n are independently 1 to 4;
q and r are independently 0 to 3;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);
each $A^2$ is independently selected from the group consisting of C($R^8$) and N;
$B^5$, $B^6$, $B^7$ and $B^8$ are each independently selected from the group consisting of =C($R^{13}$)— and =N—, provided that one of $B^5$, $B^6$, $B^7$ and $B^8$ is a carbon directly bonded to the nitrogen to which its corresponding $R^2$ or $R^3$ is attached;
each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{11}-OR^9$, $-R^{11}-CN$, $-R^{11}-NO_2$, $-R^{11}-N(R^9)_2$, $-R^{11}-C(O)OR^9$ and $-R^{11}-C(O)N(R^9)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2), or two $R^8$'s on adjacent carbons can combine to form a double bond;

each $R^9$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl;

each $R^{10}$ is independently selected from the group consisting of a direct bond, an optionally substituted straight or branched alkylene chain, an optionally substituted straight or branched alkenylene chain and an optionally substituted straight or branched alkynylene chain;

each $R^{11}$ is independently selected from the group consisting of an optionally substituted straight or branched alkylene chain, an optionally substituted straight or branched alkenylene chain and an optionally substituted straight or branched alkynylene chain;

each $R^{12}$ is hydrogen, alkyl, cyano, nitro or $-OR^9$; and each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, $-R^{10}-OR^9$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2);

as an isolated stereoisomer or a mixture thereof, or as a pharmaceutically acceptable salt thereof.

Another embodiment is wherein the compound of formula (I) is a compound of formula (Ia), as set forth above, wherein:
$R^1$, $R^4$ and $R^5$ are each hydrogen;
$R^2$ is a bicyclic aryl of formula (II) or a bicyclic heteroaryl of formula (II):

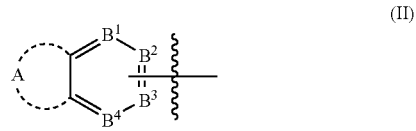

(II)

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by $-NR^9-$, $=N-$, $-O-$, $-S(O)_p-$ (where p is 0, 1 or 2) or $-P(O)_p-$ (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $B^1$, $B^2$, $B^3$ and $B^4$ are each independently selected from the group consisting of $=C(R^{13})-$ and $=N-$, provided that one of $B^1$, $B^2$, $B^3$ and $B^4$ is a carbon directly bonded to the nitrogen to which $R^2$ is attached; and $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-$ S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2);
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic aryl of formula (II):

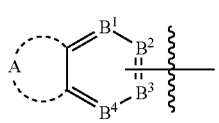

(II)

where:
A is an alkylene chain containing six carbons, an alkenylene chain containing six carbons, or an alkynylene chain containing six carbons, where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^2$ is attached; and R$^3$ is polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2);
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic aryl of formula (II):

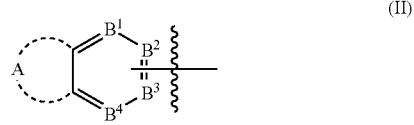

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2);
and each R$^6$, each R$^7$, each R$^8$, each R$^9$, each R$^{10}$, each R$^{11}$, each R$^{12}$ and each R$^{13}$ is as defined above for the compounds of formula (Ia).

Of this embodiment, a preferred embodiment is a compound of formula (Ia) wherein:
$R^1$, $R^4$ and $R^5$ are each hydrogen;
$R^2$ is a bicyclic aryl of formula (II):

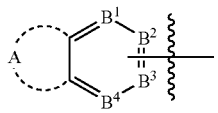

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, optionally substituted heterocyclyl, —$R^{10}$—$OR^9$, —$R^{10}$—$N(R^6)R^7$, —$R^{10}$—$C(O)OR^9$, and —$R^{10}$—$C(O)N(R^6)R^7$; and $B^1$, $B^2$ and $B^4$ are each independently =$C(R^{13})$— and $B^3$ is a carbon directly bonded to the nitrogen to which $R^2$ is attached; and $R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl and alkyl;

and each $R^6$, each $R^7$, each $R^8$, each $R^9$, each $R^{10}$, each $R^{11}$, each $R^{12}$ and each $R^{13}$ is as defined above for the compounds of formula (Ia).

Of this embodiment, a preferred embodiment is the compound of formula (Ia) which is 1-(6,7-dihydro-5H-benzo[6,7]cyclohepta[1,2-c]pyridazin-3-yl)-$N^3$-(6-pyrrolidin-1-yl-5,6,7,8,9,10-hexahydrobenzo[8]annulen-3-yl)-1H-1,2,4-triazole-3,5-diamine.

Another embodiment is wherein the compound of formula (I) is a compound of formula (Ia), as set forth above, wherein:
$R^1$, $R^4$ and $R^5$ are each hydrogen;
$R^2$ is a bicyclic heteroaryl of formula (II):

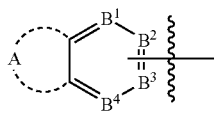

(II)

where:
A is an alkylene chain containing six carbons, an alkenylene chain containing six carbons, or an alkynylene chain containing six carbons, where each carbon of the alkylene, alkenylene or alkynylene chain may be replaced by —$N(R^9)$—, =$N$—, —$O$—, —$S(O)_p$— (where p is 0, 1 or 2) or —$P(O)_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =$N$—$O$—$R^6$, —$R^{10}$—$OR^9$, —$R^{10}$—$O$—$R^{11}$—$OR^9$, —$R^{10}$—$O$—$R^{11}$—$O$—$R^{11}$—$OR^9$, —$R^{10}$—$O$—$R^{11}$—CN, —$R^{10}$—$O$—$R^{11}$—$C(O)OR^9$, —$R^{10}$—$O$—$R^{11}$—$C(O)N(R^6)R^7$, —$R^{10}$—$O$—$R^{11}$—$S(O)_pR^9$ (where p is 0, 1 or 2), —$R^{10}$—$O$—$R^{11}$—$N(R^6)R^7$, —$R^{10}$—$O$—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and $B^1$, $B^2$, $B^3$ and $B^4$ are each independently selected from the group consisting of =$C(R^{13})$— and =$N$—, provided that at least one carbon in A is replaced with —$N(R^9)$—, =$N$—, —$O$—, —$S(O)_p$— (where p is 0, 1 or 2) or —$P(O)_p$— (where p is 0, 1 or 2) or one of $B^1$, $B^2$, $B^3$ and $B^4$ is =$N$—, and one of $B^1$, $B^2$, $B^3$ and $B^4$ is a carbon directly bonded to the nitrogen to which $R^2$ is attached; and $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—$OR^9$, —$R^{10}$—$O$—$R^{11}$—$OR^9$, —$R^{10}$—$O$—$R^{11}$—$O$—$R^{11}$—$OR^9$, —$R^{10}$—$O$—$R^{11}$—CN, —$R^{10}$—$O$—$R^{11}$—$C(O)OR^9$, —$R^{10}$—$O$—$R^{11}$—$C(O)N(R^6)R^7$, —$R^{10}$—$O$—$R^{11}$—$S(O)_pR^9$ (where p is 0, 1 or 2), —$R^{10}$—$O$—$R^{11}$—$N(R^6)R^7$, —$R^{10}$—$O$—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2);

and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bicyclic heteroaryl of formula (II):

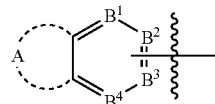

(II)

where:
A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— or =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic heteroaryl of formula (II):

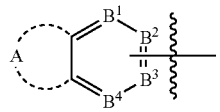

(II)

where:
A is an alkylene chain containing six carbons, where at least one carbon is replaced by —N(R$^9$)— and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and each R$^6$, each R$^7$, each R$^8$, each R$^9$, each R$^{10}$, each R$^{11}$, each R$^{12}$ and each R$^{13}$ is as defined above for the compounds of formula (Ia).

Of this embodiment, a preferred embodiment is a compound of formula (Ia) wherein:
R$^1$, R$^4$ and R$^5$ are each hydrogen;
R$^2$ is a bicyclic heteroaryl of formula (II):

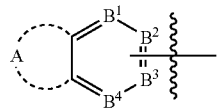

(II)

where:
A is an alkylene chain containing six carbons, where at least one carbon is replaced by —N($R^9$)— and where each carbon in the alkylene chain is independently optionally substituted by one or two substituents selected from the group consisting of oxo, thioxo, cyano, nitro, halo, haloalkyl, and alkyl; and $B^1$, $B^2$ and $B^4$ are each independently =C($R^{13}$)— and $B^3$ is a carbon directly bonded to the nitrogen to which $R^2$ is attached; and $R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl and alkyl;

and each $R^6$, each $R^7$, each $R^8$, each $R^9$, each $R^{10}$, each $R^{11}$, each $R^{12}$ and each $R^{13}$ is as defined above for the compounds of formula (Ia).

Of this embodiment, a preferred embodiment is a compound of formula (Ia) selected from the group consisting of:
1-(6,7-dihydro-5H-benzo[6,7]cyclohepta[1,2-c]pyridazin-3-yl)-$N^3$-(4(1H)-oxo-2,3,5,6-tetrahydrobenzo[d]azocin-8-yl)-1H-1,2,4-triazole-3,5-diamine;
1-(6,7-dihydro-5H-benzo[6,7]cyclohepta[1,2-c]pyridazin-3-yl)-$N^3$-(3-cyclopentyl-1,2,3,4,5,6-hexahydrobenzo[d]azocin-8-yl)-1H-1,2,4-triazole-3,5-diamine;
1-(6,7-dihydro-5H-benzo[6,7]cyclohepta[1,2-c]pyridazin-3-yl)-$N^3$-(3-cyclopentyl-1,2,3,4,5,6-hexahydrobenzo[d]azocin-9-yl)-1H-1,2,4-triazole-3,5-diamine;
1-(6,7-dihydro-5H-benzo[6,7]cyclohepta[1,2-c]pyridazin-3-yl)-$N^3$-(1(2H)-oxo-3,4,5,6-tetrahydrobenzo[c]azocin-9-yl)-1H-1,2,4-triazole-3,5-diamine;
1-(6,7-dihydro-5H-benzo[6,7]cyclohepta[1,2-c]pyridazin-3-yl)-$N^3$-(1(2H)-oxo-3,4,5,6-tetrahydrobenzo[c]azocin-9-yl)-1H-1,2,4-triazole-3,5-diamine;
1-(6,7-dihydro-5H-benzo[6,7]cyclohepta[1,2-c]pyridazin-3-yl)-$N^3$-(1,2,3,4,5,6-hexahydrobenzo[c]azocin-9-yl)-1H-1,2,4-triazole-3,5-diamine.

Another embodiment is wherein the compound of formula (I) is a compound of formula (Ia), as set forth above, wherein:
$R^1$, $R^4$ and $R^5$ are each hydrogen;
$R^2$ is a bicyclic heteroaryl of formula (II):

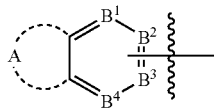

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that at least one of $B^1$, $B^2$, $B^3$ and $B^4$ is =N—, and one of $B^1$, $B^2$, $B^3$ and $B^4$ is a carbon directly bonded to the nitrogen to $R^2$ is attached; and $R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2);

and each $R^6$, each $R^7$, each $R^8$, each $R^9$, each $R^{10}$, each $R^{11}$, each $R^{12}$ and each $R^{13}$ is as defined above for the compounds of formula (Ia).

Of this embodiment, a preferred embodiment is a compound of formula (Ia) wherein:
$R^1$, $R^4$ and $R^5$ are each hydrogen;
$R^2$ is a bicyclic heteroaryl of formula (II):

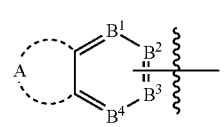

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$ is =N—, $B^3$ and $B^4$ are each independently selected from the group consisting of =C($R^{13}$)— and $B^2$ is a carbon directly bonded to the nitrogen to $R^2$ is attached; and $R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl and alkyl;

and each $R^6$, each $R^7$, each $R^8$, each $R^9$, each $R^{10}$, each $R^{11}$, each $R^{12}$ and each $R^{13}$ is as defined above for the compounds of formula (Ia).

Of this embodiment, a preferred embodiment is a compound of formula (Ia) selected from the group consisting of:

1-(6,7-dihydro-5H-benzo[6,7]cyclohepta[1,2-c]pyridazin-3-yl)-$N^3$-(7-oxo-5,6,8,9,10-pentahydrocycloocta[b]pyridin-3-yl)-1H-1,2,4-triazole-3,5-diamine;

1-(6,7-dihydro-5H-benzo[6,7]cyclohepta[1,2-c]pyridazin-3-yl)-$N^3$-(7-(pyrrolidin-1-yl)-5,6,7,8,9,10-hexahydrocycloocta[b]pyridin-3-yl)-1H-1,2,4-triazole-3,5-diamine;

1-(6,7-dihydro-5H-benzo[6,7]cyclohepta[1,2-c]pyridazin-3-yl)-$N^3$-(7-(methoxyimino)-5,6,7,8,9,10-hexahydrocycloocta[b]pyridin-3-yl)-1H-1,2,4-triazole-3,5-diamine; and 1-(6,7-dihydro-5H-benzo[6,7]cyclohepta[1,2-c]pyridazin-3-yl)-$N^3$-(7-hydroxy-5,6,7,8,9,10-hexahydrocycloocta[b]pyridin-3-yl)-1H-1,2,4-triazole-3,5-diamine.

Another embodiment is wherein the compound of formula (I) is a compound of formula (Ia), as set forth above, wherein:
$R^1$, $R^4$ and $R^5$ are each hydrogen;
$R^2$ is a bicyclic aryl of formula (II) or a bicyclic heteroaryl of formula (II):

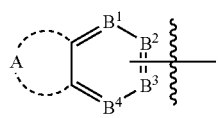

(II)

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by —$NR^9$—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that one of $B^1$, $B^2$, $B^3$ and $B^4$ is a carbon directly bonded to the nitrogen to which $R^2$ is attached; and $R^3$ is a bridged bicyclic aryl of formula (III) or a bridged bicyclic heteroaryl of formula (III):

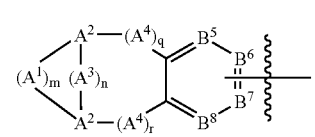

(III)

where:
m and n are independently 1 to 2;
q and r are independently 0 to 3;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);
each $A^2$ is independently selected from the group consisting of C($R^8$) and N;
$B^5$, $B^6$, $B^7$ and $B^8$ are each independently selected from the group consisting of =C($R^{13}$)— and =N—, provided that one of $B^5$, $B^6$, $B^7$ and $B^8$ is a carbon directly bonded to the nitrogen to which $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bicyclic aryl of formula (II):

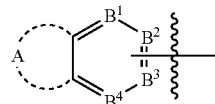

(II)

where:
A is an alkylene chain containing six carbons, an alkenylene chain containing six carbons, or an alkynylene chain containing six carbons, where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and $B^1$, $B^2$, $B^3$ and $B^4$ are each independently =$C(R^{13})$—; provided that one of $B^1$, $B^2$, $B^3$ and $B^4$ is a carbon directly bonded to the nitrogen to which $R^2$ is attached; and $R^3$ is a bridged bicyclic aryl of formula (III):

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently =$C(R^{13})$—, provided that one of $B^5$, $B^6$, $B^7$ and $B^8$ is a carbon directly bonded to the nitrogen to which $R^3$ is attached; and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bicyclic aryl of formula (II):

where:
A is an alkylene chain containing six carbons, an alkenylene chain containing six carbons, or an alkynylene chain containing six carbons, where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and $B^1$, $B^2$, $B^3$ and $B^4$ are each independently =$C(R^{13})$—, provided that one of $B^1$, $B^2$, $B^3$ and $B^4$ is a carbon directly bonded to the nitrogen to which $R^2$ is attached; and $R^3$ is a bridged bicyclic heteroaryl of formula (III):

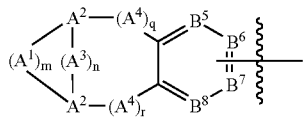

(III)

where:
m and n are independently 1 to 2;
q and r are independently 0 to 2;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of =$C(R^8)$— and =N—;
$B^5$, $B^6$, $B^7$ and $B^8$ are each independently selected from the group consisting of =$C(R^{13})$— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bicyclic aryl of formula (II):

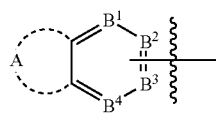

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—OC(O)—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and
$B^1$, $B^2$, $B^3$ and $B^4$ are each independently =$C(R^{13})$—, provided that one of $B^1$, $B^2$, $B^3$ and $B^4$ is a carbon directly bonded to the nitrogen to which $R^2$ is attached; and $R^3$ is a bridged bicyclic heteroaryl of formula (III):

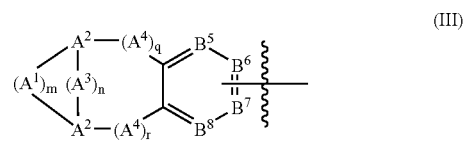

(III)

where:
m and n are independently 1 to 2;
q and r are independently 0 to 2;
each $A_1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of =$C(R^8)$— and =N—;
$B^5$, $B^6$, $B^7$ and $B^8$ are each independently selected from the group consisting of =$C(R^{13})$— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^3$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bicyclic heteroaryl of formula (II):

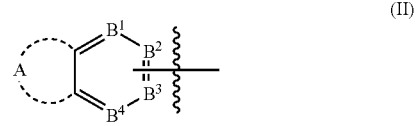

(II)

where:
A is an alkylene chain containing six carbons, an alkenylene chain containing six carbons, or an alkynylene chain containing six carbons, where each carbon of the alkylene, alkenylene or alkynylene chain may be replaced by —$N(R^9)$—, =N—, —O—, —$S(O)_p$— (where p is 0, 1 or 2) or —$P(O)_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—C(NR$^{12}$)N(R$^{12}$)H, —$R^{10}$—OC(O)—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—

S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached; and R$^3$ is a bridged bicyclic aryl of formula (III):

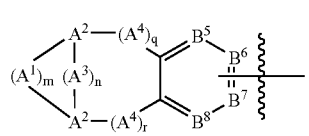

(III)

where:
m and n are independently 1 to 2;
q and r are independently 0 to 2;
each A$^1$, A$^3$ and A$^4$ is independently C(R$^8$)$_2$;
each A$^2$ is independently C(R$^8$);
B$^5$, B$^6$, B$^7$ and B$^8$ are each independently =C(R$^{13}$)—, provided that one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic heteroaryl of formula (II):

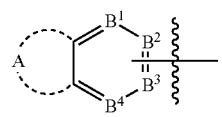

(II)

where:
A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to which R$^2$ is attached; and R$^3$ is a bridged bicyclic aryl of formula (III):

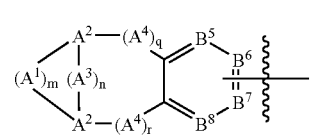

(III)

where:
m and n are independently 1 to 2;
q and r are independently 0 to 2;
each A$^1$, A$^3$ and A$^4$ is independently C(R$^8$)$_2$;
each A$^2$ is independently C(R$^8$);
B$^5$, B$^6$, B$^7$ and B$^8$ are each independently =C(R$^{13}$)—, provided that one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic heteroaryl of formula (II):

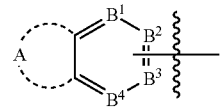

(II)

where:
A is an alkylene chain containing six carbons, an alkenylene chain containing six carbons, or an alkynylene chain containing six carbons, where each carbon of the alkylene, alkenylene or alkynylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached; and R$^3$ is a bridged bicyclic heteroaryl of formula (III):

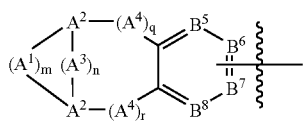

(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently =C(R$^{13}$)— or =N—, provided that at least one of A$^1$, A$^3$ and A$^4$ is independently selected from the group consisting of O, S(O)$_p$ (where p is 0, 1 or 2), P(O)$_p$ (where p is 0, 1 or 2) and N(R$^9$), or A$^3$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic heteroaryl of formula (II):

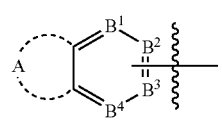

(II)

where:
A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and
B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached; and R$^3$ is a bridged bicyclic heteroaryl of formula (III):

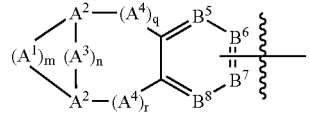

(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— or =N—, provided that at least one of A$^1$, A$^3$ and A$^4$ is independently selected from O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bicyclic heteroaryl of formula (II):

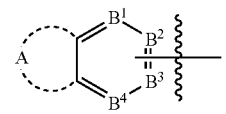

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and
B$^1$, B$^2$, B$^3$ and B$^4$ are each independently selected from the group consisting of =C(R$^{13}$)— and =N—, provided that at least one of B$^1$, B$^2$, B$^3$ and B$^4$ is =N—, and one of B$^1$, B$^2$, B$^3$ and B$^4$ is a carbon directly bonded to the nitrogen to R$^2$ is attached; and $R^3$ is a bridged bicyclic heteroaryl of formula (III):

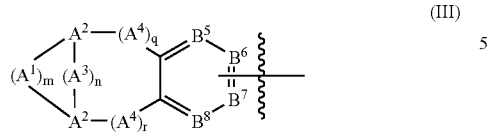

(III)

where:
m and n are independently 1 to 2;
q and r are independently 0 to 2;
each $A^1$, $A^3$ and $A^4$ is independently $C(R^8)_2$;
each $A^2$ is independently selected from the group consisting of $C(R^8)$ and N;
$B^5$, $B^6$, $B^7$ and $B^8$ are each independently selected from the group consisting of =$C(R^{13})$— or =N—, provided that at least one $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached.

Another embodiment is wherein the compound of formula (I) is a compound of formula (Ia), as set forth above, which is 1-(1,4-ethano-8-pyridin-4-yl-1,2,3,4-tetrahydro-1,5-naphthyridin-6-yl)-$N^3$-(7-oxo-5,6,7,8,9,10-hexahydrocycloocta[b]pyridin-3-yl)-1H-1,2,4-triazole-3,5-diamine.

Another embodiment is wherein the compound of formula (I) is a compound of formula (Ia), as set forth above, wherein:
$R^1$, $R^4$ and $R^5$ are each hydrogen;
$R^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
$R^3$ is a bicyclic aryl of formula (II) or a bicyclic heteroaryl of formula (II):

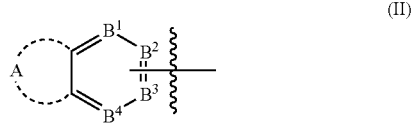

(II)

where:
A is an alkylene chain containing six to ten carbons, an alkenylene chain containing six to ten carbons, or an alkynylene chain containing six to ten carbons, where each carbon of the alkylene, alkenylene or alkynylene chain may be replaced by —N($R^9$)—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
$B^1$, $B^2$, $B^3$ and $B^4$ are each independently selected from the group consisting of =$C(R^{13})$— and =N—, provided that one of $B^1$, $B^2$, $B^3$ and $B^4$ is a carbon directly bonded to the nitrogen to which $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
$R^3$ is a bicyclic aryl of formula (II):

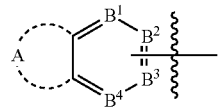

(II)

where:
A is an alkylene chain containing six carbons, an alkenylene chain containing six carbons, or an alkynylene chain containing six carbons, where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—

O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^3$ is attached; and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and
R$^3$ is a bicyclic aryl of formula (II):

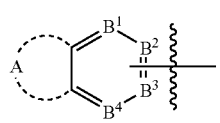

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^3$ is attached; and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and
R$^3$ is a bicyclic heteroaryl of formula (II):

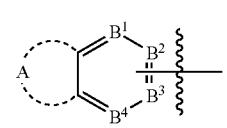

where:
A is an alkylene chain containing six carbons, an alkenylene chain containing six carbons, or an alkynylene chain containing six carbons, where each carbon of the alkylene, alkenylene or alkynylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—

S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached;

and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein: R$^1$, R$^4$ and R$^5$ are each hydrogen;

R$^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bicyclic heteroaryl of formula (II):

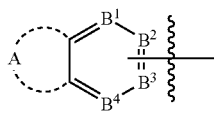

(II)

where:

A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached;

and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein: R$^1$, R$^4$ and R$^5$ are each hydrogen;

R$^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bicyclic heteroaryl of formula (II):

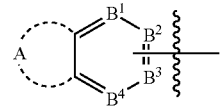

(II)

where:

A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—

C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one of B$^1$, B$^2$, B$^3$ and B$^4$ is =N—, and one of B$^1$, B$^2$, B$^3$ and B$^4$ is a carbon directly bonded to the nitrogen to R$^2$ is attached.

Another embodiment is wherein the compound of formula (I) is a compound of formula (Ia), as set forth above, which is 1-(5,6,7,8,9,10-hexahydrocycloocta[d]pyrimidin-4-yl)-N$^3$-(5,6,8,9-tetrahydrospiro[benzo[7]annulene-7,2'-[1,3]dioxolane]-3-yl)-1H-1,2,4-triazole-3,5-diamine.

Another embodiment is wherein the compound of formula (I) is a compound of formula (Ia), as set forth above, wherein:
R$^1$, R$^4$ and R$^5$ are each hydrogen;
R$^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bridged bicyclic aryl of formula (III) or a bridged bicyclic heteroaryl of formula (III):

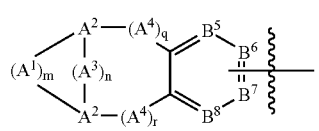

(III)

where:
m and n are independently 1 to 2;
q and r are independently 0 to 3;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) or N;
B$^5$, B$^6$, B$^7$ and B$^8$ are each independently =C(R$^{13}$)— or =N—, provided that one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bridged bicyclic aryl of formula (III):

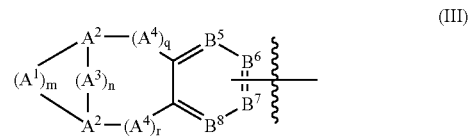

(III)

where:
m and n are independently 1 to 2;
q and r are independently 0 to 2;
each A$^1$, A$^3$ and A$^5$ is independently C(R$^8$)$_2$;
each A$^2$ is independently C(R$^8$);
B$^5$, B$^6$, B$^7$ and B$^8$ are each independently =C(R$^{13}$)—, provided that one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bridged bicyclic aryl of formula (III):

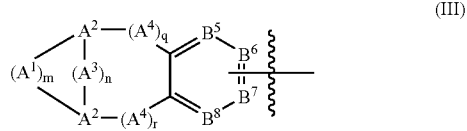
(III)

where:
m and n are independently 1 to 2;
q and r are independently 0 to 2;
each A$^1$, A$^3$ and A$^4$ is independently C(R$^8$)$_2$;
each A$^2$ is independently C(R$^8$);
B$^5$, B$^6$, B$^7$ and B$^8$ are each independently =C(R$^{13}$)—, provided that one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bridged bicyclic heteroaryl of formula (III):

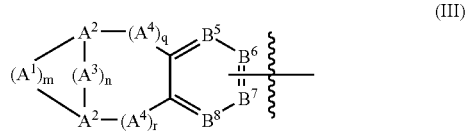
(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that at least one of A$^1$, A$^3$ and A$^4$ is independently selected from the group consisting of O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bridged bicyclic heteroaryl of formula (III):

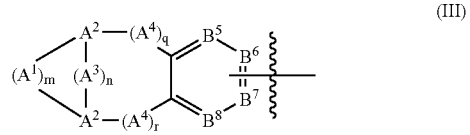
(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) or N;
B$^5$, B$^6$, B$^7$ and B$^8$ are each independently selected from the group consisting of =C(R$^{13}$)— and =N—, provided that at least one of A$^1$, A$^3$ and A$^4$ is independently selected from the group consisting of O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached;
and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III) or a bridged bicyclic heteroaryl of formula (III):

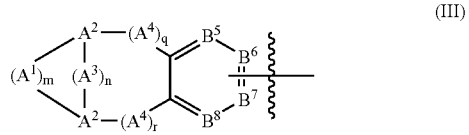

(III)

where:
m and n are independently 1 to 2;
q and r are independently 0 to 3;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of $C(R^8)$ and N;
$B^5$, $B^6$, $B^7$ and $B^8$ are each independently selected from the group consisting of $=C(R^{13})—$ and $=N—$, provided that one of $B^5$, $B^6$, $B^7$ and $B^8$ is a carbon directly bonded to the nitrogen to which $R^2$ is attached; and
$R^3$ is a bicyclic aryl of formula (II) or a bicyclic heteroaryl of formula (II):

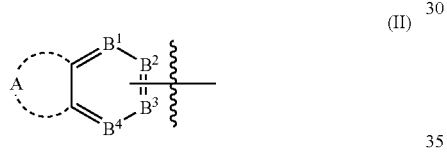

(II)

where:
A is an alkylene chain containing six to ten carbons, an alkenylene chain containing six to ten carbons, or an alkynylene chain containing six to ten carbons, where each carbon of the alkylene, alkenylene or alkynylene chain may be replaced by $—N(R^9)—$, $=N—$, $—O—$, $—S(O)_p—$ (where p is 0, 1 or 2) or $—P(O)_p—$ (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N—O—R^6$, $—R^{10}—OR^9$, $—R^{10}—O—R^{11}—OR^9$, $—R^{10}—O—R^{11}—O—R^{11}—OR^9$, $—R^{10}—O—R^{11}—CN$, $—R^{10}—O—R^{11}—C(O)OR^9$, $—R^{10}—O—R^{11}—C(O)N(R^6)R^7$, $—R^{10}—O—R^{11}—S(O)_pR^9$ (where p is 0, 1 or 2), $—R^{10}—O—R^{11}—N(R^6)R^7$, $—R^{10}—O—R^{11}—C(NR^{12})N(R^{12})H$, $—R^{10}—OC(O)—R^9$, $—R^{10}—N(R^6)R^7$, $—R^{10}—C(O)R^9$, $—R^{10}—C(O)OR^9$, $—R^{10}—C(O)N(R^6)R^7$, $—R^{10}—N(R^6)C(O)OR^9$, $—R^{10}—N(R^6)C(O)R^9$, $—R^{10}—N(R^6)S(O)_tR^9$ (where t is 1 or 2), $—R^{10}—S(O)_tOR^9$ (where t is 1 or 2), $—R^{10}—S(O)_pR^9$ (where p is 0, 1 or 2), and $—R^{10}—S(O)_tN(R^6)R^7$ (where t is 1 or 2); and
$B^1$, $B^2$, $B^3$ and $B^4$ are each independently selected from the group consisting of $=C(R^{13})—$ and $=N—$, provided that one of $B^1$, $B^2$, $B^3$ and $B^4$ is a carbon directly bonded to the nitrogen to which $R^3$ is attached;

and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III):

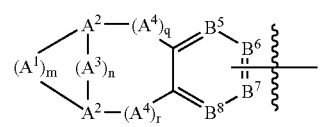

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently $=C(R^{13})—$, provided that one of $B^5$, $B^6$, $B^7$ and $B^8$ is a carbon directly bonded to the nitrogen to which $R^2$ is attached; and
$R^3$ is a bicyclic aryl of formula (II):

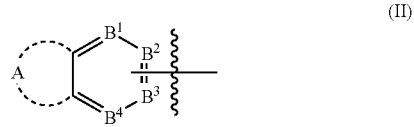

(II)

where:
A is an alkylene chain containing six carbons, an alkenylene chain containing six carbons, or an alkynylene chain containing six carbons, where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N—O—R^6$, $—R^{10}—OR^9$, $—R^{10}—O—R^{11}—OR^9$, $—R^{10}—O—R^{11}—O—R^{11}—OR^9$, $—R^{10}—O—R^{11}—CN$, $—R^{10}—O—R^{11}—C(O)OR^9$, $—R^{10}—O—R^{11}—C(O)N(R^6)R^7$, $—R^{10}—O—R^{11}—S(O)_pR^9$ (where p is 0, 1 or 2), $—R^{10}—O—R^{11}—N(R^6)R^7$, $—R^{10}—O—R^{11}—C(NR^{12})N(R^{12})H$, $—R^{10}—OC(O)—R^9$, $—R^{10}—N(R^6)R^7$, $—R^{10}—C(O)R^9$, $—R^{10}—C(O)OR^9$, $—R^{10}—C(O)N(R^6)R^7$, $—R^{10}—N(R^6)C(O)OR^9$, $—R^{10}—N(R^6)C(O)R^9$, $—R^{10}—N(R^6)S(O)_tR^9$ (where t is 1 or 2), $—R^{10}—S(O)_tOR^9$ (where t is 1 or 2), $—R^{10}—S(O)_pR^9$ (where p is 0, 1 or 2), and $—R^{10}—S(O)_tN(R^6)R^7$ (where t is 1 or 2); and
$B^1$, $B^2$, $B^3$ and $B^4$ are each independently $=C(R^{13})—$, provided that one of $B^1$, $B^2$, $B^3$ and $B^4$ is a carbon directly bonded to the nitrogen to which $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;

$R^2$ is a bridged bicyclic aryl of formula (III):

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently $=C(R^{13})—$, provided that one of $B^5$, $B^6$, $B^7$ and $B^8$ is a carbon directly bonded to the nitrogen to which $R^2$ is attached; and
$R^3$ is a bicyclic aryl of formula (II):

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N—O—R^6$, $—R^{10}—OR^9$, $—R^{10}—OC(O)—R^9$, $—R^{10}—N(R^6)R^7$, $—R^{10}—C(O)R^9$, $—R^{10}—C(O)OR^9$, $—R^{10}—C(O)N(R^6)R^7$, $—R^{10}—N(R^6)C(O)OR^9$, $—R^{10}—N(R^6)C(O)R^9$, $—R^{10}—N(R^6)S(O)_tR^9$ (where t is 1 or 2), $—R^{10}—S(O)_tOR^9$ (where t is 1 or 2), $—R^{10}—S(O)_pR^9$ (where p is 0, 1 or 2), and $—R^{10}—S(O)_tN(R^6)R^7$ (where t is 1 or 2); and
$B^1$, $B^2$, $B^3$ and $B^4$ are each independently $=C(R^{13})—$, provided that one of $B^1$, $B^2$, $B^3$ and $B^4$ is a carbon directly bonded to the nitrogen to which $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III):

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently $=C(R^{13})—$, provided that one of $B^5$, $B^6$, $B^7$ and $B^8$ is a carbon directly bonded to the nitrogen to which $R^2$ is attached; and
$R^3$ is a bicyclic heteroaryl of formula (II):

(II)

where:
A is an alkylene chain containing six carbons, an alkenylene chain containing six carbons, or an alkynylene chain containing six carbons, where each carbon of the alkylene, alkenylene or alkynylene chain may be replaced by $—N(R^9)—$, $=N—$, $—O—$, $—S(O)_p—$ (where p is 0, 1 or 2) or $—P(O)_p—$ (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N—O—R^6$, $—R^{10}—OR^9$, $—R^{10}—O—R^{11}—OR^9$, $—R^{10}—O—R^{11}—O—R^{11}—OR^9$, $—R^{10}—O—R^{11}—CN$, $—R^{10}—O—R^{11}—C(O)OR^9$, $—R^{10}—O—R^{11}—C(O)N(R^6)R^7$, $—R^{10}—O—R^{11}—S(O)_pR^9$ (where p is 0, 1 or 2), $—R^{10}—O—R^{11}—N(R^6)R^7$, $—R^{10}—O—R^{11}—C(NR^{12})N(R^{12})H$, $—R^{10}—OC(O)—R^9$, $—R^{10}—N(R^6)R^7$, $—R^{10}—C(O)R^9$, $—R^{10}—C(O)OR^9$, $—R^{10}—C(O)N(R^6)R^7$, $—R^{10}—N(R^6)C(O)OR^9$, $—R^{10}—N(R^6)C(O)R^9$, $—R^{10}—N(R^6)S(O)_tR^9$ (where t is 1 or 2), $—R^{10}—S(O)_tOR^9$ (where t is 1 or 2), $—R^{10}—S(O)_pR^9$ (where p is 0, 1 or 2), and $—R^{10}—S(O)_tN(R^6)R^7$ (where t is 1 or 2); and
$B^1$, $B^2$, $B^3$ and $B^4$ are each independently selected from the group consisting of $=C(R^{13})—$ and $=N—$, provided that at least one carbon in A is replaced with $—N(R^9)—$, $=N—$, $—O—$, $—S(O)_p—$ (where p is 0, 1 or 2) or $—P(O)_p—$ (where p is 0, 1 or 2) or one of $B^1$, $B^2$, $B^3$ and $B^4$ is $=N—$, and one of $B^1$, $B^2$, $B^3$ and $B^4$ is a carbon directly bonded to the nitrogen to $R^3$ is attached;
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III):

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;

B⁵, B⁶, B⁷ and B⁸ are each independently =C(R¹³)—, provided that one of B⁵, B⁶, B⁷ and B⁸ is a carbon directly bonded to the nitrogen to which R² is attached; and R³ is a bicyclic heteroaryl of formula (II):

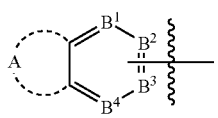

(II)

where:
A is an alkylene chain containing six carbons, where each carbon of the alkylene chain may be replaced by —N(R⁹)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R⁶, —R¹⁰—OR⁹, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁹, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2); and B¹, B², B³ and B⁴ are each independently selected from the group consisting of =C(R¹³)— and =N—, provided that at least one carbon in A is replaced with —N(R⁹)—, =N—, —O—, —S(O)$_p$— (where p is 0, 1 or 2) or —P(O)$_p$— (where p is 0, 1 or 2) or one of B¹, B², B³ and B⁴ is =N—, and one of B¹, B², B³ and B⁴ is a carbon directly bonded to the nitrogen to R² is attached;

and each R⁶, each R⁷, each R⁸, each R⁹, each R¹⁰, each R¹¹, each R¹² and each R¹³ is as defined above for the compounds of formula (Ia).

Another embodiment is wherein the compound of formula (I) is a compound of formula (Ia), as set forth above, wherein:
R¹, R⁴ and R⁵ are each hydrogen;
R² is a bridged bicyclic heteroaryl of formula (III):

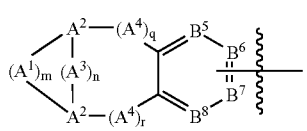

(III)

where:
m and n are independently 1 to 2;
q and r are independently 0 to 2;
each A¹, A³ and A⁵ is independently selected from the group consisting of C(R⁸)₂, O, S(O)$_p$ (where p is 0, 1 or 2), P(O)$_p$ (where p is 0, 1 or 2) and N(R⁹);
each A² is independently selected from the group consisting of C(R⁸) and N;
B⁵, B⁶, B⁷ and B⁸ are each independently selected from the group consisting of =C(R¹³)— and =N—, provided that at least one of A¹, A³ and A⁴ is independently selected from the group consisting of O, S(O)$_p$ (where p is 0, 1 or 2), P(O)$_p$ (where p is 0, 1 or 2) and N(R⁹), or A² is =N— or one of B⁵, B⁶, B⁷ and B⁸ is =N—, and one of B⁵, B⁶, B⁷ and B⁸ is a carbon directly bonded to the nitrogen to which R³ is attached; and R³ is a bicyclic aryl of formula (II):

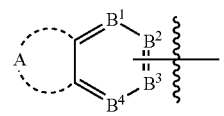

(II)

where:
A is an alkylene chain containing six carbons, an alkenylene chain containing six carbons, or an alkynylene chain containing six carbons, where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R⁶, —R¹⁰—OR⁹, —R¹⁰—O—R¹¹—OR⁹, —R¹⁰—O—R¹¹—O—R¹¹—OR⁹, —R¹⁰—O—R¹¹—CN, —R¹⁰—O—R¹¹—C(O)OR⁹, —R¹⁰—O—R¹¹—C(O)N(R⁶)R⁷, —R¹⁰—O—R¹¹—S(O)$_p$R⁹ (where p is 0, 1 or 2), —R¹⁰—O—R¹¹—N(R⁶)R⁷, —R¹⁰—O—R¹¹—C(NR¹²)N(R¹²)H, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁹, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2); and B¹, B², B³ and B⁴ are each independently =C(R¹³)—, provided that one of B¹, B², B³ and B⁴ is a carbon directly bonded to the nitrogen to which R³ is attached;

and each R⁶, each R⁷, each R⁸, each R⁹, each R¹⁰, each R¹¹, each R¹² and each R¹³ is as defined above for the compounds of formula (Ia).

Another embodiment is wherein the compound of formula (I) is a compound of formula (Ia), as set forth above, wherein:
R¹, R⁴ and R⁵ are each hydrogen;
R² is a bridged bicyclic heteroaryl of formula (III):

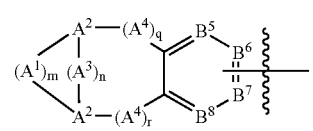

(III)

where:
m and n are independently 1 to 2;
q and r are independently 0 to 2;
each A¹, A³ and A⁴ is independently selected from the group consisting of C(R⁸)₂, O, S(O)$_p$ (where p is 0, 1 or 2), P(O)$_p$ (where p is 0, 1 or 2) and N(R⁹);
each A² is independently selected from the group consisting of C(R⁸) and N;
B⁵, B⁶, B⁷ and B⁸ are each independently selected from the group consisting of =C(R¹³)— and =N—, provided that at least one of A¹, A³ and A⁴ is independently selected from the group consisting of O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached; and R$^3$ is a bicyclic aryl of formula (II):

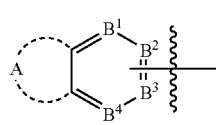

(II)

where:

A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^3$ is attached; and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bridged bicyclic heteroaryl of formula (III):

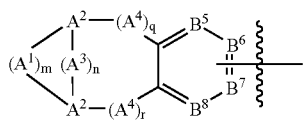

(III)

where:

m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that at least one of A$^1$, A$^3$ and A$^4$ is independently selected from the group consisting of O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached; and R$^3$ is a bicyclic heteroaryl of formula (II):

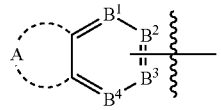

(II)

where:

A is an alkylene chain containing six carbons, an alkenylene chain containing six carbons, or an alkynylene chain containing six carbons, where each carbon of the alkylene, alkenylene or alkynylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^3$ is attached;

and each R$^6$, each R$^7$, each R$^8$, each R$^9$, each R$^{10}$, each R$^{11}$, each R$^{12}$ and each R$^{13}$ is as defined above for the compounds of formula (Ia).

Another embodiment is wherein the compound of formula (I) is a compound of formula (Ia), as set forth above, wherein:
R$^1$, R$^4$ and R$^5$ are each hydrogen;
R$^2$ is a bridged bicyclic heteroaryl of formula (III):

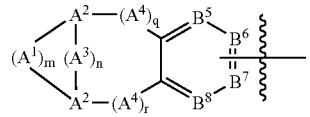

(III)

where:

m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached; and $R^3$ is a bicyclic heteroaryl of formula (II):

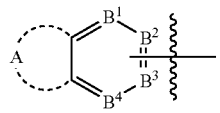
(II)

where:
A is an alkylene chain containing six carbons, where each carbon of the alkylene chain may be replaced by —$N(R^9)$—, =N—, —O—, —$S(O)_p$— (where p is 0, 1 or 2) or —$P(O)_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—OC(O)—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and $B^1$, $B^2$, $B^3$ and $B^4$ are each independently selected from the group consisting of =$C(R^{13})$— and =N—, provided that at least one carbon in A is replaced with —$N(R^9)$—, =N—, —O—, —$S(O)_p$— (where p is 0, 1 or 2) or —$P(O)_p$— (where p is 0, 1 or 2) or one of $B^1$, $B^2$, $B^3$ and $B^4$ is =N—, and one of $B^1$, $B^2$, $B^3$ and $B^4$ is a carbon directly bonded to the nitrogen to $R^2$ is attached;

and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III) or a bridged bicyclic heteroaryl of formula (III):

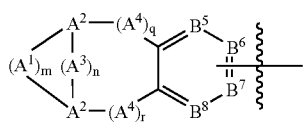
(III)

where:
m and n are independently 1 to 2;
q and r are independently 0 to 3;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of $C(R^8)$ and N;

$B^5$, $B^6$, $B^7$ and $B^8$ are each independently selected from the group consisting of =$C(R^{13})$— and =N—, provided that one of $B^5$, $B^6$, $B^7$ and $B^8$ is a carbon directly bonded to the nitrogen to which $R^2$ is attached; and $R^3$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—OC(O)—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2);

and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III):

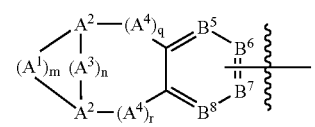
(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently =$C(R^{13})$—, provided that one of $B^5$, $B^6$, $B^7$ and $B^8$ is a carbon directly bonded to the nitrogen to which $R^2$ is attached; and $R^3$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—OC(O)—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2);
and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic aryl of formula (III):

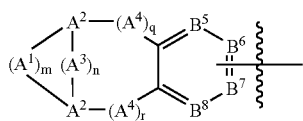

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently $=C(R^{13})-$, provided that one of $B^5$, $B^6$, $B^7$ and $B^8$ is a carbon directly bonded to the nitrogen to which $R^2$ is attached; and
$R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, $-R^{10}-OR^9$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2);
and each $R^6$, each $R^7$, each $R^8$, each $R^9$, each $R^{10}$, each $R^{11}$, each $R^{12}$ and each $R^{13}$ is as defined above for the compounds of formula (Ia).

Of this embodiment, a preferred embodiment is a compound of formula (Ia) wherein:
$R^1$, $R^4$ and $R^5$ are each hydrogen;
$R^2$ is a bridged bicyclic aryl of formula (III):

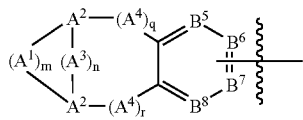

(III)

where:
m is 1 and n is 2;
q and r are each 1;
$A^1$ is $C(R^8)_2$;
each $A^3$ is $C(H)_2$;
each $A^4$ is $C(H)_2$;
each $A^2$ is independently $C(H)$;
$B^5$, $B^7$ and $B^8$ are each independently $=C(R^{13})-$ and $B^6$ is a carbon directly bonded to the nitrogen to which $R^2$ is attached; and
$R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl and alkyl;
and each $R^6$, each $R^7$, each $R^8$, each $R^9$, each $R^{10}$, each $R^{11}$, each $R^{12}$ and each $R^{13}$ is as defined above for the compounds of formula (Ia).

Of this embodiment, a preferred embodiment is the compound of formula (Ia) which is 1-(6,7-dihydro-5H-benzo[6,7]cyclohepta[1,2-c]pyridazin-3-yl)-$N^3$-(7-pyrrolidin-1-yl-6,8-ethano-6,7,8,9-tetrahydro-5H-benzo[7]annulene-3-yl)-1H-1,2,4-triazole-3,5-diamine.

Another embodiment is wherein the compound of formula (I) is a compound of formula (Ia), as set forth above, wherein:
$R^1$, $R^4$ and $R^5$ are each hydrogen;
$R^2$ is a bridged bicyclic heteroaryl of formula (III):

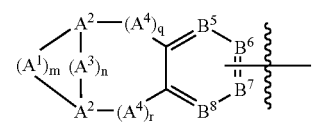

(III)

where:
m and n are independently 1 to 2;
q and r are independently 0 to 2;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of $C(R^8)$ and N;
$B^5$, $B^6$, $B^7$ and $B^8$ are each independently selected from the group consisting of $=C(R^{13})-$ and $=N-$, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is $=N-$ or one of $B^5$, $B^6$, $B^7$ and $B^8$ is $=N-$, and one of $B^5$, $B^6$, $B^7$ and $B^8$ is a carbon directly bonded to the nitrogen to which $R^3$ is attached; and
$R^3$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{10}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and each $R^6$, each $R^7$, each $R^8$, each $R^9$, each $R^{10}$, each $R^{11}$, each $R^{12}$ and each $R^{13}$ is as defined above for the compounds of formula (Ia).

Another embodiment is wherein the compound of formula (I) is a compound of formula (Ia), as set forth above, wherein:
$R^1$, $R^4$ and $R^5$ are each hydrogen;
$R^2$ is a bridged bicyclic heteroaryl of formula (III):

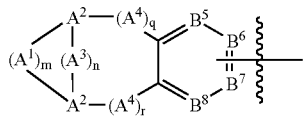

(III)

where:
m and n are independently 1 to 2;
q and r are independently 0 to 2;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of $C(R^8)$ and N;
$B^5$, $B^6$, $B^7$ and $B^8$ are each independently selected from the group consisting of =$C(R^{13})$— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached; and
$R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2).

Another embodiment of the compounds of formula (I), as set forth above in the Summary of the Invention, is wherein the compound of formula (I) is a compound of formula (Ib):

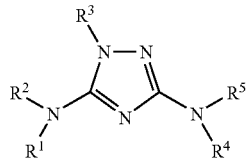

(Ib)

wherein:
$R^1$, $R^4$ and $R^5$ are independently selected from hydrogen, alkyl, aryl, aralkyl, —$C(O)R^9$ or —$C(O)N(R^6)R^7$;
one of $R^2$ and $R^3$ is selected from one of the following and the other is selected from the other two of the following:
a) a bicyclic aryl of formula (II) or a bicyclic heteroaryl of formula (II):

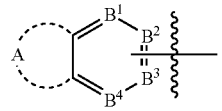

(II)

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by —$NR^9$—, =N—, —O—, —$S(O)_p$— (where p is 0, 1 or 2) or —$P(O)_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —R—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and
$B^1$, $B^2$, $B^3$ and $B^4$ are each independently selected from the group consisting of =$C(R^{13})$— and =N—, provided that one of $B^1$, $B^2$, $B^3$ and $B^4$ is a carbon directly bonded to the nitrogen to which its corresponding $R^2$ or $R^3$ is attached;

b) a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); or c) a bridged bicyclic aryl of formula (III) or a bridged bicyclic heteroaryl of formula (III):

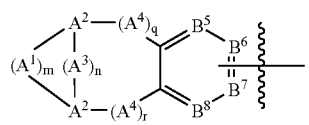

(III)

where:
m and n are independently 1 to 4;
q and r are independently 0 to 3;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$)$_p$;
each $A^2$ is independently selected from the group consisting of C($R^8$) and N;
$B^5$, $B^6$, $B^7$ and $B^8$ are each independently selected from the group consisting of =C($R^{13}$)— and =N—, provided that one of $B^5$, $B^6$, $B^7$ and $B^8$ is a carbon directly bonded to the nitrogen to which its corresponding $R^2$ or $R^3$ is attached;
each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{11}$—$OR^9$, —$R^{11}$—CN, —$R^{11}$—NO$_2$, —$R^{11}$—N($R^9$)$_2$, —$R^{11}$—C(O)$OR^9$ and —$R^{11}$—C(O)N($R^9$)$_2$, or any $R^6$ and $R^7$, together with the common nitrogen to which they are both attached, form an optionally substituted N-heteroaryl or an optionally substituted N-heterocyclyl;
each $R^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2), or two $R^8$'s on adjacent carbons can combine to form a double bond;

each $R^9$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl;

each $R^{10}$ is independently selected from the group consisting of a direct bond, an optionally substituted straight or branched alkylene chain, an optionally substituted straight or branched alkenylene chain and an optionally substituted straight or branched alkynylene chain;

each $R^{11}$ is independently selected from the group consisting of an optionally substituted straight or branched alkylene chain, an optionally substituted straight or branched alkenylene chain and an optionally substituted straight or branched alkynylene chain;

each $R^{12}$ is hydrogen, alkyl, cyano, nitro or —$OR^9$; and each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t$$R^9$ (where t is 1 or 2), —$R^{10}$—S(O)$_t$$OR^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2);

as an isolated stereoisomer or a mixture thereof, or as a pharmaceutically acceptable salt thereof.

Another embodiment is wherein the compound of formula (I) is a compound of formula (Ib), as set forth above, wherein:
$R^1$, $R^4$ and $R^5$ are each hydrogen;
$R^2$ is a bicyclic aryl of formula (II) or a bicyclic heteroaryl of formula (II):

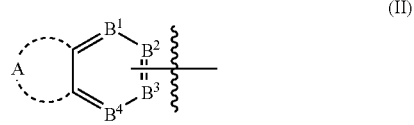

(II)

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by —NR$^9$—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to which its corresponding R$^2$ or R$^3$ is attached; and R$^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

Another embodiment is wherein the compound of formula (I) is a compound of formula (Ib), as set forth above, wherein:
R$^1$, R$^4$ and R$^5$ are each hydrogen;
R$^2$ is a bicyclic heteroaryl of formula (II):

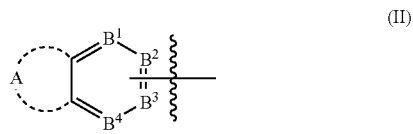

(II)

where:
A is an alkylene chain containing six carbons, an alkenylene chain containing six carbons, or an alkynylene chain containing six carbons, where each carbon of the alkylene, alkenylene or alkynylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to which R$^2$ is attached; and R$^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

Another embodiment is wherein the compound of formula (I) is a compound of formula (Ib), as set forth above, wherein:
R$^1$, R$^4$ and R$^5$ are each hydrogen;
R$^2$ is a bicyclic heteroaryl of formula (II):

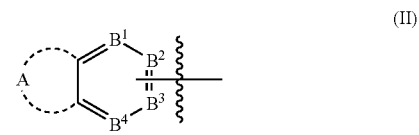

(II)

where:
A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— or =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

Another embodiment is wherein the compound of formula (I) is a compound of formula (Ib), as set forth above, wherein:
R$^1$, R$^4$ and R$^5$ are each hydrogen;
R$^2$ is a bicyclic heteroaryl of formula (II):

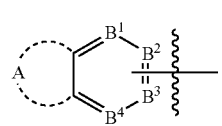

(II)

where:
A is an alkylene chain containing six carbons, where at least one carbon is replaced by —N(R$^9$)— and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

Another embodiment is wherein the compound of formula (I) is a compound of formula (Ib), as set forth above, which is 1-(6,7-dihydro-5H-benzo[6,7]cyclohepta[1,2-c]pyridazin-3-yl)-N$^5$-(1(2H)-oxo-3,4,5,6-tetrahydrobenzo[c]azocin-9-yl)-1H-1,2,4-triazole-3,5-diamine.

Another embodiment is wherein the compound of formula (I) is a compound of formula (Ib), as set forth above, wherein:
R$^1$, R$^4$ and R$^5$ are each hydrogen;
R$^2$ is a bicyclic aryl of formula (II) or a bicyclic heteroaryl of formula (II):

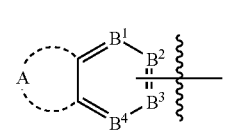

(II)

where:
A is an alkylene chain containing six to ten carbons, an alkenylene chain containing six to ten carbons, or an alkynylene chain containing six to ten carbons, where one or two carbons of the alkylene, alkenylene or alkynylene chain is optionally replaced by —NR$^9$—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to R$^2$ is attached; and R$^3$ is a bridged bicyclic aryl of formula (III) or a bridged bicyclic heteroaryl of formula (III):

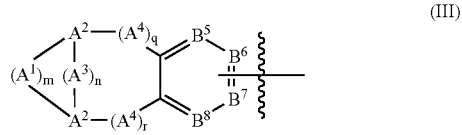

(III)

where:
m and n are independently 1 to 2;
q and r are independently 0 to 3;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that one of B$^5$, B$^6$, B$^7$ and B$^8$ is a carbon directly bonded to the nitrogen to which R$^3$ is attached.

Another embodiment is wherein the compound of formula (I) is a compound of formula (Ib), as set forth above, wherein:
R$^1$, R$^4$ and R$^5$ are each hydrogen;
R$^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bicyclic aryl of formula (II) or a bicyclic heteroaryl of formula (II):

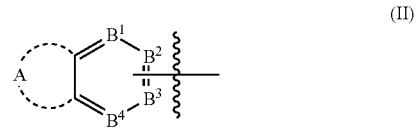

(II)

where:
A is an alkylene chain containing six to ten carbons, an alkenylene chain containing six to ten carbons, or an alkynylene chain containing six to ten carbons, where each carbon of the alkylene, alkenylene or alkynylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to which R$^3$ is attached.

Another embodiment is wherein the compound of formula (I) is a compound of formula (Ib), as set forth above, wherein:
R$^1$, R$^4$ and R$^5$ are each hydrogen;
R$^2$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and $R^3$ is a bridged bicyclic aryl of formula (III) or a bridged bicyclic heteroaryl of formula (III):

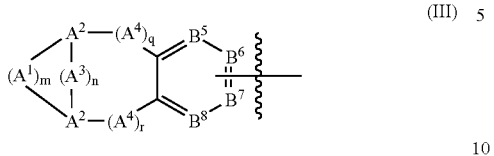

(III)

where:
  m and n are independently 1 to 2;
  q and r are independently 0 to 3;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ or N;
  $B^5$, $B^6$, $B^7$ and $B^8$ are each independently $=C(R^{13})-$ or $=N-$, provided that one of $B^5$, $B^6$, $B^7$ and $B^8$ is a carbon directly bonded to the nitrogen to which $R^3$ is attached.

Another embodiment is wherein the compound of formula (I) is a compound of formula (Ib), as set forth above, wherein:
$R^1$, $R^4$ and $R^5$ are each hydrogen;
$R^2$ is a bridged bicyclic aryl of formula (III) or a bridged bicyclic heteroaryl of formula (III):

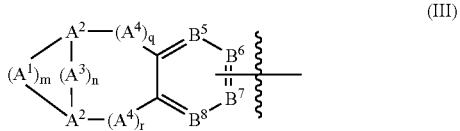

(III)

where:
  m and n are independently 1 to 2;
  q and r are independently 0 to 3;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ and N;
  $B^5$, $B^6$, $B^7$ and $B^8$ are each independently selected from the group consisting of $=C(R^{13})-$ and $=N-$, provided that one of $B^5$, $B^6$, $B^7$ and $B^8$ is a carbon directly bonded to the nitrogen to which $R^2$ is attached; and
$R^3$ is a bicyclic aryl of formula (II) or a bicyclic heteroaryl of formula (II):

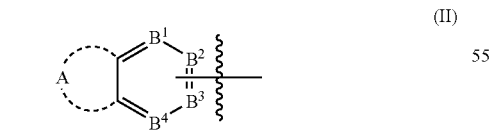

(II)

where:
  A is an alkylene chain containing six to ten carbons, an alkenylene chain containing six to ten carbons, or an alkynylene chain containing six to ten carbons, where each carbon of the alkylene, alkenylene or alkynylene chain may be replaced by $-N(R^9)-$, $=N-$, $-O-$, $-S(O)_p-$ (where p is 0, 1 or 2) or $-P(O)_p-$ (where p is 0, 1 or 2) and where each carbon in the alkylene chain, the alkenylene chain or the alkynylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and
$B^1$, $B^2$, $B^3$ and $B^4$ are each independently selected from the group consisting of $=C(R^{13})-$ and $=N-$, provided that one of $B^1$, $B^2$, $B^3$ and $B^4$ is a carbon directly bonded to the nitrogen to which $R^3$ is attached.

Another embodiment is wherein the compound of formula (I) is a compound of formula (Ib), as set forth above, wherein:
$R^1$, $R^4$ and $R^5$ are each hydrogen;
$R^2$ is a bridged bicyclic aryl of formula (III) or a bridged bicyclic heteroaryl of formula (III):

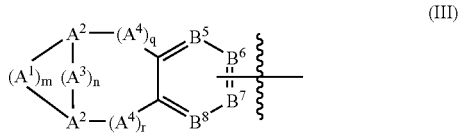

(III)

where:
  m and n are independently 1 to 2;
  q and r are independently 0 to 3;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ and N;
  $B^5$, $B^6$, $B^7$ and $B^8$ are each independently selected from the group consisting of $=C(R^{13})-$ and $=N-$, provided that one of $B^5$, $B^6$, $B^7$ and $B^8$ is a carbon directly bonded to the nitrogen to which $R^2$ is attached; and
$R^3$ is a polycyclic heteroaryl containing more than 14 ring atoms optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2).

Additional preferred embodiments of $R^1$, $R^2$, $R^3$, $R^4$ and $R^5$ of the compounds of formula (Ib) are the same as set forth above for $R^1$, $R^2$, $R^3$, $R^4$ and $R^5$ of the compounds of formula (Ia).

Of the polycyclic heteroaryl containing more than 14 ring atoms for $R^2$ and $R^3$, preferred embodiments are selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted as described herein for polycyclic heteroaryls containing more than 14 ring atoms.

In any of the above embodiments, certain embodiments for the choices described in the Summary of the Invention for each $R^6$, $R^7$, $R^8$, $R^9$, $R^{10}$, $R^{11}$ and $R^{13}$ are preferred.

Of the choices for each $R^6$ and $R^7$, as set forth above in the Summary of the Invention, one preferred embodiment is where each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $—R^{11}—OR^9$, $—R^{11}—CN$, $—R^{11}—NO_2$, $—R^{11}—N(R^9)_2$, $—R^{11}—C(O)OR^9$ and $—R^{11}—C(O)N(R^9)_2$.

Another preferred embodiment is where any $R^6$ and $R^7$, together with the common nitrogen to which they are both attached, form an optionally substituted N-heteroaryl or an optionally substituted N-heterocyclyl.

Another preferred embodiment is where each $R^8$ and $R^7$ is independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $—R^{11}—OR^9$, $—R^{11}—CN$, $—R^{11}—NO_2$, $—R^{11}—N(R^9)_2$, $—R^{11}—C(O)OR^9$ and $—R^{11}—C(O)N(R^9)_2$, Another preferred embodiment is where each $R^6$ and $R^7$ is independently selected from the group consisting of hydrogen, alkyl, haloalkyl, hydroxyalkyl, optionally substituted aryl, optionally substituted aralkyl, $—R^{11}—OR^9$, $—R^{11}—CN$, $—R^{11}—NO_2$, $—R^{11}—N(R^9)_2$, $—R^{11}—C(O)OR^9$ and $—R^{11}—C(O)N(R^9)_2$.

Another preferred embodiment is where each $R^6$ and $R^7$ is independently selected from the group consisting of hydrogen, alkyl, haloalkyl, hydroxyalkyl, optionally substituted aryl, and optionally substituted aralkyl.

Of the choices for each $R^8$, as set forth above in the Summary of the Invention, one preferred embodiment is where each $R^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, and optionally substituted heterocyclylalkyl.

Another preferred embodiment is where each $R^8$ is independently selected from the group consisting of, $—R^{10}—OR^9$, $—R^{10}—OC(O)—R^9$, $—R^{10}—N(R^6)R^7$, $—R^{10}—C(O)R^9$, $—R^{10}—C(O)OR^9$, $—R^{10}—C(O)N(R^6)R^7$, $—R^{10}—N(R^6)C(O)OR^9$, $—R^{10}—N(R^6)C(O)R^9$, $—R^{10}—N(R^6)S(O)_tR^9$ (where t is 1 or 2), $—R^{10}—S(O)_tOR^9$ (where t is 1 or 2), $—R^{10}—S(O)_pR^9$ (where p is 0, 1 or 2), and $—R^{10}—S(O)_tN(R^6)R^7$ (where t is 1 or 2).

Another preferred embodiment is where two $R^8$'s on adjacent carbons can combine to form a double bond.

Of the choices for each $R^9$, as set forth above in the Summary of the Invention, one preferred embodiment is where each $R^9$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl.

Of the choices for $R^{10}$, as set forth above in the Summary of the Invention, one preferred embodiment is where each $R^{10}$ is independently selected from the group consisting of a direct bond and an optionally substituted straight or branched alkylene chain.

Of the choices for $R^{11}$, as set forth above in the Summary of the Invention, one preferred embodiment is where each $R^{11}$ is an optionally substituted straight or branched alkylene chain.

Of the choices for each $R^{13}$, as set forth above in the Summary of the Invention, one preferred embodiment is where each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl.

Another preferred embodiment is where each $R^{13}$ is independently selected from the group consisting of hydrogen, halo, haloalkyl, alkyl, optionally substituted aryl and optionally substituted aralkyl.

Another preferred embodiment is where each $R^{13}$ is independently selected from the group consisting of $—R^{10}—OR^9$, $—R^{10}—OC(O)—R^9$, $—R^{10}—N(R^6)R^7$, $—R^{10}—C(O)R^9$, $—R^{10}—C(O)OR^9$, $—R^{10}—C(O)N(R^6)R^7$, $—R^{10}—N(R^6)C(O)OR^9$, $—R^{10}—N(R^6)C(O)R^9$, $—R^{10}—N(R^6)S(O)_tR^9$ (where t is 1 or 2), $—R^{10}—S(O)_tOR^9$ (where t is 1 or 2), $—R^{10}—S(O)_pR^9$ (where p is 0, 1 or 2), and $—R^{10}—S(O)_tN(R^6)R^7$ (where t is 1 or 2).

In a particular embodiment, in compounds of formula (Ia), $R^3$ is a bridged bicyclic heteroaryl of formula (IIIc):

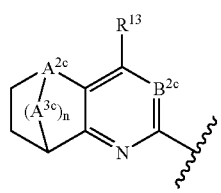

(IIIc)

where:
n is 1 to 2;
$A^{3c}$ is $C(R^8)_2$;
$A^{2c}$ is $C(R^8)$ or N;
$B^{2c}$ is N or CH;
each $R^6$ and $R^7$ is independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^{11}$—$OR^9$, —$R^{11}$—CN, —$R^{11}$—$NO_2$, —$R^{11}$—N$(R^9)_2$, —$R^{11}$—C(O)$OR^9$ and —$R^{11}$—C(O)N$(R^9)_2$, or any $R^6$ and $R^7$, together with the common nitrogen to which they are both attached, form an optionally substituted N-heteroaryl or an optionally substituted N-heterocyclyl;
each $R^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2), or two $R^8$'s on adjacent carbons can combine to form a double bond;
each $R^9$ is independently selected from the group consisting of hydrogen, alkyl, alkenyl, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;
each $R^{10}$ is independently selected from the group consisting of a direct bond and an optionally substituted straight or branched alkylene chain;
each $R^{11}$ is an optionally substituted straight or branched alkylene chain; and
$R^{13}$ is selected from the group consisting of optionally substituted aryl and optionally substituted heteroaryl.

Exemplary $R^3$ groups of formula (IIIc) include, but are not limited to, optionally substituted 1,4-ethano-1,2,3,4-tetrahydro-1,5-naphthyridin-6-yl, optionally substituted 5,8-methano-5,6,7,8-tetrahydroquinolin-2-yl, and optionally substituted 5,8-methano-5,6,7,8-tetrahydroquinazolin-2-yl. In one embodiment of this aspect of the invention, $R^{13}$ is selected from the group consisting of phenyl, furanyl, thienyl, pyridinyl, pyrazinyl, and pyridazinyl, each optionally substituted.

In a particular embodiment, in compounds of formula (Ia), $R^3$ is a bridged bicyclic heteroaryl of formula (IIId):

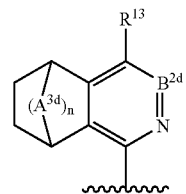

(IIId)

where:
n is 1 to 2;
$A^{2d}$ is $C(R^8)$;
$B^{2d}$ is N or CH;
each $R^6$ and $R^7$ is independently selected from the group consisting of hydrogen, alkyl, haloalkyl, hydroxyalkyl, optionally substituted aryl, optionally substituted aralkyl, optionally substituted cycloalkyl, optionally substituted cycloalkylalkyl, optionally optionally substituted heterocyclyl, optionally substituted heterocyclylalkyl, optionally substituted heteroaryl, optionally substituted heteroarylalkyl, —$R^{11}$—$OR^9$, —$R^{11}$—CN, —$R^{11}$—$NO_2$, —$R^{11}$—N$(R^9)_2$, —$R^{11}$—C(O)$OR^9$ and —$R^{11}$—C(O)N$(R^9)_2$, or any $R^6$ and $R^7$, together with the common nitrogen to which they are both attached, form an optionally substituted N-heteroaryl or an optionally substituted N-heterocyclyl;
each $R^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2), or two $R^8$'s on adjacent carbons can combine to form a double bond;
each $R^9$ is independently selected from the group consisting of hydrogen, alkyl, alkenyl, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;
each $R^{10}$ is independently selected from the group consisting of a direct bond and an optionally substituted straight or branched alkylene chain;
each $R^{11}$ is an optionally substituted straight or branched alkylene chain; and
$R^{13}$ is selected from the group consisting of optionally substituted aryl and optionally substituted heteroaryl.

An exemplary $R^3$ group of formula (IIId) is optionally substituted 5,8-methano-5,6,7,8-tetrahydrophthalazine-4-yl. In one embodiment of this aspect of the invention, $R^{13}$ is selected from the group consisting of phenyl, furanyl, thienyl, pyridinyl, pyrazinyl, and pyridazinyl, each optionally substituted.

Of the various aspects of the pharmaceutical compositions of the invention comprising a pharmaceutically acceptable excipient and a therapeutically effective amount of a compound of formula (I), as set forth above in the Summary of the Invention, certain embodiments are preferred.

One embodiment of these pharmaceutical compositions is wherein the compound of formula (I) therein is selected from any one embodiment of the compound of formula (Ia), as set forth above, or from any combination of embodiments of the compound of formula (Ia), as set forth above, or the compound of formula (I) therein is selected from any one embodiment of the compound of formula (Ib), as set forth above, or from any combination of embodiments of the compound of formula (Ib), as set forth above.

Of the various aspects of methods of treating a disease or condition associated with Axl activity in a mammal, wherein the method comprises administering to a mammal in need thereof a therapeutically effective amount of a compound of formula (I), as set forth above in the Summary of the Invention, certain embodiments are preferred.

One embodiment of these methods is the method wherein the disease or condition is selected from the group consisting of rheumatoid arthritis, vascular disease, vascular injury, psoriasis, visual impairment due to macular degeneration, diabetic retinopathy, retinopathy of prematurity, kidney disease, osteoporosis, osteoarthritis and cataracts.

One embodiment of these methods is the method wherein a manifestation of the disease or condition is solid tumor formation in said mammal.

One embodiment of these methods is the method wherein the disease or condition is selected from the group consisting of breast carcinoma, renal carcinoma, endometrial carcinoma, ovarian carcinoma, thyroid carcinoma, non-small cell lung carcinoma, and uveal melanoma.

One embodiment of these methods is the method wherein a manifestation of the disease or condition is liquid tumor formation in said mammal.

One embodiment of these methods is the method wherein the disease or condition is myeloid leukemia or lymphoma.

One embodiment of these methods is the method wherein the disease or condition is endometriosis.

One embodiment of these methods is the method wherein the compounds of formula (I) utilized therein is selected from any one embodiment of the compound of formula (Ia), as set forth above, or from any combination of embodiments of the compound of formula (Ia), as set forth above, or the compound of formula (I) therein is selected from any one embodiment of the compound of formula (Ib), as set forth above, or from any combination of embodiments of the compound of formula (Ib), as set forth above.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of rheumatoid arthritis, vascular disease/injury (including but not limited to restenosis, atherosclerosis and thrombosis), psoriasis, visual impairment due to macular degeneration, diabetic retinopathy or retinopathy of prematurity, kidney disease (including but not limited to glomerulonephritis, diabetic nephropathy and renal transplant rejection), osteoporosis, osteoarthritis and cataracts.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of breast carcinoma, renal carcinoma, endometrial carcinoma, ovarian carcinoma, thyroid carcinoma, non-small cell lung carcinoma, melanoma, prostate carcinoma, sarcoma, gastric cancer, uveal melanoma, myeloid leukemia and lymphoma.

Another embodiment of the invention are those methods of treating a disease or condition associated with Axl activity by administering to the mammal of therapeutically effective amount of a pharmaceutical composition of the invention, as set forth above in the Summary of the Invention, wherein the disease or condition is endometriosis.

It is understood that any embodiment of the compounds of formula (I), as set forth above, and any specific substituent set forth herein for a $R^1$, $R^2$, $R^3$, $R^4$ and $R^5$ group in the compounds of formula (I), as set forth above, may be independently combined with other embodiments and/or substituents of compounds of formula (I) to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention.

Specific embodiments of the invention are described in more detail below in the following sections.

Utility and Testing of the Compounds of the Invention

The oncogenic RTK, Axl, was recently identified, using a retroviral-based functional genetic screening protocol, as a regulator of haptotactic migration, which is a key event in angiogenesis. Axl inhibition by RNAi-mediated silencing blocked endothelial cell migration, proliferation and in vitro tube formation. These observations, which were disclosed at the American Association Cancer Research General Meeting, Apr. 16-20, 2005, Anaheim, Calif., and The 7th Annual Symposium on Anti-Angiogenic Agents, Feb. 10-13, 2005, San Diego, Calif.; (*Requirement for The Receptor Tyrosine Kinase Axl in Angiogenesis and Tumor Growth*, Holland, S. J. Powell, M. J., Franci, C., Chan, E., Friera, A. M., Atchison, R., Xu, W., McLaughlin, J., Swift, S. E., Pali, E., Yam, G., Wong, S., Xu, X., Hu, Y., Lasaga, J., Shen, M., Yu, S., Daniel, R., Hitoshi, Y., Bogenberger, J., Nor, J. E., Payan, D. G and Lorens, J. B), were substantiated by an in vivo study which demonstrated that stable, shRNAi-mediated Axl knockdown impaired formation of functional human blood vessels in a mouse model of human angiogenesis. These observations were published in a peer reviewed journal (Holland S J, Powell M J, Franci C, Chan E W, Friera A M, Atchison R E, McLaughlin J, Swift S E, Pali E S, Yam G, Wong S, Lasaga J, Shen M R, Yu S, Xu W, Hitoshi Y, Bogenberger J, Nor J E, Payan D G, Lorens J B. "Multiple roles for the receptor tyrosine kinase axl in tumor formation." *Cancer Res*. (2005) Vol 65 pp 9294-303. These observations are also disclosed in U.S. Published Patent Application 2005/0118604 and European Patent Application 1 563 094, the disclosures of which are incorporated in full by reference. Axl signaling, therefore, impacts multiple functions required for neovascularization in vitro, and regulates angiogenesis in vivo. Regulation of these pro-angiogenic processes required the catalytic activity of Axl. Thus, Axl-mediated angiogenic stimulation would be amenable to modulation by a small molecule inhibitor of Axl catalytic activity.

Accordingly, the compounds of the invention are small molecule inhibitors of Axl catalytic activity, and are therefore useful in treating diseases and conditions which are associated with Axl catalytic activity including those diseases and conditions which are characterized by angiogenesis and/or cell proliferation. In particular, the compounds of the invention and pharmaceutical compositions of the invention are useful in treating diseases and conditions which are alleviated by the modulation of Axl activity. For purposes of this invention, diseases and conditions which are alleviated by the "modulation of Axl activity" includes diseases and conditions which are alleviated by a decrease in Axl activity and diseases and conditions which are alleviated by an increase in Axl activity. Preferably such diseases and conditions are alleviated by a decrease in Axl activity. Diseases and conditions which are alleviated by the modulation of Axl activity include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis, osteoporosis and cataracts.

In addition to the foregoing, the compounds of the invention are useful in treating diseases and conditions which are affected by the following biological processes: Invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostasis as manifested in osteoporosis or osteoarthritis; viral infection as manifested, for example, in ebola virus infection; or differentiation as manifested in obesity. The compounds of the invention may also be used to modulate inflammatory processes by treating sepsis, acting as vaccine adjuvants, and/or potentiating the immune response in immuno-compromised patients.

The following animal models provide guidance to one of ordinary skill in the art in testing the compounds of the invention for their use in treating the disease or condition indicated.

The compounds of the invention may be tested for their use in treating leukemias and lymphomas by testing the compounds in the xenograft in SCID mouse model using human Axl-expressing cancer cell lines including, but not limited to, HeLa, MDA-MB-231, SK-OV-3, OVCAR-8, DU145, H1299, ACHN, A498 and Caki-1.

The compounds of the invention may be tested for their use in treating leukemias in the xenograft in SCID or nu/nu mouse model using human Axl-expressing AML and CML leukemia cell lines.

The compounds of the invention may be tested for their use in treating endometriosis by using the syngenic mouse model of endometriosis (see Somigliana, E. et al., "Endometrial ability to implant in ectopic sites can be prevented by interleukin-12 in a murine model of endometriosis", *Hum. Reprod*. (1999), Vol. 14, NO. 12, pp. 2944-50). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", *Fertil. Steril*. (2004), 82 Suppl 3, pp. 1008-13).

The compounds of the invention may be tested for their use in treating restenosis by using the balloon-injured rate carotid artery model (see Kim, D. W. et al., "Novel oral formulation of paclitaxel inhibits neointimal hyperplasia in a rat carotid artery injury model", *Circulation* (2004), Vol. 109, No. 12, pp. 1558-63, Epub Mar. 8, 2004).

The compounds of the invention may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", *Arterioscler. Thromb. Vasc. Biol*. (2004), Vol. 24, No. 2, pp. 357-62).

The compounds of the invention may be tested for their use in treating atherosclerosis/thrombosis in the ApoE deficient mouse model (see Nakashima, Y. et al., "ApoE-deficient mice develop lesions of all phases of atherosclerosis throughout the arterial tree", *Arterioscler. Thromb*. (1994), Vol. 14, No. 1, pp. 133-40).

The compounds of the invention may also be tested for their use in treating thrombosis using the collagen-epinephrin-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", *J Clin Invest*. (2005) Vol 115 pp 237-46).

The compounds of the invention may be tested for their use in treating psoriasis by using the SCID mouse model or the human skin model of psoriasis (see Nickoloff, B. J. et al., "Severe combined immunodeficiency mouse and human psoriatic skin chimeras. Validation of a new animal model", *Am. J. Pathol*. (1995), Vol. 146, No. 3, pp. 580-8).

The compounds of the invention may be tested for their use in treating age-related macular degeneration or diabetic retinopathy by using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. *Exp Eye Res*. 2005 March; 80(3):435-42) or the laser-induced mouse choroidal neovasculation model (see Bora, P. S., et al., "Immunotherapy for choroidal neovascularization in a laser-induced mouse model simulating exudative (wet) macular degeneration", *Proc. Natl. Acad. Sci. U.S.A*. (2003), Vol. 100, No. 5, pp. 2679-84, Epub Feb. 14, 2003).

The compounds of the invention may be tested for their use in treating retinopathy of prematurity in the mouse retinopathy of prematurity model (see Smith, L. E. et al., "Oxygen-induced retinopathy in the mouse", *Invest. Ophthalmol. Vis. Sci*. (1994), Vol. 35, No. 1, pp. 101-11).

The compounds of the invention may be tested for their use in treating glomerulonephritis or diabetic nephropathy in the rat anti-Thy1.1-induced experimental mesengial proliferative glomerulonephritis model (see Smith, L. E. et al. cited above).

The compounds of the invention may be tested for their use in treating renal transplant rejection by using a rat model of chronic renal transplant rejection (see Yin, J. L. et al., "Expression of growth arrest-specific gene 6 and its receptors in a rat model of chronic renal transplant rejection", *Transplantation* (2002), Vol. 73, No. 4, pp. 657-60).

The compounds of the invention may be tested for their use in treating rheumatoid arthritis by using the CAIA mouse model (see Phadke, K. et al., "Evaluation of the effects of various anti-arthritic drugs on type II collagen-induced mouse arthritis model", *Immunopharmacology* (1985), Vol. 10, No. 1, pp. 51-60).

The compounds of the invention may be tested for their use in treating osteoarthritis by using the STR/ORT mouse model (see Brewster, M. et al., "Ro 32-3555, an orally active collagenase selective inhibitor, prevents structural damage in the STR/ORT mouse model of osteoarthritis", *Arthritis. Rheum.* (1998), Vol. 41, No. 9, pp. 1639-44).

The compounds of the invention may be tested for their use in treating osteoporosis by using the ovariectomized rat model (see Wronski, T. J. et al., "Endocrine and pharmacological suppressors of bone turnover protect against osteopenia in ovariectomized rats", *Endocrinology* (1989), Vol. 125, no. 2, pp 810-6) or the ovariectomized mouse model (see Alexander, J. M. et al., "Human parathyroid hormone 1-34 reverses bone loss in ovariectomized mice", *J Bone Miner Res.* (2001), Vol. 16, no. 9, pp 1665-73; Fujioka, M. et al., "Equol, a metabolite of daidzein, inhibits bone loss in ovariectomized mice", *J Nutr.* (2004), Vol. 134, no. 10, pp 2623-7).

The compounds of the invention may be tested for their use in treating cataracts by using the $H_2O_2$-induced model (see Kadoya, K. et al., "Role of calpain in hydrogen peroxide induced cataract", *Curr. Eye Res.* (1993), Vol. 12, No. 4, pp. 341-6) or the Emory mouse model (see Sheets, N. L. et al., "Cataract- and lens-specific upregulation of ARK receptor tyrosine kinase in Emory mouse cataract", *Invest. Ophthalmol. Vis. Sci.* (2002), Vol. 43, No. 6, pp. 1870-5).

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.70 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation of the Compounds of the Invention

The following Reaction Scheme illustrates methods to make compounds of this invention, i.e., compounds of formula (I):

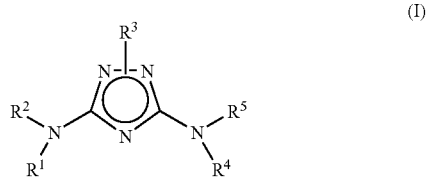

where $R^1$, $R^2$, $R^3$, $R^4$ and $R^5$ are described above in the Summary of the Invention for compounds of formula (I), as isolated stereoisomers or mixtures thereof, or as pharmaceutically acceptable salts thereof. In particular, the following Reaction Scheme illustrates methods to make compounds of formula (Ia):

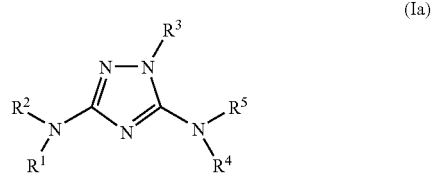

where $R^1$, $R^2$, $R^3$, $R^4$ and $R^5$ are as described above in the Summary of the Invention for compounds of formula (I), as isolated stereoisomers or mixtures thereof, or as pharmaceutically acceptable salts thereof, and methods to make compounds of formula (Ib);

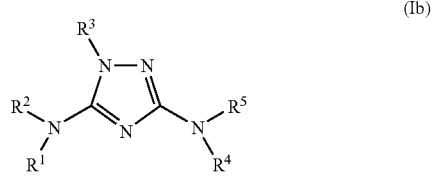

where $R^1$, $R^2$, $R^3$, $R^4$ and $R^5$ are as described above in the Summary of the Invention for compounds of formula (I), as isolated stereoisomers or mixtures thereof, or as pharmaceutically acceptable salts thereof. It is understood that in the following Reaction Schemes, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include benzyl, t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acids include alkyl, aryl or arylalkyl esters.

Protecting groups may be added or removed in accordance with standard techniques, which are known to one of ordinary skill in the art and as described herein.

The use of protecting groups is described in detail in Greene, T. W. and P. G. M. Wuts, *Greene's Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention. $^1$H NMR spectra were recorded in CDCl$_3$, DMSO-d$_6$, CD$_3$OD, Acetone-d$_6$ with trimethylsilane (TMS) as internal reference using Gemini 300 MHz instrument. Reagents and solvents were purchased from commercial sources and used without further purification. Flash column chromatography was conducted using silica gel (230-400 mesh) under a positive pressure of nitrogen. LCMS spectra for purity and mass were recorded using Waters LCMS instruments. Deionized water was used to dilute the reactions and wash the products. Brine used was prepared by dissolving sodium chloride into deionized water to saturation point.

Compounds of formula (Ia), as set forth below in Reaction Scheme 1 below, where $R^1$, $R^2$ and $R^3$ are defined above in the Summary of the Invention for compounds of formula (I) and $R^4$ and $R^5$ are hydrogen, are generally prepared as illustrated below in Reaction Scheme 1 where $R^1$, $R^2$ and $R^3$ are as defined above in the Summary of the Invention for compounds of formula (I):

REACTION SCHEME 1

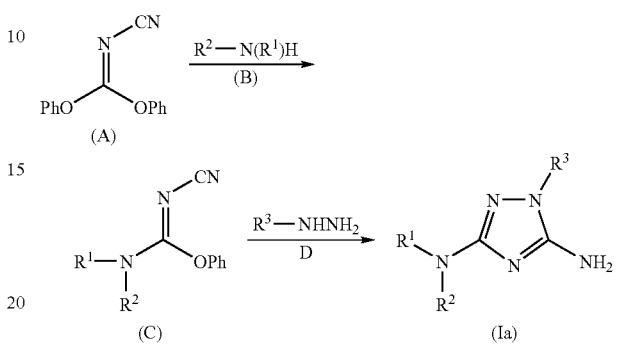

Compounds of formula (A), formula (B) and formula (D) are commercially available or can be prepared by methods known to one skilled in the art or by methods disclosed herein.

In general, compounds of formula (Ia) are prepared, as set forth by Reaction Scheme 1, by first treating a compound of formula (A) (1.1 equiv) with an equivalent amount of an aniline of formula (B) in an polar solvent, including, but not limited to, isopropyl alcohol, at ambient temperatures overnight. The diarylisourea product of formula (C) generally precipitates and isolation can be accomplished via filtration, washing with an appropriate solvent, and drying. Hydrazine hydrate of formula (D) (2 equivalents) is added to a slurry of the compound of formula (C) in an alcohol or other appropriate solvent. Generally, the ring formation reaction occurs at ambient temperature and the product triazole of formula (Ia) can be isolated by standard isolation techniques. Compounds of formula (Ia) can be subsequently treated with an appropriately substituted alkylating or acylating agent under standard conditions to form compounds of formula (Ia) where $R^4$ and $R^5$ are as described above in the Summary of the Invention for compounds of formula (I).

Compounds of formula (Ib) can be prepared using the synthetic route outlined in Reaction Scheme 1 in varying amounts depending on the steric and electronic nature of $R^1$, $R^2$ and $R^3$ as well as the particular reaction conditions employed. In some instances, compounds of formula (Ib) are isolated as minor isomers along with compounds of formula (Ia) as major isomers, e.g., during column chromatography as described herein.

Compounds of formula (C-1) are compounds of formula (C), as shown above in Reaction Scheme 1, where $R^1$ is hydrogen and $R^2$ is 5',5'-dimethyl-6,8,9,10-tetrahydro-5H-spiro[cycloocta[b]pyridine-7,2'-[1,3]dioxane]-3-yl, that is, where $R^2$ has the following structure:

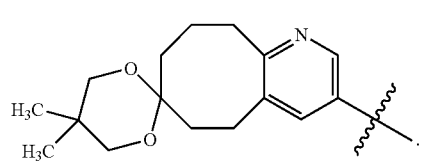

Compounds of formula (C-1) can be prepared according to the method described below in Reaction Scheme 2:

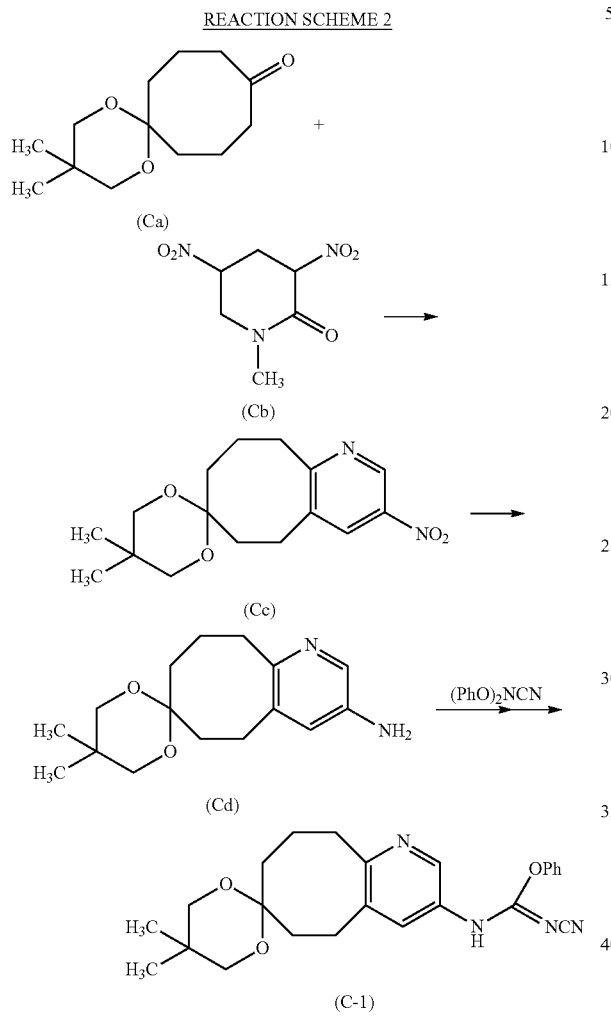

Compounds of formula (Ca) and (Cb) are commercially available or can be prepared according to methods known to one skilled in the art.

In general, compounds of formula (C-1) are prepared, as set forth above in Reaction Scheme 2, by first heating a mixture of the compound of formula (Ca) (1.0 equiv) and a compound of formula (Cb) (0.96 equiv) and ammonia in an protic solvent, such a methanol, to reflux temperature. The compound of formula (Cc) is then isolated from the reaction mixture by standard isolation techniques.

The compound of formula (Cc) is then reduced under standard reduction conditions known to one skilled in the art to yield the compound of formula (Cd).

A mixture of molar equivalent amounts of the compound of formula (Cd), diphenylcyanocarboimidate and diisopropylethylamine in a protic solvent, such as isopropyl alcohol, is stirred at ambient temperature for a period of time of between 8 hours and 16 hours, preferably for about 16 hours, to form the compound of formula (C-1), which is isolated from the reaction mixture by standard isolation techniques known to one skilled in the art.

Compounds of formula (Da) are compounds of formula (D), as shown above in Reaction Scheme 1, where $R^3$ is 6,7-dihydro-5H-benzo[6,7]cyclohepta[1,2-c]pyridazin-3-yl, that is, where $R^3$ has the following structure:

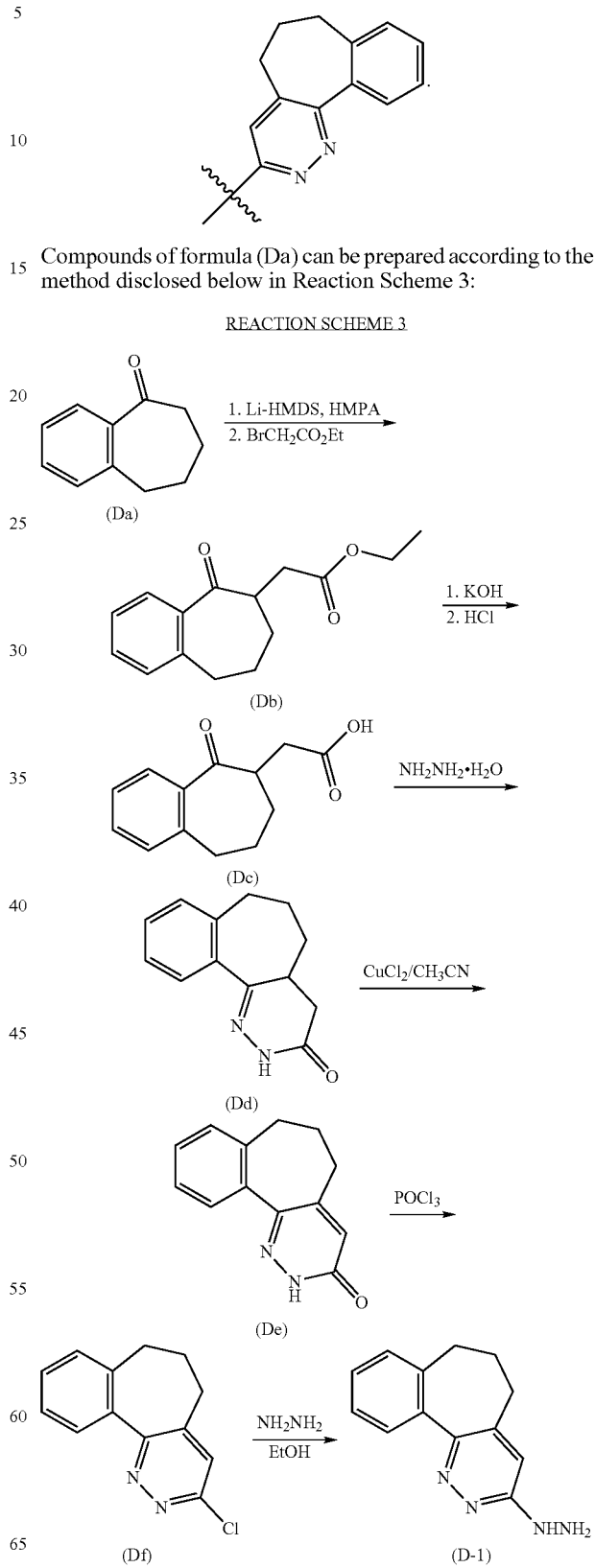

Compounds of formula (Da) can be prepared according to the method disclosed below in Reaction Scheme 3:

Compounds of formula (Da) are commercially available or can be prepared by methods known to one skilled in the art or by methods disclosed herein.

In general, compounds of formula (D-1) are prepared, as set forth above in Reaction Scheme 3, by first dissolving the compound of formula (Da) (1.0 equiv) in an anhydrous aprotic polar solvent or mixture of such solvents, for example, tetrahydrofuran with hexamethylphosphoramide (HMPA) (1.2 equiv). The resulting solution is stirred at ambient temperature for about 10 minutes and then cooled to a temperature of between about −10° C. and about 5° C., preferably at 0° C. A strong base, lithium bis(trimethylsilyl)amide (Li-HMDS) (1.1 equiv), is then added dropwise to the stirred mixture over a period of time of between about 20 minutes and 40 minutes, preferably over 30 minutes, while maintaining the temperature of the resulting mixture at between about −10° C. and about 5° C., preferably at 0° C. Ethyl bromoacetate (2.5 equiv) is then added to the resulting anion of (Da) and the resulting mixture is stirred for additional period of time of between about 5 minutes and 15 minutes, preferably for about 10 minutes, and then allowed to warm to ambient temperature and stirred at ambient temperature for a period of time of between about 30 minutes and 3 hours, preferably for about 2 hours. The compound of formula (Db) is then isolated from the reaction mixture by standard isolation techniques known to one skilled in the art, such as solvent evaporation and purification by flash column chromatography.

The compound of formula (Db) is then treated under basic hydrolysis conditions to form the compound of formula (Dc), which is isolated from the reaction mixture by standard isolation techniques known to one skilled in the art.

The compound of formula (Dc) (1.0 equiv) is then treated with hydrazine hydrate (1.25 equiv) in the presence of a polar protic solvent, such as ethanol, to yield the compound of formula (Dd), which is isolated from the reaction mixture by standard isolation techniques known to one skilled in the art.

A mixture of the compound of formula (Dd) (1.0 equiv) and anhydrous copper(II) chloride (2.0 equiv) is then refluxed in acetonitrile to yield the unsaturated compound of formula (De), which is isolated from the reaction mixture by standard isolation techniques known to one skilled in the art.

A mixture of the compound of formula (De) and phosphoryl chloride, is refluxed for a period of time of between about 1 hour and 3 hours, preferably for about 2 hours to aromatize and chlorinate the ring containing the N—N linkage. After cooling to ambient temperature, the compound of formula (Df) is isolated from the reaction mixture by standard isolation techniques known to one skilled in the art.

A mixture of the compound of formula (Df) (1.0 equiv) and anhydrous hydrazine (19.8 equiv) in a protic solvent, such as ethanol, is refluxed for a period time of between about 4 hours and 24 hours, preferably for about 16 hours. After cooling to ambient temperature, water is added to the mixture and the compound of formula (D-1) is then isolated from the reaction mixture by standard isolation techniques known to one skilled in the art Compounds of formula (D-2) are compounds of formula (D), as shown above in Reaction Scheme 1, where $R^3$ is a bridged bicyclic optionally substituted heteroaryl, for example, where $R^3$ is 1,4-ethano-8-phenyl-1,2,3,4-tetrahydro-1,5-naphthyridin-6-yl, i.e., where $R^3$ has the following structure:

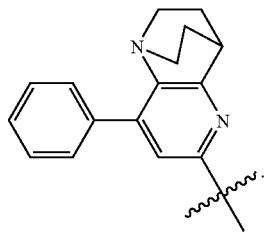

Compounds of formula (D-2) can be prepared according to the method disclosed below in Reaction Scheme 4:

REACTION SCHEME 4

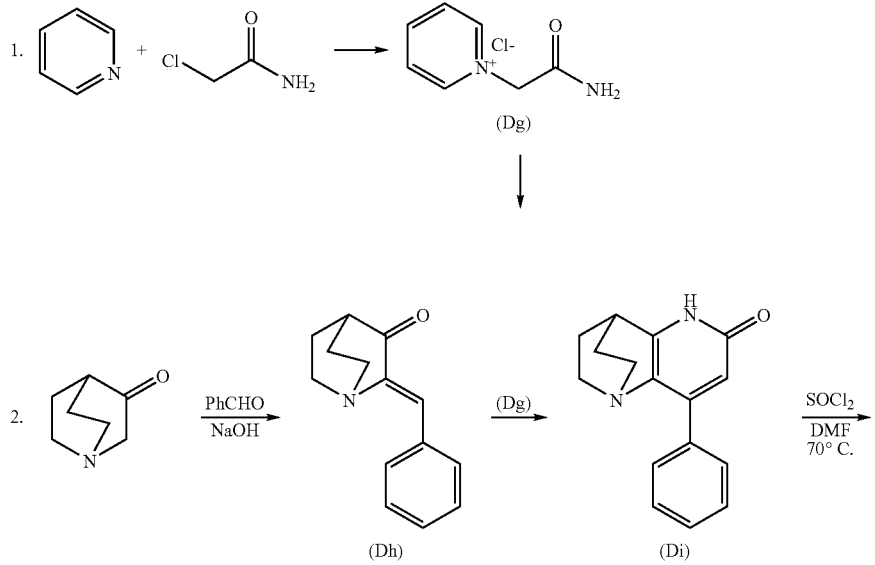

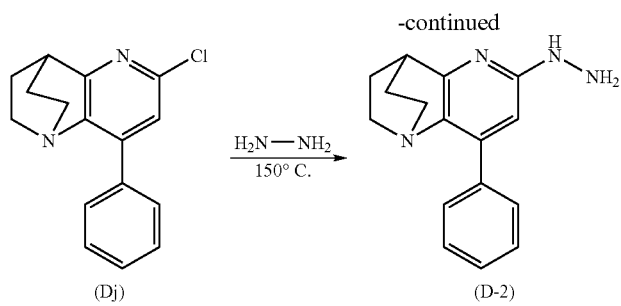

Pyridine, 2-chloroacetamide and quinuclidin-3-one are commercially available or can be prepared according to methods known to one skilled in the art.

In general, compounds of formula (D-2) are prepared, as set forth above in Reaction Scheme 4, by first treating a suspension of 2-chloroacetamide in an aprotic polar solvent, such as, but not limited to, acetonitrile, with an equimolar amount of pyridine. The reaction mixture is stirred at a suitable temperature of between about 70° C. and about 100° C. for a suitable period of time of between about 4 hours and 10 hours. The compound of formula (Dg) is isolated from the reaction mixture by standard isolation techniques, such as filtration and recrystallization.

A mixture of 3-quinuclidinone and an equimolar amount of benzaldehyde (PhCHO) in a protic solvent, such as, but not limited to, ethanol, and in the presence of a base, such as sodium hydroxide (NaOH), is refluxed for a suitable period of time of between about 1 hour and 3 hours. After the resulting solution is cooled to ambient temperature, the compound of formula (Dh) is isolated by standard isolation techniques.

A solution of the compound of formula (Dh) and an excess molar amount of the compound of formula (Dg) in a protic solvent, such as, but not limited to, n-butanol, in the presence of a base, such as, but not limited to, pyridine, and a weak acid, such as, but not limited to, acetic acid, is stirred at a suitable temperature of between about 110° C. and about 125° C. for a suitable period of time of between about 10 hours and about 20 hours. After the reaction mixture is cooled to ambient temperature, the compound of formula (Di) is isolated from the reaction mixture by standard isolation techniques, such as concentration, extraction and recrystallization.

To a solution of a compound of formula (Di) in a suitable amount of thionyl chloride is added a catalytic amount of a dialkylformamide, preferably dimethylformamide (DMF). The resulting reaction mixture is heated to a suitable temperature of between about 40° C. and about 100° C., preferably of between about 60° C. and about 80° C., more preferably of between about 65° C. and about 75° C., for a suitable period of time of between about 2 hours and about 20 hours, preferably of between about 5 hours and about 15 hours, more preferably of between about 8 hours and about 12 hours. The resulting reaction mixture is allowed to cool to ambient temperature and concentrated. The resulting residue is poured over ice-water and a saturated solution of sodium carbonate is added to adjust the pH of the resulting solution to a pH of between about 10 and 11. The compound of formula (Dj) is isolated from the resulting solution by standard isolation techniques, such as concentration and purification by flash chromatography.

The compound of formula (Dj) is then treated with anhydrous ethanol and anhydrous hydrazine in the presence of an acid, such as, but not limited to, hydrochloric acid. The resulting reaction mixture is heated to a suitable temperature of between about 140° C. and about 160° C. for a suitable period of time of between about 80 hours and about 100 hours to yield the compound of formula (D-2), which is isolated from the reaction mixture by standard isolation techniques, such as concentration, extraction, removal of water and concentration.

All compounds of the invention which exist in free base or acid form can be converted to their pharmaceutically acceptable salts by treatment with the appropriate inorganic or organic base or acid by methods known to one of ordinary skill in the art. Salts of the compounds of the invention can be converted to their free base or acid form by standard techniques known to one skilled in the art.

The following specific Synthetic Preparations (for intermediates) and Synthetic Examples (for compounds of the invention) are provided as a guide to assist in the practice of the invention, and are not intended as a limitation on the scope of the invention. The number following each compound below refers to its number in Table 1, as discussed in more detail below.

Synthetic Preparation 1

Compound of Formula (Cc)

A mixture of 3,3-dimethyl-1,5-dioxaspiro[5.7]tridecan-10-one (compound of formula (Ca)) (1.32 g, 5.83 mmol), 1-methyl-3,5-dinitro-1H-pyridin-2-one (compound of formula (Cb)) (1.07 g, 5.3 mmol) and 7N ammonia solution in methanol (45 mL) was heated at 80° C. in sealed vessel overnight. The solvent was evaporated and the residue was dissolved in dichloromethane (DCM). The soluble portion was concentrated and purified by flash chromatography on silica gel (hexane/ethyl acetate, 3:1) to give the compound of formula (Cc), 5',5'-dimethyl-3-nitro-6,8,9,10-tetrahydro-5H-spiro[cycloocta[b]pyridine-7,2'-[1,3]dioxane] (1.5 g, 92.5%); $^1$H NMR (DMSO-$d_6$, 300 MHz) 9.09 (s, 1H), 8.40 (s, 1H), 3.37 (m, 4H), 3.02 (t, 2H), 2.89 (m, 2H), 2.02 (m, 2H), 1.77 (m, 2H), 1.58 (t, 2H), 0.86 (d, 6H) ppm; MS (ES) 306.99 (M+H).

Synthetic Preparation 2

Compound of Formula (Cd)

The compound of formula (Cc), 5',5'-dimethyl-3-nitro-6,8,9,10-tetrahydro-5H-spiro[cycloocta[b]pyridine-7,2'-[1,3]dioxane], was hydrogenated in ethanol/THF solution over 10% Pd/C for 1 hour at 40 psi to give the compound of formula (Cd), 5',5'-dimethyl-6,8,9,10-tetrahydro-5H-spiro[cycloocta[b]pyridine-7,2'-[1,3]dioxan]-3-amine, in quantitative yield; MS (ES) 277.67 (M+2H).

Synthetic Preparation 3

Compound of Formula (C-1)

A mixture of the compound of formula (Cd), 5',5'-dimethyl-6,8,9,10-tetrahydro-5H-spiro[cycloocta[b]pyridine-7,2'-[1,3]dioxan]-3-amine (1.08 g, 3.9 mmol), diphenylcyanocarboimidate (0.93 g, 3.9 mmol), diisopropylethylamine (680 µl, 3.9 mmol) and isopropyl alcohol (15 mL) was stirred at ambient temperature overnight. The solvent was evaporated, and the residue was purified by flash chromatography on silica gel (ethyl acetate) to the compound of formula (C-1), phenyl N'-cyano-N-(5',5'-dimethyl-6,8,9,10-tetrahydro-5H-spiro[cycloocta[b]pyridine-7,2'-[1,3]dioxane]-3-yl)carbamimidate, (1.09 g, 66.8%); $^1$H NMR (DMSO-$d_6$, 300 MHz) 10.81 (s, 1H), 8.36 (s, 1H), 7.64 (s, 1H), 7.42 (t, 2H), 7.28 (m, 3H), 3.37 (m, 4H), 2.87 (t, 2H), 2.73 (m, 2H), 1.97 (m, 2H), 1.70 (m, 2H), 1.54 (m, 2H), 0.85 (d, 6H) ppm; MS (ES) 421.01 (M+H).

Synthetic Preparation 4

Compound of Formula (Db)

To a mixture of 1-benzosuberone (5.0 g, 31.2 mmol, Aldrich) in dry tetrahydrofuran ("THF") (20 mL) was added hexamethylphosphoramide (6.5 mL, 37.5 mmol) (99%, Aldrich). The resulting mixture was stirred at ambient temperature for 10 min and then cooled to 0° C. with a ice-water bath, 1.0 M solution of lithium bis(trimethylsilyl)-amide in THF (32.7 mL, 32.7 mmol) was added dropwise in 30 min. After the addition, the reaction mixture was stirred at 0° C. for 30 min. Ethyl bromoacetate (8.7 mL, 78.1 mmol) was then added. After stirring for a further 10 min, the reaction mixture was warmed to ambient temperature and stirred for 2 h. Solvent was evaporated, the residue was diluted with ethyl acetate (EtOAc) (300 mL), and washed with water and brine. After being dried (MgSO$_4$), filtered, and concentrated, the residue was purified by flash column chromatography eluting with hexanes-ethyl acetate 6:1→4:1) to afford 6.6 g of the compound of formula (Db), ethyl 2-(5-oxo-6,7,8,9-tetrahydro-5H-benzo[7]annulen-6-yl)acetate, as an orange oil (84%), $^1$H NMR (300 MHz, CDCl$_3$) δ: 7.69-7.21 (m, 4H), 4.22-4.05 (m, 2H), 3.40-3.30 (m, 1H), 3.12-2.92 (m, 3H), 2.52-2.43 (m, 1H), 2.20-1.58 (m, 4H), 1.28-1.21 (m, 3H); LC-MS: purity: 91.8%; MS (m/e): 247 (MH$^+$).

Synthetic Preparation 5

Compound of Formula (Dc)

The compound of formula (Db), ethyl 2-(5-oxo-6,7,8,9-tetrahydro-5H-benzo[7]annulen-6-yl)acetate, (6.6 g, 26.8 mmol) was dissolved in ethanol (EtOH) (30 mL), then 10% potassium hydroxide (KOH) aqueous solution (37.5 mL, 67 mmol) was added and the resulting mixture was refluxed for 2 h. After cooling to ambient temperature, the EtOH was removed by evaporation. The residue was extracted with EtOAc twice (15 mL×2). The aqueous layer was then transferred into a flask and cooled with an ice-water bath, con. HCl was added dropwise to adjust pH to about 2.0. EtOAc (60 mL) was then added, the layers were separated, and the aqueous layer was extracted with EtOAc. The combined extracts were washed with brine. After being dried (MgSO$_4$), filtered, and concentrated, the compound of formula (Dc), 2-(5-oxo-6,7,8,9-tetrahydro-5H-benzo[7]annulen-6-yl)acetic acid, was obtained as an orange oil (5.7 g, 97%); $^1$H NMR (300 MHz, CDCl$_3$) δ: 7.71-7.68 (m, 1H), 7.41-7.20 (m, 3H), 3.37-3.31 (m, 1H), 3.12-2.91 (m, 3H), 2.57-2.49 (m, 1H), 2.15-1.90 (m, 2H), 1.75-1.62 (m, 2H); LC-MS: purity: 100%; MS (m/e): 219 (MH$^+$).

Synthetic Preparation 6

Compound of Formula (Dd)

A mixture of the compound of formula (Dc), 2-(5-oxo-6,7,8,9-tetrahydro-5H-benzo[7]annulen-6-yl)acetic acid, (5.7 g, 26.1 mmol) and hydrazine hydrate (1.6 mL, 32.7 mmol) in 20 mL of ethanol was refluxed for 2 h, cooled and filtered (washed with small amount of EtOH) to give the compound of formula (Dd), 8,9-benzo-4a,5,6,7-tetrahydro-2H-cyclohepta[c]pyridazin-3(4H)-one, as a white solid (4.7 g, 84%); $^1$H NMR (300 MHz, CDCl$_3$) δ: 8.61 (bs, 1H), 7.53-7.14 (m, 4H), 2.98-2.75 (m, 3H), 2.58 (dd, J=15.3, 16.8 Hz, 1H), 2.31 (dd, J=12.0, 16.8 Hz, 1H), 1.96-1.59 (m, 4H); LC-MS: purity: 100%; MS (m/e): 215 (MH$^+$).

Synthetic Preparation 7

Compound of Formula (De)

A mixture of the compound of formula (Dd), 8,9-benzo-4a,5,6,7-tetrahydro-2H-cyclohepta[c]pyridazin-3(4H)-one, (4.7 g, 22 mmol) and anhydrous copper(II) chloride (6 g, 44 mmol) was refluxed in acetonitrile (45 mL) for 2 hours. After cooling to ambient temperature, the mixture was poured into ice-water (200 g) and the solid obtained was washed with 10% HCl solution twice (about 20 mL×2) and cold water twice (about 20 mL×2). After freeze-drying, the compound of formula (De), 8,9-benzo-6,7-dihydro-2H-cyclohepta[c]pyridazin-3(5H)-one, (4.2 g, 90%) was obtained as a white solid, $^1$H NMR (300 MHz, CDCl$_3$) δ: 10.80 (bs, 1H), 7.53-7.21 (m, 4H), 6.77 (s, 1H), 2.66 (t, J=6.9 Hz, 2H), 2.45 (t, J=6.9 Hz, 2H), 2.14 (quant, J=6.9 Hz, 2H); LC-MS: purity: 100%; MS (m/e): 213 (MH$^+$).

Synthetic Preparation 8

Compound of Formula (Df)

A mixture of the compound of formula (De), 8,9-benzo-6,7-dihydro-2H-cyclohepta[c]pyridazin-3(5H)-one, (4.0 g, 19.3 mmol) and POCl$_3$ (20 mL) was refluxed for 2 h. After cooling to ambient temperature, the volatiles were evaporated. The residue was poured into a mixture of ice water and sodium bicarbonate, CH$_2$Cl$_2$ (200 mL) was added to dissolve the solid. The layers were separated, and the aqueous layer was extracted with CH$_2$Cl$_2$ one more time. The combined organic layers were washed with brine. After being dried (MgSO$_4$), filtered, and concentrated, the compound of formula (Df), 8,9-benzo-3-chloro-6,7-dihydro-5H-cyclohepta[c]pyridazine, was obtained as a yellow solid (4.3 g, 99%), $^1$H NMR (300 MHz, CDCl$_3$) δ: 7.82 (m, 1H), 7.45-7.24 (m, 4H), 2.59-2.51 (m, 4H), 2.27 (quant, J=6.9 Hz, 2H); LC-MS: purity: 100%; MS (m/e): 231 (MH$^+$).

Synthetic Preparation 9

Compound of Formula (D-1)

A mixture of the compound of formula (Df), 8,9-benzo-3-chloro-6,7-dihydro-5H-cyclohepta[c]pyridazine, (4.3 g, 18.6 mmol) and anhydrous hydrazine (11.7 mL, 370 mmol) in 45 mL of ethanol was refluxed for 16 h. After cooling to ambient temperature, 5 mL of water was added and the volatiles were then evaporated. To the solid residue was added cold water (about 80 mL). After sonication for 10 min, the resulting solid was collected by filtration and washed with cold water three times. After freeze-drying, the compound of formula (D-1), (6,7-dihydro-5H-benzo[6,7]cyclohepta[1,2-c]pyridazin-3-yl)hydrazine, (4.14 g, 98%) was obtained as a slight yellow solid, $^1$H NMR (300 MHz, CD$_3$OD) δ: 7.59 (m, 1H), 7.39-7.26 (m, 3H), 7.04 (s, 1H), 2.54 (t, J=6.9 Hz, 2H), 2.47 (t, J=6.9 Hz, 2H), 2.18 (quant, J=6.9 Hz, 2H); LC-MS: purity: 100%; MS (m/e): 227 (MH$^+$).

Synthetic Preparation 10

Synthesis of 1-(2-amino-2-oxoethyl)pyridinium chloride (Dg)

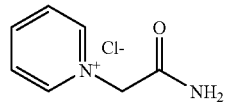

To a suspension of 2-chloroacetamide (50.00 g, 524.01 mmol) in 100 mL of acetonitrile was added pyridine (41.45 g, 524.01 mmol). After being stirred at 90° C. for 10 h, the suspension was cooled to 22° C., suction-filtered and washed with 100 mL of hexanes. The product, 1-(2-amino-2-oxoethyl)pyridinium chloride (79.10 g, yield: 87%, mp 205.2° C.), was obtained as colorless crystals after being recrystallized from methanol.

Synthetic Preparation 11

Synthesis of (Z)-2-benzylidenequinuclidin-3-one (Dh)

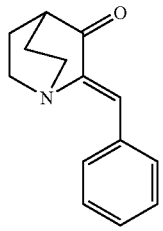

A mixture of 3-quinuclidinone (20.9 g, 167 mmol), benzaldehyde (17.7 g, 167 mmol), and one pellet of sodium hydroxide in 75 mL of ethanol was refluxed for 1.5 h. After the solution was cooled, the yellow precipitates were collected, washed with ethanol, and dried to give (Z)-2-benzylidenequinuclidin-3-one (32.5 g, yield: 91.2%, mp 130-132° C.).

Synthetic Preparation 12

Synthesis of 1,4-ethano-8-phenyl-1,2,3,4-tetrahydro-1,5-naphthyridin-6-one (Di)

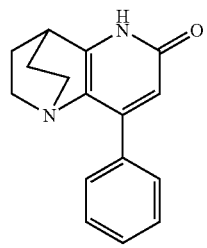

A solution of 2-benzylidenequiclidin-3-one (3.0 g, 14.1 mmol) and 1-(2-amino-2-oxoethyl)pyridinium chloride (7.3 g, 42.3 mmol) in butan-1-ol (100 mL) containing piperidine (5 mL) and HOAc (3 mL) was stirred at 115-120° C. for 18 h. After cooling to ambient temperature, the mixture was concentrated in vacuo and the resulting residue was partitioned between 5% MeOH in CHCl$_3$ (2×150 mL) and water. The organic phase was concentrated to give a crystalline residue, which was recrystallized from MeOH to give 1,4-ethano-8-phenyl-1,2,3,4-tetrahydro-1,5-naphthyridin-6-one (2.91 g, yield: 82%, mp 220° C.).

Synthetic Preparation 13

Synthesis of 6-chloro-1,4-ethano-8-phenyl-1,2,3,4-tetrahydro-1,5-naphthyridine (Dj)

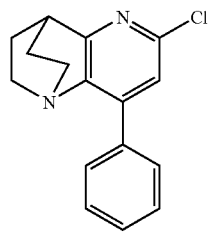

To a solution of 1,4-ethano-8-phenyl-1,2,3,4-tetrahydro-1,5-naphthyridin-6-one (435 mg, 1.72 mmol) in 2.5 ml of thionyl chloride was added 100 μL of DMF, and the reaction mixture was heated at 70° C. for 10 h, and concentrated in vacuo. The residue was poured on ice-water and saturated aq. NaHCO$_3$ solution was added to adjust pH to 10-11. The mixture was extracted with EtOAc (2×50 mL), dried over Na$_2$SO$_4$, concentrated and purified by flash chromatography (EtOAc:hexane, 1:4) to give 6-chloro-1,4-ethano-8-phenyl-1,2,3,4-tetrahydro-1,5-naphthyridine (310 mg, 66%) as a white solid; $^1$H NMR (CDCl$_3$, 300 MHz) 7.58 (m, 2H), 7.43 (m,3H), 7.29 (s, 1H), 3.35 (s, 1H), 3.18 (m, 2H), 2.63 (m, 2H), 1.99 (m, 2H), 1.73 (m, 2H) ppm; MS (ES) 271.39 (M+H).

Synthetic Preparation 14

Synthesis of 6-hydrazino-1,4-ethano-8-phenyl-1,2,3,4-tetrahydro-1,5-naphthyridine (D-2) and N,N-di(tert-butoxycarbonyl)-6-hydrazino-1,4-ethano-8-phenyl-1,2,3,4-tetrahydro-1,5-naphthyridine

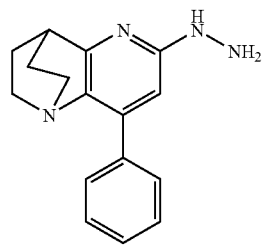

A. 6-Chloro-1,4-ethano-8-phenyl-1,2,3,4-tetrahydro-1,5-naphthyridine (1.03 g) was treated with anhydrous ethanol (10 mL), anhydrous hydrazine (Aldrich, 4.0 mL) and concentrated HCl (0.4 mL). The reaction mixture was then heated in a screw cap pressure tube at 150° C. until LCMS showed complete conversion to the hydrazine (approx. 96 h). The reaction mixture was cooled to ambient temperature, then concentrated under vacuum. The residue was partitioned between chloroform and brine. The organic layer was dried over anhydrous sodium sulfate and concentrated under vacuum to give 6-hydrazino-1,4-ethano-8-phenyl-1,2,3,4-tetrahydro-1,5-naphthyridine as a pale yellow solid (0.68 g).

B. Alternatively, in a manner similar to that described in *Org. Lett* (2001), Vol. 3, No. 9, pp. 1351-1354, 6-chloro-1,4-ethano-8-phenyl-1,2,3,4-tetrahydro-1,5-naphthyridine (375 mg, 1.4 mmol), $Cs_2CO_3$ (460 mg, 1.4 mmol), di-tert-butyl-hydrazodiformate (325 mg, 1.4 mmol, Aldrich), toluene (5.0 mL), $Pd_2(dba)_3$ (90 mg, 0.1 mmol, Sterm Chemicals), and DPPF (80 mg, 0.14 mmol, Sterm Chemicals) were placed in a dry screw cap pressure tube charged with argon. The reaction mixture was heated at 100° C. for 48 hours until complete conversion to N,N-di(tert-butoxycarbonyl)-6-hydrazino-1,4-ethano-8-phenyl-1,2,3,4-tetrahydro-1,5-naphthyridine. Conversion was followed by TLC. After 24 hours, approximately 50% conversion occurred. Additional portions of $Cs_2CO_3$ (230 mg, 0.7 mmol), di-tert-buthyl-hydrazodiformate (160 mg, 0.7 mmol, Aldrich), $Pd_2(dba)_3$ (45 mg, 0.05 mmol,), and DPPF (40 mg, 0.07 mmol) were added at this time. The reaction mixture was cooled to ambient temperature, concentrated under vacuum and purified by column chromatography on silica gel (ethyl acetate:hexane, 1:1) to give N,N-di(tert-butoxycarbonyl)-6-hydrazino-1,4-ethano-8-phenyl-1,2,3,4-tetrahydro-1,5-naphthyridine (340 mg, 52%) as a tan solid; $^1$H NMR ($CDCl_3$, 300 MHz) 7.59 (d, 2H), 7.40 (m, 3H), 7.02 (s, 1H), 3.28 (s, 1H), 3.17 (m, 2H), 2.65 (m, 2H), 1.96 (m, 2H), 1.73 (m, 2H), 1.53 (s, 9H), 1.48 (s, 9H) ppm; MS (ES) 467 (M+H).

Synthetic Example 1

1-(6,7-dihydro-5H-benzo[6,7]cyclohepta[1,2-c]pyridazin-3-yl)-$N^3$-(7-oxo-5,6,8,9,10-pentahydrocycloocta[b]pyridin-3-yl)-1H-1,2,4-triazole-3,5-diamine To a suspension of 1-(6,7-dihydro-5H-benzo[6,7]cyclohepta[1,2-c]pyridazin-3-yl)-$N^3$-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine (50 mg, 0.09 mmol) in acetonitrile (5 mL) was added 5 mL of 20% aqueous trifluoroacetic acid, the reaction mixture was stirred for 1 h at ambient temperature, lyophilized to give 1-(6,7-dihydro-5H-benzo[6,7]cyclohepta[1,2-c]pyridazin-3-yl)-$N^3$-(7-oxo-5,6,8,9,10-pentahydrocycloocta[b]pyridin-3-yl)-1H-1,2,4-triazole-3,5-diamine, compound #6, as trifluoroacetic acid salt; $^1$H NMR (DMSO-$d_6$, 300 MHz) 10.31 (s, 1H), 9.11 (d, 1H), 8.15 (d, 1H), 8.07 (s, 1H), 8.02 (s, 2H), 7.71 (m, 1H), 7.45 (m, 2H), 7.36 (m, 1H), 3.27 (m, 2H), 3.10 (m, 2H), 2.71 (m, 2H), 2.61 (m, 2H), 2.54 (m, 4H), 2.25 (m, 2H), 1.79 (s, 2H) ppm; MS (ES) 467.09 (M+H).

Synthetic Example 2

1-(6,7-dihydro-5H-benzo[6,7]cyclohepta[1,2-c]pyridazin-3-yl)-$N^3$-(7-(pyrrolidin-1-yl)-5,6,7,8,9,10-hexahydrocycloocta[b]pyridin-3-yl)-1H-1,2,4-triazole-3,5-diamine To a solution of 1-(6,7-dihydro-5H-benzo[6,7]cyclohepta[1,2-c]pyridazin-3-yl)-$N^3$-(7-oxo-5,6,8,9,10-pentahydrocycloocta[b]pyridin-3-yl)-1H-1,2,4-triazole-3,5-diamine (65 mg, 0.112 mmol) in THF (8 mL) was added pyrrolidine (90 µL, 1.12 mmol). The reaction mixture was heated at 50° C. for 15 min, cooled to ambient temperature, and then sodium triacetoxyborohydride (90 mg, 0.42 mmol) was added. The reaction mixture was stirred at ambient temperature overnight. The solvent was evaporated, the residue was dissolved in dichloromethane, washed with water, brine, dried over sodium sulphate, and evaporated to give 1-(6,7-dihydro-5H-benzo[6,7]cyclohepta[1,2-c]pyridazin-3-yl)-$N^3$-(7-(pyrrolidin-1-yl)-5,6,7,8,9,10-hexahydrocycloocta[b]pyridin-3-yl)-1H-1,2,4-triazole-3,5-diamine, compound #7, (35 mg, 60%); $^1$H NMR ($CDCl_3$, 300 MHz) 8.88 (s, 1H), 7.90 (s, 1H), 7.88 (t, 1H), 7.62 (s, 1H), 7.43 (m, 2H), 7.29 (m, 1H), 7.17 (s, 2H), 3.66 (m, 2H), 2.96 (m, 4H), 2.69-2.57 (m, 6H), 2.33 (m, 2H), 2.11-1-88 (m, 8H), 1.62 (m, 1H), 1.25 (s, 2H) ppm; MS (ES) 522.57 (M+H).

Synthetic Example 3

1-(6,7-dihydro-5H-benzo[6,7]cyclohepta[1,2-c]pyridazin-3-yl)-$N^3$-(7-(methoxyimino)-5,6,7,8,9,10-hexahydrocycloocta[b]pyridin-3-yl)-1H-1,2,4-triazole-3,5-diamine A mixture of 1-(6,7-dihydro-5H-benzo[6,7]cyclohepta[1,2-c]pyridazin-3-yl)-$N^3$-(7-oxo-5,6,8,9,10-pentahydrocycloocta[b]pyridin-3-yl)-1H-1,2,4-triazole-3,5-diamine (57 mg, 0.122 mmol), methoxylamine hydrochloride (30 mg, 0.36 mmol), sodium hydroxide (80 mg, 2 mmol) in ethanol:dichloromethane (1:1; 5 mL) was stirred at ambient temperature for 17 h. The reaction mixture was diluted with water (10 mL), neutralized with 2N HCl, extracted with dichloromethane, dried over sodium sulphate, concentrated and purified by flash chromatography on silica gel (10% methanol in ethyl acetate) to give 1-(6,7-dihydro-5H-benzo[6,7]cyclohepta[1,2-c]pyridazin-3-yl)-$N^3$-(7-(methoxyimino)-5,6,7,8,9,10-hexahydrocycloocta[b]pyridin-3-yl)-1H-1,2,4-triazole-3,5-diamine, compound #8, (27 mg) as a mixture of cis- and trans-isomers; $^1$H NMR (DMSO-$d_6$, 300 MHz) 9.26 (d, 1H), 8.72 (s, 1H), 7.95 (s, 1H), 7.87 (s, 2H), 7.73 (m, 1H), 7.63 (m, 1H), 7.43 (m, 2H), 7.36 (m, 1H), 3.57 (m, 2H), 2-89-2.79 (m, 4H), 2.61 (m, 2H), 2.54 (m, 2H), 2.41 (m, 1H), 2.23 (m, 2H), 2.15 (m, 1H), 1.78 (s, 2H) ppm; MS (ES) 496.28 (M+H).

Synthetic Example 4

In a similar manner as described above utilizing the appropriately substituted starting materials and reagents, the following compounds of formula (Ia) were prepared:

1-(6,7-dihydro-5H-benzo[6,7]cyclohepta[1,2-c]pyridazin-3-yl)-$N^3$-(4(1H)-oxo-2,2,5,6-tetrahydrobenzo[d]azocin-8-yl)-1H-1,2,4-triazole-3,5-diamine, compound #1, $^1$H NMR (DMSO-$d_6$, 300 MHz) 9.07 (s, 1H), 7.92 (s, 1H), 7.84 (br s, 2H), 7.45 (m, 3H), 7.37 (m, 2H), 7.02 (m, 3H), 3.38 (m, 2H), 2.88 (m, 4H), 2.55 (m, 6H), 2.23 (m, 2H) ppm; MS (ES) 467.1 (M+H);

1-(6,7-dihydro-5H-benzo[6,7]cyclohepta[1,2-c]pyridazin-3-yl)-$N^3$-(3-cyclopentyl-1,2,3,4,5,6-hexahydrobenzo[d]azocin-8-yl)-1H-1,2,4-triazole-3,5-diamine, compound #2, $^1$H NMR (DMSO-$d_6$, 300 MHz) 9.22 (s, 1H), 7.84 (br s, 2H), 7.73 (m, 2H), 7.42 (m, 5H), 7.13 (m, 1H), 2.71 (m, 5H), 2.54 (m, 4H), 2.22 (m, 4H), 1.96-1.21 (m, 12H) ppm; MS (ES) 521.3 (M+H);

1-(6,7-dihydro-5H-benzo[6,7]cyclohepta[1,2-c]pyridazin-3-yl)-$N^3$-(3-cyclopentyl-1,2,3,4,5,6-hexahydrobenzo[d]azocin-9-yl)-1H-1,2,4-triazole-3,5-diamine, compound #3, $^1$H NMR (DMSO-$d_6$, 300 MHz) 8.99 (s, 1H), 7.91 (s, 1H), 7.83 (br s, 2H), 7.70 (m, 1H), 7.45 (m, 4H), 7.18 (m, 1H), 6.99 (m, 1H), 2.70-2.42 (m, 9H), 2.22 (m, 4H), 1.50 (m, 12H) ppm; MS (ES) 521.3 (M+H);

1-(6,7-dihydro-5H-benzo[6,7]cyclohepta[1,2-c]pyridazin-3-yl)-$N^3$-(7-pyrrolidin-1-yl-6,8-ethano-6,7,8,9-tetrahydro-5H-benzo[7]annulene-3-yl)-1H-1,2,4-triazole-3,5-diamine, compound #4, $^1$H NMR (DMSO-$d_6$, 300 MHz) 9.25 (s, 1H), 7.85 (br s, 2H), 7.71 (m, 1H), 7.65 (m, 1H). 7.45 (m, 3H), 7.38 (m, 2H), 7.17 (m, 1H), 3.68 (m, 3H), 3.04 (m, 4H), 2.77-2.41 (m, 8H), 2.20 (m, 2H), 2.05 (m, 4H), 1.72 (m, 2H), 1.17 (m, 2H) ppm; MS (ES) 533.2 (M+H);

1-(6,7-dihydro-5H-benzo[6,7]cyclohepta[1,2-c]pyridazin-3-yl)-$N^3$-(6-pyrrolidin-1-yl-5,6,7,8,9,10-hexahydrobenzo[8]annulene-3-yl)-1H-1,2,4-triazole-3,5-diamine, compound #5, $^1$H-NMR (CDCl$_3$/MeOD$_4$, 300 MHz) 7.78 (s, 1H), 7.70 (m, 1H), 7.62 (m, 1H), 7.38 (m, 2H), 7.24 (m, 1H), 7.07 (m, 2H), 3.31 (m, 4H), 3.12 (m, 3H), 2.55-2.80 (m, 7H), 2.26 (m, 2H), 2.03 (m, 3H), 1.78 (m, 3H), 1.45-1.65 (m, 2H), 1.06 (m, 1H) ppm; MS (ES) 521.30 (M+H);

1-(6,7-dihydro-5H-benzo[6,7]cyclohepta[1,2-c]pyridazin-3-yl)-$N^3$-(7-hydroxy-5,6,7,8,9,10-hexahydrocycloocta[b]pyridin-3-yl)-1H-1,2,4-triazole-3,5-diamine (formic acid salt), compound #9; $^1$H NMR (DMSO-$d_6$, 300 MHz) 10.13 (s, 1H), 9.05 (s, 1H), 8.04 (m, 4H), 7.71 (m, 1H), 7.45 (m, 2H), 7.37 (m, 1H), 2.92 (m, 4H), 2.56 (m, 3H), 2.24 (t, 3H), 1.91 (m, 2H), 1.64-1.48 (m, 5H) ppm; MS (ES) 469.19 (M+H);

1-(1,4-ethano-8-pyridin-4-yl-1,2,3,4-tetrahydro-1,5-naphthyridin-6-yl)-$N^3$-(7-oxo-5,6,7,8,9,10-hexahydrocycloocta[b]pyridin-3-yl)-1H-1,2,4-triazole-3,5-diamine (trifluoroacetic acid salt), compound #10; $^1$H NMR (DMSO-$d_6$, 300 MHz) 9.52 (s, 1H), 8.69 (m, 3H), 8.10 (s, 1H), 7.85 (s, 1H), 7.74 (s, 2H), 7.66 (d, 2H), 7.60 (s, 1H), 3.40 (s, 2H), 3.08 (m, 4H), 2.91 (s, 2H), 2.60 (m, 4H), 2.42 (t, 1H), 1.98 (m, 2H), 1.68 (m, 4H) ppm; MS (ES) 508.42 (M+H);

1-(6,7-dihydro-5H-benzo[6,7]cyclohepta[1,2-c]pyridazin-3-yl)-$N^3$-(1(2H)-oxo-3,4,5,6-tetrahydrobenzo[c]azocin-9-yl)-1H-1,2,4-triazole-3,5-diamine, compound #11; $^1$H NMR (DMSO-$d_6$, 300 MHz) 9.50 (s, 1H), 9.27 (s, 1H), 7.95 (s, 1H), 7.87 (s, 2H), 7.70 (m, 1H), 7.52-7.32 (m, 5H), 7.18 (d, 1H), 3.33 (m, 6H), 2.67-2.38 (m, 4H), 2.24 (m, 2H), 1.95 (m, 2H) ppm; MS (ES) 467.14 (M+H), 465.31 (M−H);

1-(6,7-dihydro-5H-benzo[6,7]cyclohepta[1,2-c]pyridazin-3-yl)-$N^3$-(1(2H)-oxo-3,4,5,6-tetrahydrobenzo[c]azocin-9-yl)-1H-1,2,4-triazole-3,5-diamine trifluoroacetic acid salt, compound #12 (trifluoroacetic salt of compound #11); $^1$H NMR (DMSO-$d_6$, 300 MHz) 9.50 (s, 1H), 9.27 (s, 1H), 7.95 (s, 1H), 7.87 (s, 2H), 7.70 (m, 1H), 7.52-7.32 (m, 5H), 7.18 (d, 1H), 3.33 (m, 6H), 2.67-2.38 (m, 4H), 2.24 (m, 2H), 1.95 (m, 2H) ppm; MS (ES) 467.18 (M+H), 465.34 (M−H);

1-(6,7-dihydro-5H-benzo[6,7]cyclohepta[1,2-c]pyridazin-3-yl)-$N^3$-(1,2,3,4,5,6-hexahydrobenzo[c]azocin-9-yl)-1H-1,2,4-triazole-3,5-diamine (trifluoroacetic acid salt), compound #13; $^1$H NMR (DMSO-$d_6$, 300 MHz) 9.06 (s, 1H), 7.91 (s, 1H), 7.84 (s, 2H), 7.71 (m, 1H), 7.40 (m, 3H), 7.29 (m, 1H), 7.21 (m, 1H), 6.86 (d, 1H), 6.79 (d, 1H), 3.45 (m, 2H), 2.58-2.35 (m, 8H), 2.15 (m, 3H), 1.67 (m, 2H), 1.41 (m, 2H) ppm; MS (ES) 453.20 (M+H), 451.30 (M−H); and 1-(5,6,7,8,9,10-hexahydrocycloocta[d]pyrimidin-4-yl)-$N^3$-(5,6,8,9-tetrahydrospiro[benzo[7]annulene-7,2'-[1,3]dioxolane]-3-yl)-1H-1,2,4-triazole-3,5-diamine (trifluoroacetic acid salt), compound #14; $^1$H NMR (CD$_3$OD, 300 MHz) 8.70 (s, 1H), 7.45 (m, 1H), 7.31 (m, 1H), 7.19 (m, 2H), 7.02 (m, 1H), 6.78 (m, 1H), 3.98 (s, 4H), 3.49 (m, 2H), 3.06 (m, 2H), 2.74 (m, 4H), 2.00-1.45 (m, 12H); MS (ES) 462.28 (M+H).

Synthetic Example 5

In a similar manner as described above utilizing the appropriately substituted starting materials and reagents, the following compound of formula (Ib) was prepared:

1-(6,7-dihydro-5H-benzo[6,7]cyclohepta[1,2-c]pyridazin-3-yl)-$N^5$-(1(2H)-oxo-3,4,5,6-tetrahydrobenzo[c]azocin-9-yl)-1H-1,2,4-triazole-3,5-diamine (trifluoroacetic acid salt), compound #15; $^1$H NMR (DMSO-$d_6$, 300 MHz) 11.01 (s, 1H), 9.54 (s, 1H), 7.85 (s, 2H), 7.71 (m, 1H), 7.50-7.30 (m, 4H), 7.28 (d, 1H), 5.94 (s, 2H), 3.32 (m, 6H), 2.65-2.31 (m, 4H), 2.20 (m, 2H), 1.79 (m, 2H) ppm; MS (ES) 467.45 (M+H).

Testing of the Compounds of the Invention

The compounds of the invention were tested in the following assay for their ability to inhibit Axl activity.

Phospho-AKT In-Cell Western Assay

Reagents and Buffers:

Cell culture plate: 96 well assay plate (Corning 3610), white, clear bottom, tissue-culture treated.

Cells: Hela cells.

Starvation medium: For Axl stimulation: 0.5% FCS (fetal calf serum) in DMEM, plus Axl/Fc (extracellular domain of AXL fused to immunoglobulin Fc region) (R&D, 154-AL) 500 ng/mL.

For EGF (epidermal growth factor) stimulation: 0.5% FCS in DMEM (Dulbecco's modified Eagles medium).

Poly-L-Lysine 0.01% solution (the working solution): 10 μg/ml, dilute In PBS (phosphate buffered saline).

Axl antibody cross-linking:

$1^{st}$: Mouse anti-Axl (R&D, MAB154).

$2^{nd}$: Biotin-SP-conjugated AffiniPure goat anti-mouse IgG (H+L) (Jackson ImmunoResearch #115-065-003).

Fixing buffer: 4% formaldehyde in PBS.

Wash buffer: 0.1% TritonX-100 in PBS.

Quenching buffer: 3% $H_2O_2$, 0.1% Azide in wash buffer, Azide and hydrogen peroxide ($H_2O_2$) are added fresh.

Blocking buffer: 5% BSA in TBST (tris buffered saline plus 0.1% Tween 20).

Primary antibody: Rabbit anti-human Phospho-Akt antibody (Cell Signaling 9271): 1×250 diluted in blocking buffer.

Secondary antibody: HRP (horse radish peroxidase)-conjugated Goat anti-Rabbit secondary, stock solution: Jackson ImmunoResearch (Goat anti-Rabbit HRP, #111-035-144) 1:1 diluted in glycerol, store at −20° C. The working solution: 1×2000 dilution of stock in blocking buffer.

Chemiluminescent working solution (Pierce, 37030): SuperSignal ELISA (enzyme linked immunosorbant assay) Pico Chemiluminescent substrate.

Crystal Violet solution: Stock: 2.5% Crystal violet in methanol, filtered and kept at ambient temperature. The working solution: dilute the stock 1:20 with PBS immediately before use.

10% SDS: working solution: 5% SDS (sodium dodecylsulfate), diluted in PBS

Methods:
Day 1:
A 96 well TC (tissue culture treated) plate was coated with 10 μg/mL poly-L-Lysine at 37° C. for 30 min, washed twice with PBS, and air-dried for 5 minutes before cells were added. Hela cells were seeded at 10,000 cells/well and the cells were starved in 100 μL starvation medium containing Axl/Fc for 24 hrs.

Day 2:
The cells were pre-treated with test compounds by adding 100 μL of 2× test compound to the starvation medium on the cells. The cells were incubated at 37° C. for 1 hr before stimulation.

The cells were stimulated by Axl-antibody cross-linking as follows: A 5× $1^{st}/2^{nd}$ Axl antibody mixture was made (37.5 μg/mL $1^{st}$/100 μg/mL $2^{nd}$) in starvation medium and nutated at 4° C. with thorough mixing for 1-2 hours for clustering. The resulting mix was warmed to 37° C. 50 μL of 5× Axl $1^{st}/2^{nd}$ of antibody cluster was added to the cells and the cells were incubated at 37° C. for 5 min.

After 5 minutes stimulation, the plate was flicked to remove medium and the plate was tapped onto paper towels. Formaldehyde (4.0% in PBS, 100 μL) was added to fix the cells and the cells were incubated at ambient temperature for 20 min without shaking.

The cells were washed with a plate washer buffer to remove the formaldehyde solution. The plate was flicked to removed excess wash buffer and tapped onto paper towels. Quenching buffer (100 μL) was added to each well and the cells were incubated at ambient temperature for 20 minutes without shaking.

The cells were washed with a plate washer buffer to remove the quenching buffer. Blocking buffer (100 μL) was added and the cells were incubated at ambient temperature for at least an hour with gentle shaking.

The cells were washed with a plate washer buffer and diluted primary antibody (50 μL) was added to each well (blocking buffer was added to the negative control wells instead). The plates were incubated overnight at 4° C. with gentle shaking.

Day 3:
The wash buffer was removed, diluted secondary antibody (100 μL) was added, and the cells were incubated at ambient temperature for 1 hour with gentle shaking. During the incubation, the chemiluminescent reagent was brought to ambient temperature.

The secondary antibody was removed by washing the cells 1× with wash buffer, 1× with PBS by plate washer. The PBS was removed from the plate and the chemiluminescent reagent (80 μL: 40 μL A and 40 μL B) was added to each well at ambient temperature.

The resulting chemiluminescence was read with a Luminomitor within 10 minutes to minimize changes in signal intensity. After reading the chemiluminescence, the cells were washed 1× with wash buffer and 1× with PBS by plate washer. The plate was tapped onto paper towels to remove excess liquid from wells and air-dried at ambient temperature for 5 minutes.

Crystal Violet working solution (60 μL) was added to each well and the cells were incubated at ambient temperature for 30 min. The crystal violet solution was removed, and the wells were rinsed with PBS, then washed 3× with PBS (200 μL) for 5 minutes each.

5% SDS solution (70 μL) was added to each well and the cells were incubated on a shaker for 30 min at ambient temperature.

The absorbance was read at 590 nM on a Wallac photospec. The 590 nM readings indicated the relative cell number in each well. This relative cell number was then used to normalize each luminescence reading.

The results of the ability of the compounds of the invention to inhibit Axl activity, when tested in the above assay, are shown in the following Table 1 wherein the level of activity (i.e., the $IC_{50}$) for each compound is indicated in the Table. The compound numbers in the Table referred to the compounds disclosed herein as being prepared by the methods disclosed herein:

TABLE 1

(Ia)

| Cpd # | Compound Name | $R^1$ | $R^2$ | $R^3$ | $R^4$ | $R^5$ | $IC_{50}$ |
|---|---|---|---|---|---|---|---|
| 1 | 1-(6,7-dihydro-5H-benzo[6,7]cyclohepta[1,2-c]pyridazin-3-yl)-$N^3$-(4(1H)-oxo-2,3,5,6-tetrahydrobenzo[d]azocin-8-yl)-1H-1,2,4-triazole-3,5-diamine | H | [structure] | [structure] | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 2 | 1-(6,7-dihydro-5H-benzo[6,7]cyclohepta[1,2-c]pyridazin-3-yl)-N³-(3-cyclopentyl-1,2,3,4,5,6-hexahydrobenzo[d]azocin-8-yl)-1H-1,2,4-triazole-3,5-diamine | H | 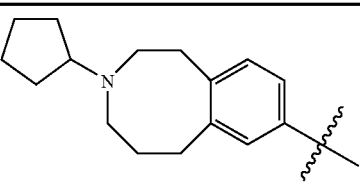 | 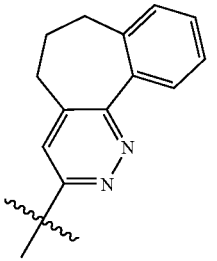 | H | H | B |
| 3 | 1-(6,7-dihydro-5H-benzo[6,7]cyclohepta[1,2-c]pyridazin-3-yl)-N³-(3-cyclopentyl-1,2,3,4,5,6-hexahydrobenzo[d]azocin-9-yl)-1H-1,2,4-triazole-3,5-diamine | H | 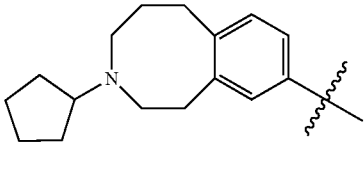 | 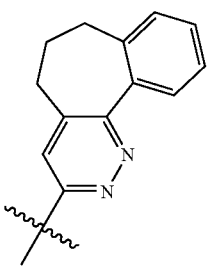 | H | H | A |
| 4 | 1-(6,7-dihydro-5H-benzo[6,7]cyclohepta[1,2-c]pyridazin-3-yl)-N³-(7-pyrrolidin-1-yl-6,8-ethano-6,7,8,9-tetrahydro-5H-benzo[7]annulene-3-yl)-1H-1,2,4-triazole-3,5-diamine | H | 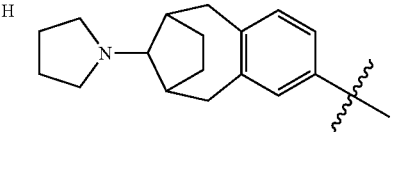 | 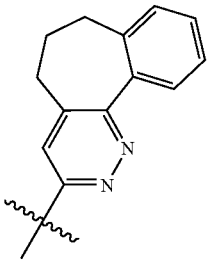 | H | H | A |
| 5 | 1-(6,7-dihydro-5H-benzo[6,7]cyclohepta[1,2-c]pyridazin-3-yl)-N³-(6-pyrrolidin-1-yl-5,6,7,8,9,10-hexahydrobenzo[8]annulene-3-yl)-1H-1,2,4-triazole-3,5-diamine | H | 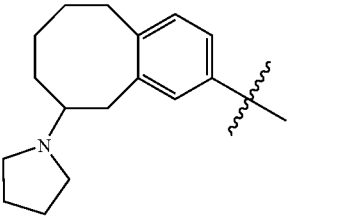 | 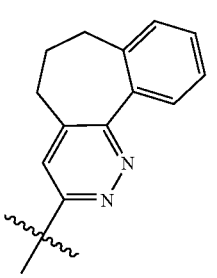 | H | H | B |
| 6 | 1-(6,7-dihydro-5H-benzo[6,7]cyclohepta[1,2-c]pyridazin-3-yl)-N³-(7-oxo-5,6,8,9,10-pentahydrocycloocta[b]pyridin-3-yl)-1H-1,2,4-triazole-3,5-diamine | H | 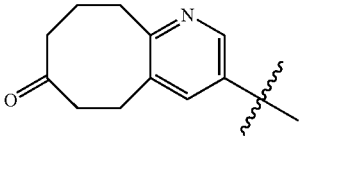 | 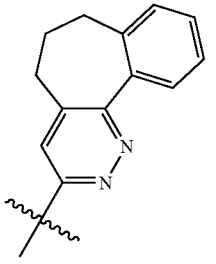 | H | H | A |

TABLE 1-continued (Ia)

| Cpd # | Compound Name | R¹ | R² | R³ | R⁴ | R⁵ | IC$_{50}$ |
|---|---|---|---|---|---|---|---|
| 7 | 1-(6,7-dihydro-5H-benzo[6,7]cyclohepta[1,2-c]pyridazin-3-yl)-N³-(7-(pyrrolidin-1-yl)-5,6,7,8,9,10-hexahydrocycloocta[b]pyridin-3-yl)-1H-1,2,4-triazole-3,5-diamine | H | | | H | H | A |
| 8 | 1-(6,7-dihydro-5H-benzo[6,7]cyclohepta[1,2-c]pyridazin-3-yl)-N³-(7-(methoxyimino)-5,6,7,8,9,10-hexahydrocycloocta[b]pyridin-3-yl)-1H-1,2,4-triazole-3,5-diamine | H | | | H | H | B |
| 9 | 1-(6,7-dihydro-5H-benzo[6,7]cyclohepta[1,2-c]pyridazin-3-yl)-N³-(7-hydroxy-5,6,7,8,9,10-hexahydrocycloocta[b]pyridin-3-yl)-1H-1,2,4-triazole-3,5-diamine | H | | | H | H | B |
| 10 | 1-(1,4-ethano-8-pyridin-4-yl-1,2,3,4-tetrahydro-1,5-naphthyridin-6-yl)-N³-(7-oxo-5,6,7,8,9,10-hexahydrocycloocta[b]pyridin-3-yl)-1H-1,2,4-triazole-3,5-diamine | H | | | H | H | A |
| 11 | 1-(6,7-dihydro-5H-benzo[6,7]cyclohepta[1,2-c]pyridazin-3-yl)-N³-(1(2H)-oxo-3,4,5,6-tetrahydrobenzo[c]azocin-9-yl)-1H-1,2,4-triazole-3,5-diamine | H | | | H | H | B |

TABLE 1-continued (Ia)

| Cpd # | Compound Name | R¹ | R² | R³ | R⁴ | R⁵ | IC$_{50}$ |
|---|---|---|---|---|---|---|---|
| 12 | 1-(6,7-dihydro-5H-benzo[6,7]cyclohepta[1,2-c]pyridazin-3-yl)-N³-(1(2H)-oxo-3,4,5,6-tetrahydrobenzo[c]azocin-9-yl)-1H-1,2,4-triazole-3,5-diamine trifluoroacetic acid salt | H | (structure) | (structure) | H | H | B |
| 13 | 1-(6,7-dihydro-5H-benzo[6,7]cyclohepta[1,2-c]pyridazin-3-yl)-N³-(1,2,3,4,5,6-hexahydrobenzo[c]azocin-9-yl)-1H-1,2,4-triazole-3,5-diamine | H | (structure) | (structure) | H | H | B |
| 14 | 1-(5,6,7,8,9,10-hexahydrocycloocta[d]pyrimidin-4-yl)-N³-(5,6,8,9-tetrahydrospiro[benzo[7]annulene-7,2'-[1,3]dioxolane]-3-yl)-1H-1,2,4-triazole-3,5-diamine | H | (structure) | (structure) | H | H | B |

IC$_{50}$ activity:
A = <1 μM
B = 1 to 10 μM
C = >10 to 20 μM
D = >20 μM

TABLE 2

(Ib)

| Cpd # | Compound Name | R¹ | R² | R³ | R⁴ | R⁵ | IC$_{50}$ |
|---|---|---|---|---|---|---|---|
| 15 | 1-(6,7-dihydro-5H-benzo[6,7]cyclohepta[1,2-c]pyridazin-3-yl)-N⁵-(1(2H)-oxo-3,4,5,6-tetrahydrobenzo[c]azocin-9-yl)-1H-1,2,4-triazole-3,5-diamine | H | (structure) | (structure) | H | H | B |

IC$_{50}$ activity:
A = <1 μM
B = 1 to 10 μM
C = >10 to 20 μM
D = >20 μM

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

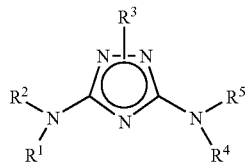

wherein:
$R^1$, $R^4$ and $R^5$ are independently selected from hydrogen, alkyl, aryl, aralkyl, —C(O)$R^9$ or —C(O)N($R^6$)$R^7$;
one of $R^2$ and $R^3$ is selected from one of the following and the other is selected from the other two of the following:
a) a bicyclic aryl of formula (II) or a bicyclic heteroaryl of formula (II):

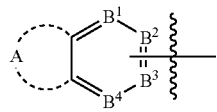

where:
A is an alkylene chain containing six to ten carbons, where one or two carbons of the alkylene chain is optionally replaced by —N$R^9$—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^8$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that one of $B^1$, $B^2$, $B^3$ and $B^4$ is a carbon directly bonded to the nitrogen to which its corresponding $R^2$ or $R^3$ is attached and that only one or two of $B^1$, $B^2$, $B^3$ and $B^4$ can be =N—;

b) a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); or c) a bridged bicyclic aryl of formula (III) or a bridged bicyclic heteroaryl of formula (III):

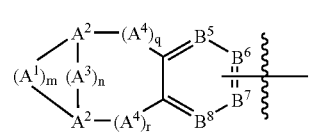

where:
m and n are independently 1 to 4;
q and r are independently 0 to 3;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);
each $A^2$ is independently selected from the group consisting of C($R^8$) and N;
$B^5$, $B^6$, $B^7$ and $B^8$ are each independently selected from the group consisting of =C($R^{13}$)— and =N—, provided that one of $B^5$, $B^6$, $B^7$ and $B^8$ is a carbon directly bonded to the nitrogen to which its corresponding $R^2$ or $R^3$ is attached;

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{11}-OR^9$, $-R^{11}-CN$, $-R^{11}-NO_2$, $-R^{11}-N(R^9)_2$, $R^{11}-C(O)OR^9$ and $-R^{11}-C(O)N(R^9)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), $-R^{10}-S(O)_tN(R^6)R^7$ (where t is 1 or 2), or two $R^8$'s on adjacent carbons can combine to form a double bond;

each $R^9$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl;

each $R^{10}$ is independently selected from the group consisting of a direct bond, an optionally substituted straight or branched alkylene chain, an optionally substituted straight or branched alkenylene chain and an optionally substituted straight or branched alkynylene chain;

each $R^{11}$ is independently selected from the group consisting of an optionally substituted straight or branched alkylene chain, an optionally substituted straight or branched alkenylene chain and an optionally substituted straight or branched alkynylene chain;

each $R^{12}$ is hydrogen, alkyl, cyano, nitro or $-OR^9$; and each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, $-R^{10}-OR^9$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2);

as an isolated stereoisomer or a mixture thereof, or as a pharmaceutically acceptable salt thereof.

2. The compound of claim 1 which is a compound of formula (Ia):

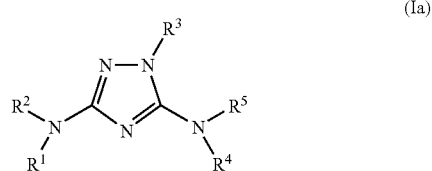

(Ia)

wherein:
$R^1$, $R^4$ and $R^5$ are independently selected from hydrogen, alkyl, aryl, aralkyl, $-C(O)R^9$ or $-C(O)N(R^6)R^7$;

one of $R^2$ and $R^3$ is selected from one of the following and the other is selected from the other two of the following:

a) a bicyclic aryl of formula (II) or a bicyclic heteroaryl of formula (II):

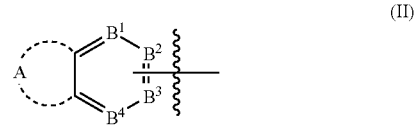

(II)

where:
A is an alkylene chain containing six to ten carbons, where one or two carbons of the alkylene chain is optionally replaced by $-NR^9-$, $=N-$, $-O-$, $-S(O)_p-$ (where p is 0, 1 or 2) or $-P(O)_p-$ (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to which its corresponding R$^2$ or R$^3$ is attached and that only one or two of B$^1$, B$^2$, B$^3$ and B$^4$ can be =N—;

b) a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); or c) a bridged bicyclic aryl of formula (III) or a bridged bicyclic heteroaryl of formula (III):

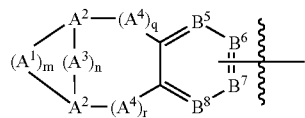
(III)

where:

m and n are independently 1 to 4;

q and r are independently 0 to 3;

each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);

each A$^2$ is independently selected from the group consisting of C(R$^8$) and N;

B$^5$, B$^6$, B$^7$ and B$^8$ are each independently selected from the group consisting of =C(R$^{13}$)— and =N—, provided that one of B$^5$, B$^6$, B$^7$ and B$^8$ is a carbon directly bonded to the nitrogen to which its corresponding R$^2$ or R$^3$ is attached;

each R$^6$ and R$^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{11}$—OR$^9$, —R$^{11}$—CN, —R$^{11}$—NO$_2$, —R$^{11}$—N(R$^9$)$_2$, —R$^{11}$—C(O)OR$^9$ and —R$^{11}$—C(O)N(R$^9$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), —R$^{10}$—S(O)$_t$N(R$^6$)R$^7$ (where t is 1 or 2), or two R$^8$'s on adjacent carbons can combine to form a double bond;

each R$^9$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl;

each R$^{10}$ is independently selected from the group consisting of a direct bond, an optionally substituted straight or branched alkylene chain, an optionally substituted straight or branched alkenylene chain and an optionally substituted straight or branched alkynylene chain;

each R$^{11}$ is independently selected from the group consisting of an optionally substituted straight or branched alkylene chain, an optionally substituted straight or branched alkenylene chain and an optionally substituted straight or branched alkynylene chain;

each R$^{12}$ is hydrogen, alkyl, cyano, nitro or —OR$^9$; and each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, —$R^{10}$—$OR^9$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2);

as an isolated stereoisomer or a mixture thereof, or as a pharmaceutically acceptable salt thereof.

3. The compound of claim 2 wherein:
$R^1$, $R^4$ and $R^5$ are each hydrogen;
$R^2$ is a bicyclic aryl of formula (II) or a bicyclic heteroaryl of formula (II):

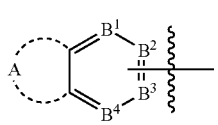

(II)

where:
A is an alkylene chain containing six to ten carbons, where one or two carbons of the alkylene chain is optionally replaced by —$NR^9$—, =N—, —O—, —$S(O)_p$— (where p is 0, 1 or 2) or —$P(O)_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—$O$—$R^{11}$—$OR^9$, —$R^{10}$—$O$—$R^{11}$—$O$—$R^{11}$—$OR^9$, —$R^{10}$—$O$—$R^{11}$—$CN$, —$R^{10}$—$O$—$R^{11}$—$C(O)OR^9$, —$R^{10}$—$O$—$R^{11}$—$C(O)N(R^6)R^7$, —$R^{10}$—$O$—$R^{11}$—$S(O)_pR^9$ (where p is 0, 1 or 2), —$R^{10}$—$O$—$R^{11}$—$N(R^6)R^7$, —$R^{10}$—$O$—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and $B^1$, $B^2$, $B^3$ and $B^4$ are each independently selected from the group consisting of =$C(R^{13})$— and =N—, provided that one of $B^1$, $B^2$, $B^3$ and $B^4$ is a carbon directly bonded to the nitrogen to which $R^2$ is attached and that only one or two of $B^1$, $B^2$, $B^3$ and $B^4$ can be =N—; and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—$OR^9$, —$R^{10}$—$O$—$R^{11}$—$OR^9$, —$R^{10}$—$O$—$R^{11}$—$O$—$R^{11}$—$OR^9$, —$R^{10}$—$O$—$R^{11}$—$CN$, —$R^{10}$—$O$—$R^{11}$—$C(O)OR^9$, —$R^{10}$—$O$—$R^{11}$—$C(O)N(R^6)R^7$, —$R^{10}$—$O$—$R^{11}$—$S(O)_pR^9$ (where p is 0, 1 or 2), —$R^{10}$—$O$—$R^{11}$—$N(R^6)R^7$, —$R^{10}$—$O$—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2).

4. The compound of claim 3 wherein:
$R^1$, $R^4$ and $R^5$ are each hydrogen;
$R^2$ is a bicyclic aryl of formula (II):

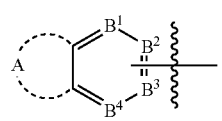

(II)

where:
A is an alkylene chain containing six carbons where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—$O$—$R^{11}$—$OR^9$, —$R^{10}$—$O$—$R^{11}$—$O$—$R^{11}$—$OR^9$, —$R^{10}$—$O$—$R^{11}$—$CN$, —$R^{10}$—$O$—$R^{11}$—$C(O)OR^9$, —$R^{10}$—$O$—$R^{11}$—$C(O)N(R^6)R^7$, —$R^{10}$—$O$—$R^{11}$—$S(O)_pR^9$ (where p is 0, 1 or 2), —$R^{10}$—$O$—$R^{11}$—$N(R^6)R^7$, —$R^{10}$—$O$—$R^{11}$—$C(NR^{12})N(R^{12})H$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2); and B¹, B², B³ and B⁴ are each independently =C(R¹³)—, provided that one of B¹, B², B³ and B⁴ is a carbon directly bonded to the nitrogen to which R² is attached; and R³ is polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R¹⁰—OR⁹, —R¹⁰—O—R¹¹—OR⁹, —R¹⁰—O—R¹¹—O—R¹¹—OR⁹, —R¹⁰—O—R¹¹—CN, —R¹⁰—O—R¹¹—C(O)OR⁹, —R¹⁰—O—R¹¹—C(O)N(R⁶)R⁷, —R¹⁰—O—R¹¹—S(O)$_p$R⁹ (where p is 0, 1 or 2), —R¹⁰—O—R¹¹—N(R⁶)R⁷, —R¹⁰—O—R¹¹—C(NR¹²)N(R¹²)H, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁹, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2).

5. The compound of claim 4 wherein:
R¹, R⁴ and R⁵ are each hydrogen;
R² is a bicyclic aryl of formula (II):

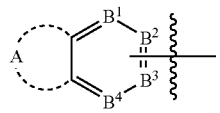

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R⁶, —R¹⁰—OR⁹, —R¹⁰—OC(O)—R⁹, —R¹⁰—N(R⁶)R⁷, —R¹⁰—C(O)R⁹, —R¹⁰—C(O)OR⁹, —R⁹, —R¹⁰—C(O)N(R⁶)R⁷, —R¹⁰—N(R⁶)C(O)OR⁹, —R¹⁰—N(R⁶)C(O)$_R$⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2); and B¹, B², B³ and B⁴ are each independently =C(R¹³)—, provided that one of B¹, B², B³ and B⁴ is a carbon directly bonded to the nitrogen to which R² is attached; and R³ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, —R¹⁰—OR⁹, —R¹⁰—OC(O)—R⁹, —R¹⁰—N(R⁶)R⁷, —R¹⁰—C(O)R⁹, —R¹⁰—C(O)OR⁹, —R¹⁰—C(O)N(R⁶)R⁷, —R¹⁰—N(R⁶)C(O)OR⁹, —R¹⁰—N(R⁶)C(O)R⁹, —R¹⁰—N(R⁶)S(O)$_t$R⁹ (where t is 1 or 2), —R¹⁰—S(O)$_t$OR⁹ (where t is 1 or 2), —R¹⁰—S(O)$_p$R⁹ (where p is 0, 1 or 2), and —R¹⁰—S(O)$_t$N(R⁶)R⁷ (where t is 1 or 2).

6. The compound of claim 5, which is 1-(6,7-dihydro-5H-benzo[6,7]cyclohepta[1,2-c]pyridazin-3-yl)-N³-(6-pyrrolidin-1-yl-5,6,7,8,9,10-hexahydrobenzo[8]annulene-3-yl)-1H-1,2,4-triazole-3,5-diamine.

7. The compound of claim 3 wherein:
R¹, R⁴ and R⁵ are each hydrogen;
R² is a bicyclic heteroaryl of formula (II):

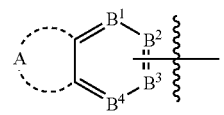

(II)

where:
A is an alkylene chain containing six carbons, where each carbon of the alkylene chain may be replaced by —N(R⁹)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R⁶, —R¹⁰—OR⁹, —R¹⁰—O—R¹¹—OR⁹, —R¹⁰—O—R¹¹—O—R¹¹—OR⁹, —R¹⁰—O—R¹¹—CN, —R¹⁰—O—R¹¹—C(O)OR⁹, —R¹⁰—O—R¹¹—C(O)N(R⁶)R⁷, —$R^{10}$—O—$R^{11}$—S(O)$_p$R$^9$ (where p is 0, 1 or 2), —$R^{10}$—O—$R^{11}$—N(R$^6$)R$^7$, —$R^{10}$—O—$R^{11}$—C(NR$^{12}$)N(R$^{12}$)H, —$R^{10}$—OC(O)—R$^9$, —$R^{10}$—N(R$^6$)R$^7$, —$R^{10}$—C(O)R$^9$, —$R^{10}$—C(O)OR$^9$, —$R^{10}$—C(O)N(R$^6$)R$^7$, —$R^{10}$—N(R$^6$)C(O)OR$^9$, —$R^{10}$—N(R$^6$)C(O)R$^9$, —$R^{10}$—N(R$^6$)S(O)$_t$R$^9$ (where t is 1 or 2), —$R^{10}$—S(O)$_t$OR$^9$ (where t is 1 or 2), —$R^{10}$—S(O)$_p$R$^9$ (where p is 0, 1 or 2), and —$R^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, one of B$^1$, B$^2$, B$^3$ and B$^4$ is a carbon directly bonded to the nitrogen to which R$^2$ is attached and that only one or two of B$^1$, B$^2$, B$^3$ and B$^4$ can be =N—; and R$^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,T-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—OR$^9$, —$R^{10}$—O—$R^{11}$—OR$^9$, —$R^{10}$—O—$R^{11}$—O—$R^{11}$—OR$^9$, —$R^{10}$—O—$R^{11}$—CN, —$R^{10}$—O—$R^{11}$—C(O)OR$^9$, —$R^{10}$—O—$R^{11}$—C(O)N(R$^6$)R$^7$, —$R^{10}$—O—$R^{11}$—S(O)$_p$R$^9$ (where p is 0, 1 or 2), —$R^{10}$—O—$R^{11}$—N(R$^6$)R$^7$, —$R^{10}$—O—$R^{11}$—C(NR$^{12}$)N(R$^{12}$)H, —$R^{10}$—OC(O)—R$^9$, —$R^{10}$—N(R$^6$)R$^7$, —$R^{10}$—C(O)R$^9$, —$R^{10}$—C(O)OR$^9$, —$R^{10}$—C(O)N(R$^6$)R$^7$, —$R^{10}$—N(R$^6$)C(O)OR$^9$, —$R^{10}$—N(R$^6$)C(O)R$^9$, —$R^{10}$—N(R$^6$)S(O)$_t$R$^9$ (where t is 1 or 2), —$R^{10}$—S(O)$_t$OR$^9$ (where t is 1 or 2), —$R^{10}$—S(O)$_p$R$^9$ (where p is 0, 1 or 2), and —$R^{10}$—S(O)$_t$N(R$^6$)R$^7$ (where t is 1 or 2).

8. The compound of claim 7 wherein:

R$^1$, R$^4$ and R$^5$ are each hydrogen;

R$^2$ is a bicyclic heteroaryl of formula (II):

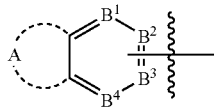

(II)

where:

A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —$R^{10}$—OR$^9$, —$R^{10}$—OC(O)—R$^9$, —$R^{10}$—N(R$^6$)R$^7$, —$R^{10}$—C(O)R$^9$, —$R^{10}$—C(O)OR$^9$, —$R^{10}$—C(O)N(R$^6$)R$^7$, —$R^{10}$—N(R$^6$)C(O)OR$^9$, —$R^{10}$—N(R$^6$)C(O)R$^9$, —$R^{10}$—N(R$^6$)S(O)$_t$R$^9$ (where t is 1 or 2), —$R^{10}$—S(O)$_t$OR$^9$ (where t is 1 or 2), —$R^{10}$—S(O)$_p$R$^9$ (where p is 0, 1 or 2), and —$R^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— or =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—OR$^9$, —$R^{10}$—OC(O)—R$^9$, —$R^{10}$—N(R$^6$)R$^7$, —$R^{10}$—C(O)R$^9$, —$R^{10}$—C(O)OR$^9$, —$R^{10}$—C(O)N(R$^6$)R$^7$, —$R^{10}$—N(R$^6$)C(O)OR$^9$, —$R^{10}$—N(R$^6$)C(O)R$^9$, —$R^{10}$—N(R$^6$)S(O)$_t$R$^9$ (where t is 1 or 2), —$R^{10}$—S(O)$_t$OR$^9$ (where t is 1 or 2), —$R^{10}$—S(O)$_p$R$^9$ (where p is 0, 1 or 2), and —$R^{10}$—S(O)$_t$N(R$^6$)R$^7$ (where t is 1 or 2).

9. The compound of claim 8 wherein:

R$^1$, R$^4$ and R$^5$ are each hydrogen;

R$^2$ is a bicyclic heteroaryl of formula (II):

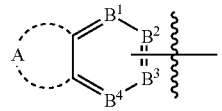

(II)

where:
A is an alkylene chain containing six carbons, where at least one carbon is replaced by —N(R$^9$)— and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

10. The compound of claim 9 selected from the group consisting of:

1-(6,7-dihydro-5H-benzo[6,7]cyclohepta[1,2-c]pyridazin-3-yl)-N$^3$-(4(1H)-oxo-2,3,5,6-tetrahydrobenzo[d]azocin-8-yl)-1H-1,2,4-triazole-3,5-diamine;

1-(6,7-dihydro-5H-benzo[6,7]cyclohepta[1,2-c]pyridazin-3-yl)-N$^3$-(3-cyclopentyl-1,2,3,4,5,6-hexahydrobenzo[d]azocin-8-yl)-1H-1,2,4-triazole-3,5-diamine;

1-(6,7-dihydro-5H-benzo[6,7]cyclohepta[1,2-c]pyridazin-3-yl)-N$^3$-(3-cyclopentyl-1,2,3,4,5,6-hexahydrobenzo[d]azocin-9-yl)-1H-1,2,4-triazole-3,5-diamine;

1-(6,7-dihydro-5H-benzo[6,7]cyclohepta[1,2-c]pyridazin-3-yl)-N$^3$-(1(2H)-oxo-3,4,5,6-tetrahydrobenzo[c]azocin-9-yl)-1H-1,2,4-triazole-3,5-diamine;

1-(6,7-dihydro-5H-benzo[6,7]cyclohepta[1,2-c]pyridazin-3-yl)-N$^3$-(1(2H)-oxo-3,4,5,6-tetrahydrobenzo[c]azocin-9-yl)-1H-1,2,4-triazole-3,5-diamine;

1-(6,7-dihydro-5H-benzo[6,7]cyclohepta[1,2-c]pyridazin-3-yl)-N$^3$-(1,2,3,4,5,6-hexahydrobenzo[c]azocin-9-yl)-1H-1,2,4-triazole-3,5-diamine.

11. The compound of claim 8 wherein:
R$^1$, R$^4$ and R$^5$ are each hydrogen;
R$^2$ is a bicyclic heteroaryl of formula (II):

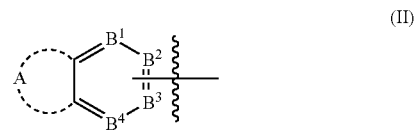

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one of B$^1$, B$^2$, B$^3$ and B$^4$ is =N—, one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)

S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

12. The compound of claim 11 selected from the group consisting of:

1-(6,7-dihydro-5H-benzo[6,7]cyclohepta[1,2-c]pyridazin-3-yl)-N$^3$-(7-oxo-5,6,8,9,10-pentahydrocycloocta[b]pyridin-3-yl)-1H-1,2,4-triazole-3,5-diamine;

1-(6,7-dihydro-5H-benzo[6,7]cyclohepta[1,2-c]pyridazin-3-yl)-N$^3$-(7-(pyrrolidin-1-yl)-5,6,7,8,9,10-hexahydrocycloocta[b]pyridin-3-yl)-1H-1,2,4-triazole-3,5-diamine;

1-(6,7-dihydro-5H-benzo[6,7]cyclohepta[1,2-c]pyridazin-3-yl)-N$^3$-(7-(methoxyimino)-5,6,7,8,9,10-hexahydrocycloocta[b]pyridin-3-yl)-1H-1,2,4-triazole-3,5-diamine; and 1-(6,7-dihydro-5H-benzo[6,7]cyclohepta[1,2-c]pyridazin-3-yl)-N$^3$-(7-hydroxy-5,6,7,8,9,10-hexahydrocycloocta[b]pyridin-3-yl)-1H-1,2,4-triazole-3,5-diamine.

13. The compound of claim 2 wherein:
R$^1$, R$^4$ and R$^5$ are each hydrogen;
R$^2$ is a bicyclic aryl of formula (II) or a bicyclic heteroaryl of formula (II):

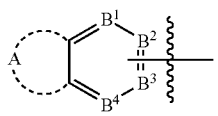

(II)

where:
A is an alkylene chain containing six to ten carbons, where one or two carbons of the alkylene chain is optionally replaced by —NR$^9$—, =N—, —O—, —S(O)$_p$— (where p is 0, 1 or 2) or —P(O)— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to which R$^2$ is attached and that only one or two of B$^1$, B$^2$, B$^3$ and B$^4$ can be =N—; and R$^3$ is a bridged bicyclic aryl of formula (III) or a bridged bicyclic heteroaryl of formula (III):

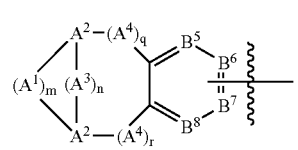

(III)

where:
m and n are independently 1 to 2;
q and r are independently 0 to 3;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that one of B$^5$, B$^6$, B$^7$ and B$^8$ is a carbon directly bonded to the nitrogen to which R$^3$ is attached.

14. The compound of claim 13 wherein:
R$^1$, R$^4$ and R$^5$ are each hydrogen;
R$^2$ is a bicyclic aryl of formula (II):

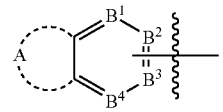

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—; provided that one of B$^1$, B$^2$, B$^3$ and B$^4$ is a carbon directly bonded to the nitrogen to which R$^2$ is attached; and R$^3$ is a bridged bicyclic aryl of formula (III):

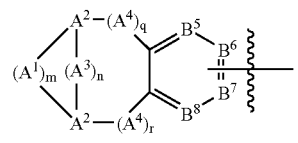

(III)

where:
  m and n are independently 1 to 2;
  q and r are independently 0 to 2;
  each $A^1$, $A^3$ and $A^4$ is independently $C(R^8)_2$;
  each $A^2$ is independently $C(R^8)$;
  $B^5$, $B^6$, $B^7$ and $B^8$ are each independently $=C(R^{13})-$, provided that one of $B^5$, $B^6$, $B^7$ and $B^8$ is a carbon directly bonded to the nitrogen to which $R^3$ is attached.

15. The compound of claim 14 wherein:
  $R^1$, $R^4$ and $R^5$ are each hydrogen;
  $R^2$ is a bicyclic aryl of formula (II):

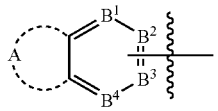
(II)

where:
  A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and
  $B^1$, $B^2$, $B^3$ and $B^4$ are each independently $=C(R^{13})-$; provided that one of $B^1$, $B^2$, $B^3$ and $B^4$ is a carbon directly bonded to the nitrogen to which $R^2$ is attached; and
  $R^3$ is a bridged bicyclic aryl of formula (III):

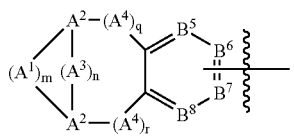
(III)

where:
  m and n are independently 1 to 2;
  q and r are independently 0 to 2;
  each $A^1$, $A^3$ and $A^4$ is independently $C(R^8)_2$;
  each $A^2$ is independently $C(R^8)$;
  $B^5$, $B^6$, $B^7$ and $B^8$ are each independently $=C(R^{13})-$, provided that one of $B^5$, $B^6$, $B^7$ and $B^8$ is a carbon directly bonded to the nitrogen to which $R^3$ is attached.

16. The compound of claim 13 wherein:
  $R^1$, $R^4$ and $R^5$ are each hydrogen;
  $R^2$ is a bicyclic aryl of formula (II):

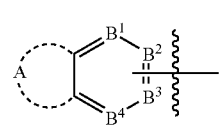
(II)

where:
  A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{11}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and
  $B^1$, $B^2$, $B^3$ and $B^4$ are each independently $=C(R^{13})-$, provided that one of $B^1$, $B^2$, $B^3$ and $B^4$ is a carbon directly bonded to the nitrogen to which $R^2$ is attached; and
  $R^3$ is a bridged bicyclic heteroaryl of formula (III):

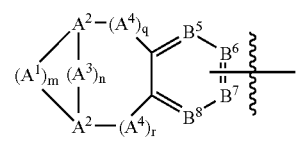
(III)

where:
  m and n are independently 1 to 2;
  q and r are independently 0 to 2;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $=C(R^8)-$ and $=N-$;
  $B^5$, $B^6$, $B^7$ and $B^8$ are each independently selected from the group consisting of $=C(R^{13})-$ and $=N-$, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is $=N-$ or one of $B^5$, $B^6$, $B^7$ and $B^8$ is $=N-$, and one of $B^5$, $B^6$, $B^7$ and $B^8$ is a carbon directly bonded to the nitrogen to which $R^3$ is attached.

17. The compound of claim 16 wherein:
$R^1$, $R^4$ and $R^5$ are each hydrogen;
$R^2$ is a bicyclic aryl of formula (II):

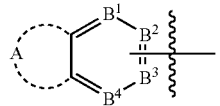
(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
$B^1$, $B^2$, $B^3$ and $B^4$ are each independently =C($R^{13}$)—, provided that one of $B^1$, $B^2$, $B^3$ and $B^4$ is a carbon directly bonded to the nitrogen to which $R^2$ is attached; and
$R^3$ is a bridged bicyclic heteroaryl of formula (III):

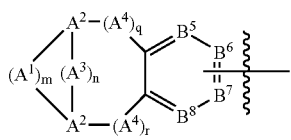
(III)

where:
m and n are independently 1 to 2;
q and r are independently 0 to 2;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);
each $A^2$ is independently selected from the group consisting of =C($R^8$)— and =N—;
$B^5$, $B^6$, $B^7$ and $B^8$ are each independently selected from the group consisting of =C($R^{13}$)— and =N—, provided that at least one of $A^1$, $A^3$ and $A^4$ is independently selected from the group consisting of O, S(O)$_p$ (where p is 0, 1 or 2), P(O)$_p$ (where p is 0, 1 or 2) and N($R^9$), or $A^3$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached.

18. The compound of claim 13 wherein:
$R^1$, $R^4$ and $R^5$ are each hydrogen;
$R^2$ is a bicyclic heteroaryl of formula (II):

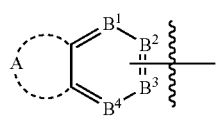
(II)

where:
A is an alkylene chain containing six carbons, where each carbon of the alkylene chain may be replaced by —N($R^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
$B^1$, $B^2$, $B^3$ and $B^4$ are each independently selected from the group consisting of =C($R^{13}$)— and =N—, provided that at least one carbon in A is replaced with —N($R^9$)—, —O—, —S(O)$_p$— (where p is 0, 1 or 2) or —P(O)$_p$— (where p is 0, 1 or 2) or one of $B^1$, $B^2$, $B^3$ and $B^4$ is =N—, one of $B^1$, $B^2$, $B^3$ and $B^4$ is a carbon directly bonded to the nitrogen to $R^2$ is attached and that only one or two of $B^1$, $B^2$, $B^3$ and $B^4$ can be =N—; and
$R^3$ is a bridged bicyclic aryl of formula (III):

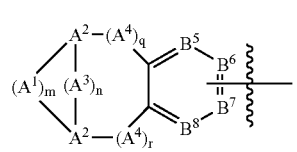
(III)

where:
m and n are independently 1 to 2;
q and r are independently 0 to 2;
each $A^1$, $A^3$ and $A^4$ is independently C($R^8$)$_2$;
each $A^2$ is independently C($R^8$);
$B^5$, $B^6$, $B^7$ and $B^8$ are each independently =C($R^{13}$)—, provided that one of $B^5$, $B^6$, $B^7$ and $B^8$ is a carbon directly bonded to the nitrogen to which $R^3$ is attached.

19. The compound of claim 18 wherein:
$R^1$, $R^4$ and $R^5$ are each hydrogen;
$R^2$ is a bicyclic heteroaryl of formula (II):

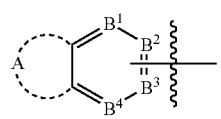
(II)

where:
A is an alkylene chain containing six carbons, where each carbon of the alkylene chain may be replaced by —N($R^9$)—, =N—, —O—, —S(O)$_p$— (where p is 0, 1 or 2) or —P(O)— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that at least one carbon in A is replaced with —N($R^9$)—, —O—, —S(O)$_p$— (where p is 0, 1 or 2) or —P(O)$_p$— (where p is 0, 1 or 2) or one of $B^1$, $B^2$, $B^3$ and $B^4$ is =N—, one of $B^1$, $B^2$, $B^3$ and $B^4$ is a carbon directly bonded to the nitrogen to which $R^2$ is attached and that only one or two of $B^1$, $B^2$, $B^3$ and $B^4$ can be =N—; and $R^3$ is a bridged bicyclic aryl of formula (III):

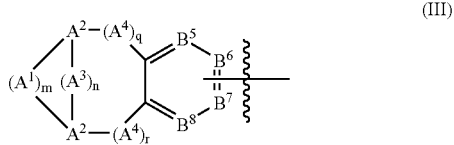

(III)

where:
m and n are independently 1 to 2;
q and r are independently 0 to 2;
each $A^1$, $A^3$ and $A^4$ is independently C($R^8$)$_2$;
each $A^2$ is independently C($R^8$);
$B^5$, $B^6$, $B^7$ and $B^8$ are each independently =C($R^{13}$)—, provided that one of $B^5$, $B^6$, $B^7$ and $B^8$ is a carbon directly bonded to the nitrogen to which $R^3$ is attached.

20. The compound of claim 13 wherein:
$R^1$, $R^4$ and $R^5$ are each hydrogen;
$R^2$ is a bicyclic heteroaryl of formula (II):

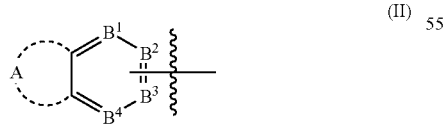

(II)

where:
A is an alkylene chain containing six carbons, where each carbon of the alkylene chain or alkenylene chain may be replaced by —N($R^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that at least one carbon in A is replaced with —N($R^9$)—, =N—, —O—, —S(O)$_p$— (where p is 0, 1 or 2) or —P(O)$_p$— (where p is 0, 1 or 2) or one of $B^1$, $B^2$, $B^3$ and $B^4$ is =N—, one of $B^1$, $B^2$, $B^3$ and $B^4$ is a carbon directly bonded to the nitrogen to $R^2$ is attached and that only one or two of $B^1$, $B^2$, $B^3$ and $B^4$ can be =N—; and $R^3$ is a bridged bicyclic heteroaryl of formula (III):

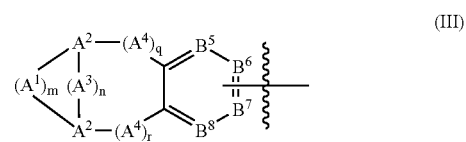

(III)

where:
m and n are independently 1 to 2;
q and r are independently 0 to 2;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);
each $A^2$ is independently selected from the group consisting of C($R^8$) and N;
$B^5$, $B^6$, $B^7$ and $B^8$ are each independently =C($R^{13}$)— or =N—, provided that at least one of $A^1$, $A^3$ and $A^4$ is independently selected from the group consisting of O, S(O)$_p$ (where p is 0, 1 or 2), P(O)$_p$ (where p is 0, 1 or 2) and N($R^9$), or $A^3$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached.

21. The compound of claim 20 wherein:
$R^1$, $R^4$ and $R^5$ are each hydrogen;
$R^2$ is a bicyclic heteroaryl of formula (II):

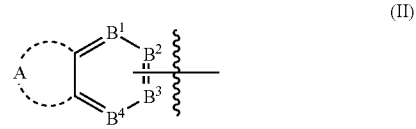

(II)

where:
A is an alkylene chain containing six carbons, where each carbon of the alkylene chain may be replaced by —N(R$^9$)—, =N—, —O—, —S(O)$_p$— (where p is 0, 1 or 2) or —P(O)— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—; and R$^3$ is a bridged bicyclic heteroaryl of formula (III):

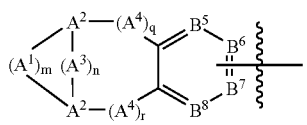

(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— or =N—, provided that at least one of A$^1$, A$^3$ and A$^4$ is independently selected from O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached.

22. The compound of claim 21 wherein:
R$^1$, R$^4$ and R$^5$ are each hydrogen;
R$^2$ is a bicyclic heteroaryl of formula (II):

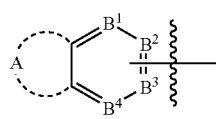

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one of B$^1$, B$^2$, B$^3$ and B$^4$ is =N—, one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—; and R$^3$ is a bridged bicyclic heteroaryl of formula (III):

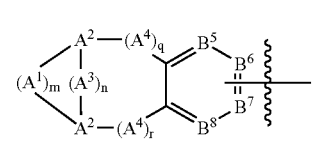

(III)

where:
m and n are independently 1 to 2;
q and r are independently 0 to 2;
each A$^1$, A$^3$ and A$^4$ is independently C(R$^8$)$_2$;
each A$^2$ is independently selected from the group consisting of C(R$^8$) and N;
B$^5$, B$^6$, B$^7$ and B$^8$ are each independently selected from the group consisting of =C(R$^{13}$)— or =N—, provided that at least one A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached.

23. The compound of claim 22 which is 1-(1,4-ethano-8-pyridin-4-yl-1,2,3,4-tetrahydro-1,5-naphthyridin-6-yl)-N$^3$-(7-oxo-5,6,7,8,9,10-hexahydrocycloocta[b]pyridin-3-yl)-1H-1,2,4-triazole-3,5-diamine.

24. The compound of claim 2 wherein:
R$^1$, R$^4$ and R$^5$ are each hydrogen;
R$^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2); and $R^3$ is a bicyclic aryl of formula (II) or a bicyclic heteroaryl of formula (II):

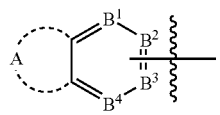

(II)

where:

A is an alkylene chain containing six to ten carbons, where each carbon of the alkylene chain may be replaced by —N($R^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that one of $B^1$, $B^2$, $B^3$ and $B^4$ is a carbon directly bonded to the nitrogen to which $R^3$ is attached and that only one or two of $B^1$, $B^2$, $B^3$ and $B^4$ can be =N—.

25. The compound of claim 24 wherein:

$R^1$, $R^4$ and $R^5$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2); and $R^3$ is a bicyclic aryl of formula (II):

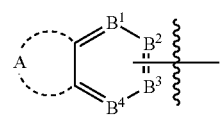

(II)

where:

A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently =C($R^{13}$)—, provided that one of $B^1$, $B^2$, $B^3$ and $B^4$ is a carbon directly bonded to the nitrogen to which $R^3$ is attached.

26. The compound of claim 25 wherein:

$R^1$, $R^4$ and $R^5$ are each hydrogen;

$R^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bicyclic aryl of formula (II):

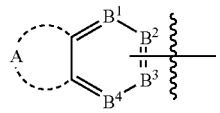

(II)

where:

A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently =C($R^{13}$)—, provided that one of $B^1$, $B^2$, $B^3$ and $B^4$ is a carbon directly bonded to the nitrogen to which $R^3$ is attached.

27. The compound of claim 24 wherein:

$R^1$, $R^4$ and $R^5$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bicyclic heteroaryl of formula (II):

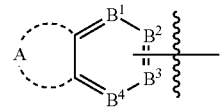

(II)

where:

A is an alkylene chain containing six carbons, where each carbon of the alkylene chain may be replaced by —N($R^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that at least one carbon in A is replaced with —N($R^9$)—, =N—, —O—, —S(O)$_p$— (where p is 0, 1 or 2) or —P(O)$_p$— (where p is 0, 1 or 2) or one of $B^1$, $B^2$, $B^3$ and $B^4$ is =N—, one of $B^1$, $B^2$, $B^3$ and $B^4$ is a carbon directly bonded to the nitrogen to $R^2$ is attached and that only one or two of $B^1$, $B^2$, $B^3$ and $B^4$ can be =N—.

28. The compound of claim 27 wherein:

$R^1$, $R^4$ and $R^5$ are each hydrogen;

$R^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bicyclic heteroaryl of formula (II):

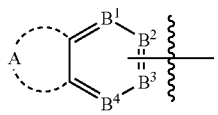

(II)

where:

A is an alkylene chain containing six carbons, where each carbon of the alkylene chain may be replaced by —N($R^9$)—, =N—, —O—, —S(O)$_p$— (where p is 0, 1 or 2) or —P(O)$_p$-(where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that at least one carbon in A is replaced with —N($R^9$)—, =N—, —O—, —S(O)$_p$— (where p is 0, 1 or 2) or —P(O)$_p$— (where p is 0, 1 or 2) or one of $B^1$, $B^2$, $B^3$ and $B^4$ is =N—, one of $B^1$, $B^2$, $B^3$ and $B^4$ is a carbon directly bonded to the nitrogen to $R^2$ is attached and that only one or two of $B^1$, $B^2$, $B^3$ and $B^4$ can be =N—.

29. The compound of claim 28 wherein:

$R^1$, $R^4$ and $R^5$ are each hydrogen;

$R^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bicyclic heteroaryl of formula (II):

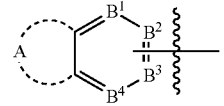

(II)

where:

A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that at least one of $B^1$, $B^2$, $B^3$ and $B^4$ is =N—, one of $B^1$, $B^2$, $B^3$ and $B^4$ is a carbon directly bonded to the nitrogen to $R^2$ is attached and that only one or two of $B^1$, $B^2$, $B^3$ and $B^4$ can be =N—.

30. The compound of claim 29 which is 1-(5,6,7,8,9,10-hexahydrocycloocta[d]pyrimidin-4-yl)-$N^3$-(5,6,8,9-tetrahydrospiro[benzo[7]annulene-7,2'-[1,3]dioxolane]-3-yl)-1H-1,2,4-triazole-3,5-diamine.

31. The compound of claim 2 wherein:
$R^1$, $R^4$ and $R^5$ are each hydrogen;
$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bridged bicyclic aryl of formula (III) or a bridged bicyclic heteroaryl of formula (III):

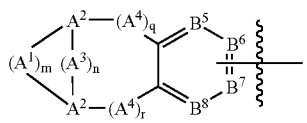

(III)

where:
m and n are independently 1 to 2;
q and r are independently 0 to 3;
each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);
each $A^2$ is independently selected from the group consisting of C($R^8$) or N;
$B^5$, $B^6$, $B^7$ and $B^8$ are each independently =C($R^{13}$)— or =N—, provided that one of $B^5$, $B^6$, $B^7$ and $B^8$ is a carbon directly bonded to the nitrogen to which $R^3$ is attached.

32. The compound of claim 31 wherein:
$R^1$, $R^4$ and $R^5$ are each hydrogen;
$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[V][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bridged bicyclic aryl of formula (III):

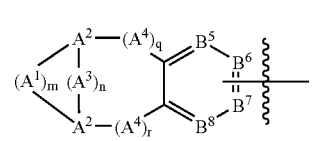

(III)

where:
m and n are independently 1 to 2;
q and r are independently 0 to 2;
each $A^1$, $A^3$ and $A^5$ is independently C($R^8$)$_2$;
each $A^2$ is independently C($R^8$);
$B^5$, $B^6$, $B^7$ and $B^8$ are each independently =C($R^{13}$)—, provided that one of $B^5$, $B^6$, $B^7$ and $B^8$ is a carbon directly bonded to the nitrogen to which $R^3$ is attached.

33. The compound of claim 32 wherein:

$R^1$, $R^4$ and $R^5$ are each hydrogen;

$R^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bridged bicyclic aryl of formula (III):

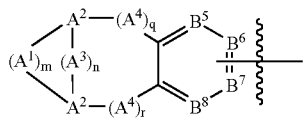

(III)

where:

m and n are independently 1 to 2;

q and r are independently 0 to 2;

each $A^1$, $A^3$ and $A^4$ is independently C($R^8$)$_2$;

each $A^2$ is independently C($R^8$);

$B^5$, $B^6$, $B^7$ and $B^8$ are each independently =C($R^{13}$)—, provided that one of $B^5$, $B^6$, $B^7$ and $B^8$ is a carbon directly bonded to the nitrogen to which $R^3$ is attached.

34. The compound of claim 31 wherein:

$R^1$, $R^4$ and $R^5$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and $R^3$ is a bridged bicyclic heteroaryl of formula (III):

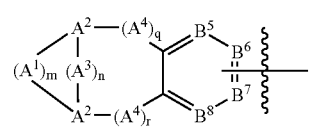

(III)

where:

m and n are independently 1 to 2;

q and r are independently 0 to 2;

each $A^1$, $A^3$ and $A^4$ is independently selected from the group consisting of C($R^8$)$_2$, O, S(O)$_p$ (where p is 0, 1 or 2), P(O)$_p$ (where p is 0, 1 or 2) and N($R^9$);

each $A^2$ is independently selected from the group consisting of C($R^8$) and N;

$B^5$, $B^6$, $B^7$ and $B^8$ are each independently selected from the group consisting of =C($R^{13}$)— and =N—, provided that at least one of $A^1$, $A^3$ and $A^4$ is independently selected from the group consisting of O, S(O)$_p$ (where p is 0, 1 or 2), P(O)$_p$ (where p is 0, 1 or 2) and N($R^9$), or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached.

35. The compound of claim 34 wherein:

$R^1$, $R^4$ and $R^5$ are each hydrogen;

$R^2$ is selected from the group consisting of 6,7-dihydro-5H-benzo[6,7]cyclohepta[1,2-c]pyridazin-3-yl, 6,7-dihydro-5H-benzo[6,7]cyclohepta[1,2-a]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and R$^3$ is a bridged bicyclic heteroaryl of formula (III):

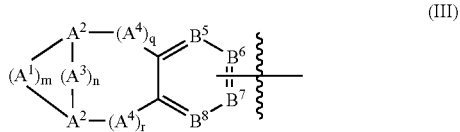

(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) or N;
B$^5$, B$^6$, B$^7$ and B$^8$ are each independently selected from the group consisting of =C(R$^{13}$)— and =N—, provided that at least one of A$^1$, A$^3$ and A$^4$ is independently selected from the group consisting of O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached.

36. The compound of claim 2 wherein:
R$^1$, R$^4$ and R$^5$ are each hydrogen;
R$^2$ is a bridged bicyclic aryl of formula (III) or a bridged bicyclic heteroaryl of formula (III):

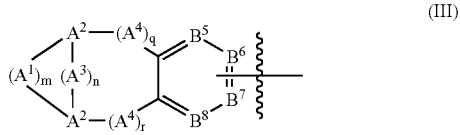

(III)

where:
m and n are independently 1 to 2;
q and r are independently 0 to 3;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that one of B$^5$, B$^6$, B$^7$ and B$^8$ is a carbon directly bonded to the nitrogen to which R$^2$ is attached; and R$^3$ is a bicyclic aryl of formula (II) or a bicyclic heteroaryl of formula (II):

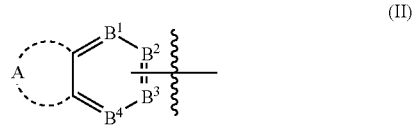

(II)

where:
A is an alkylene chain containing six to ten carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to which R$^3$ is attached and that only one or two of B$^1$, B$^2$, B$^3$ and B$^4$ can be =N—.

37. The compound of claim 36 wherein:
R$^1$, R$^4$ and R$^5$ are each hydrogen;
R$^2$ is a bridged bicyclic aryl of formula (III):

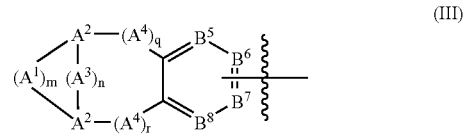

(III)

where:
m and n are independently 1 to 2;
q and r are independently 0 to 2;
each A$^1$, A$^3$ and A$^4$ is independently C(R$^8$)$_2$;
each A$^2$ is independently C(R$^8$);
B$^5$, B$^6$, B$^7$ and B$^8$ are each independently =C(R$^{13}$)—, provided that one of B$^5$, B$^6$, B$^7$ and B$^8$ is a carbon directly bonded to the nitrogen to which R$^2$ is attached; and R$^3$ is a bicyclic aryl of formula (II):

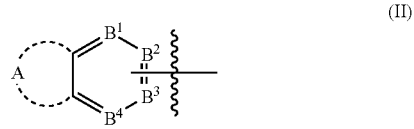

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $B^1$, $B^2$, $B^3$ and $B^4$ are each independently $=C(R^{13})-$, provided that one of $B^1$, $B^2$, $B^3$ and $B^4$ is a carbon directly bonded to the nitrogen to which $R^3$ is attached.

38. The compound of claim 37 wherein:
$R^1$, $R^4$ and $R^5$ are each hydrogen;
$R^2$ is a bridged bicyclic aryl of formula (III):

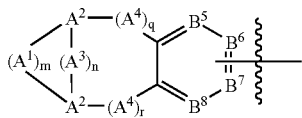

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently $=C(R^{13})-$, provided that one of $B^5$, $B^6$, $B^7$ and $B^8$ is a carbon directly bonded to the nitrogen to which $R^2$ is attached; and
$R^3$ is a bicyclic aryl of formula (II):

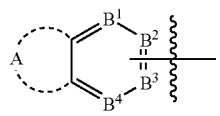

(II)

where:
A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $B^1$, $B^2$, $B^3$ and $B^4$ are each independently $=C(R^{13})-$, provided that one of $B^1$, $B^2$, $B^3$ and $B^4$ is a carbon directly bonded to the nitrogen to which $R^3$ is attached.

39. The compound of claim 36 wherein:
$R^1$, $R^4$ and $R^5$ are each hydrogen;
$R^2$ is a bridged bicyclic aryl of formula (III):

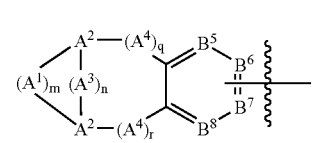

(III)

where:
m and n are independently 1 to 2;
q and r are independently 0 to 2;
each $A^1$, $A^3$ and $A^4$ is independently $C(R^8)_2$;
each $A^2$ is independently $C(R^8)$;
$B^5$, $B^6$, $B^7$ and $B^8$ are each independently $=C(R^{13})-$, provided that one of $B^5$, $B^6$, $B^7$ and $B^8$ is a carbon directly bonded to the nitrogen to which $R^2$ is attached; and
$R^3$ is a bicyclic heteroaryl of formula (II):

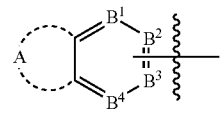

(II)

where:
A is an alkylene chain containing six carbons, where each carbon of the alkylene chain may be replaced by $-N(R^9)-$, $=N-$, $-O-$, $-S(O)_p-$ (where p is 0, 1 or 2) or $-P(O)_p-$ (where p is 0, 1 or 2) and where each carbon in the alkylene chain or the alkenylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $B^1$, $B^2$, $B^3$ and $B^4$ are each independently selected from the group consisting of $=C(R^{13})-$ and $=N-$, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, one of B$^1$, B$^2$, B$^3$ and B$^4$ is a carbon directly bonded to the =N—.

40. The compound of claim 39 wherein:

R$^1$, R$^4$ and R$^5$ are each hydrogen;

R$^2$ is a bridged bicyclic aryl of formula (III):

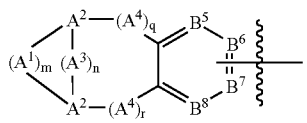

(III)

where:

m and n are independently 1 to 2;

q and r are independently 0 to 2;

each A$^1$, A$^3$ and A$^4$ is independently C(R$^8$)$_2$;

each A$^2$ is independently C(R$^8$);

B$^5$, B$^6$, B$^7$ and B$^8$ are each independently =C(R$^{13}$)—, provided that one of B$^5$, B$^6$, B$^7$ and B$^8$ is a carbon directly bonded to the nitrogen to which R$^2$ is attached; and R$^3$ is a bicyclic heteroaryl of formula (II):

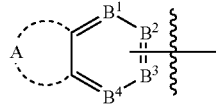

(II)

where:

A is an alkylene chain containing six carbons, where each carbon of the alkylene chain may be replaced by —N(R$^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, and one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—.

41. The compound of claim 36 wherein:

R$^1$, R$^4$ and R$^5$ are each hydrogen;

R$^2$ is a bridged bicyclic heteroaryl of formula (III):

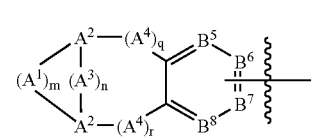

(III)

where:

m and n are independently 1 to 2;

q and r are independently 0 to 2;

each A$^1$, A$^3$ and A$^5$ is independently selected from the group consisting of C(R$^8$)$_2$, O, S(O)$_p$ (where p is 0, 1 or 2), P(O)$_p$ (where p is 0, 1 or 2) and N(R$^9$);

each A$^2$ is independently selected from the group consisting of C(R$^8$) and N;

B$^5$, B$^6$, B$^7$ and B$^8$ are each independently selected from the group consisting of =C(R$^{13}$)— and =N—, provided that at least one of A$^1$, A$^3$ and A$^4$ is independently selected from the group consisting of 0, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached; and R$^3$ is a bicyclic aryl of formula (II):

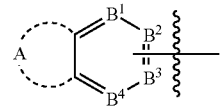

(II)

where:

A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^3$ is attached.

42. The compound of claim 41 wherein:
$R^1$, $R^4$ and $R^5$ are each hydrogen;
$R^2$ is a bridged bicyclic heteroaryl of formula (III):

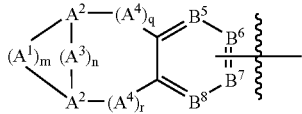

(III)

where:
  m and n are independently 1 to 2;
  q and r are independently 0 to 2;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ and N;
  $B^5$, $B^6$, $B^7$ and $B^8$ are each independently selected from the group consisting of =$C(R^{13})$— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached; and
$R^3$ is a bicyclic aryl of formula (II):

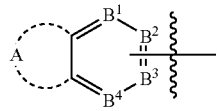

(II)

where:
  A is an alkylene chain containing six carbons, where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
  $B^1$, $B^2$, $B^3$ and $B^4$ are each independently =$C(R^{13})$—, provided that one of $B^1$, $B^2$, $B^3$ and $B^4$ is a carbon directly bonded to the nitrogen to which $R^3$ is attached.

43. The compound of claim 36 wherein:
$R^1$, $R^4$ and $R^5$ are each hydrogen;
$R^2$ is a bridged bicyclic heteroaryl of formula (III):

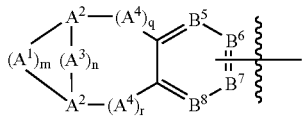

(III)

where:
  m and n are independently 1 to 2;
  q and r are independently 0 to 2;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ and N;
  $B^5$, $B^6$, $B^7$ and $B^8$ are each independently selected from the group consisting of =$C(R^{13})$— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached; and
$R^3$ is a bicyclic heteroaryl of formula (II):

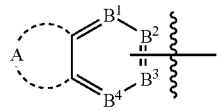

(II)

where:
  A is an alkylene chain containing six carbons, where each carbon of the alkylene chain may be replaced by —$N(R^9)$—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—O$R^9$, —$R^{10}$—O—$R^{11}$—O$R^9$, —$R^{10}$—O—$R^{11}$—O—$R^{11}$—O$R^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p$$R^9$ (where p is 0, 1 or 2), —$R^{10}$—O—$R^{11}$—N($R^6$)$R^7$, —$R^{10}$—O—$R^{11}$—C(NR$^{12}$)N(R$^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t$$R^9$ (where t is 1 or 2), —$R^{10}$—S(O)$_t$O$R^9$ (where t is 1 or 2), —$R^{10}$—S(O)$_p$$R^9$ (where p is 0, 1 or 2), and —$R^{10}$—S(O)$_t$N($R^6$)$R^7$ (where t is 1 or 2); and
  $B^1$, $B^2$, $B^3$ and $B^4$ are each independently selected from the group consisting of =$C(R^{13})$— and =N—, provided that at least one carbon in A is replaced with —$N(R^9)$—, =N—, —O—, —S(O)$_p$— (where p is 0, 1 or 2) or —P(O)$_p$— (where p is 0, 1 or 2) or one of $B^1$, $B^2$, $B^3$ and $B^4$ is =N—, one of $B^1$, $B^2$, $B^3$ and $B^4$ is a carbon directly bonded to the nitrogen to $R^3$ is attached and that only one or two of $B^1$, $B^2$, $B^3$ and $B^4$ can be =N—.

44. The compound of claim 43 wherein:
$R^1$, $R^4$ and $R^5$ are each hydrogen;
$R^2$ is a bridged bicyclic heteroaryl of formula (III):

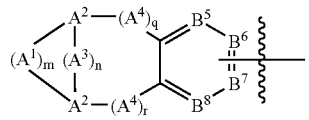

(III)

where:
  m and n are independently 1 to 2;
  q and r are independently 0 to 2;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ and N;
  $B^5$, $B^6$, $B^7$ and $B^8$ are each independently selected from the group consisting of $=C(R^{13})-$ and $=N-$, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is $=N-$ or one of $B^5$, $B^6$, $B^7$ and $B^8$ is $=N-$, and one of $B^5$, $B^6$, $B^7$ and $B^8$ is a carbon directly bonded to the nitrogen to which $R^3$ is attached; and
$R^3$ is a bicyclic heteroaryl of formula (II):

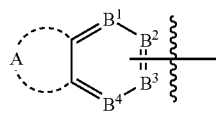
(II)

where:
  A is an alkylene chain containing six carbons, where each carbon of the alkylene chain may be replaced by $-N(R^9)-$, $=N-$, $-O-$, $-S(O)_p-$ (where p is 0, 1 or 2) or $-P(O)_p-$ (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and
  $B^1$, $B^2$, $B^3$ and $B^4$ are each independently selected from the group consisting of $=C(R^{13})-$ and $=N-$, provided that at least one carbon in A is replaced with $-N(R^9)-$, $-O-$, $-S(O)_p-$ (where p is 0, 1 or 2) or $-P(O)_p-$ (where p is 0, 1 or 2) or one of $B^1$, $B^2$, $B^3$ and $B^4$ is $=N-$, one of $B^1$, $B^2$, $B^3$ and $B^4$ is a carbon directly bonded to the nitrogen to $R^2$ is attached and that only one or two of $B^1$, $B^2$, $B^3$ and $B^4$ can be $=N-$.

45. The compound of claim 2 wherein:
  $R^1$, $R^4$ and $R^5$ are each hydrogen;
  $R^2$ is a bridged bicyclic aryl of formula (III) or a bridged bicyclic heteroaryl of formula (III):

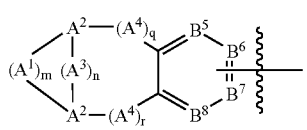
(III)

where:
  m and n are independently 1 to 2;
  q and r are independently 0 to 3;
  each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
  each $A^2$ is independently selected from the group consisting of $C(R^8)$ and N;
  $B^5$, $B^6$, $B^7$ and $B^8$ are each independently selected from the group consisting of $=C(R^{13})-$ and $=N-$, provided that one of $B^5$, $B^6$, $B^7$ and $B^8$ is a carbon directly bonded to the nitrogen to which $R^2$ is attached; and
$R^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,1'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2).

46. The compound of claim 45 wherein:
  $R^1$, $R^4$ and $R^5$ are each hydrogen;
  $R^2$ is a bridged bicyclic aryl of formula (III):

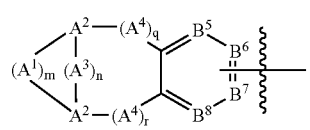
(III)

where:
    m and n are independently 1 to 2;
    q and r are independently 0 to 2;
    each $A^1$, $A^3$ and $A^4$ is independently $C(R^8)_2$;
    each $A^2$ is independently $C(R^8)$;
    $B^5$, $B^6$, $B^7$ and $B^8$ are each independently =$C(R^{13})$—, provided that one of $B^5$, $B^6$, $B^7$ and $B^8$ is a carbon directly bonded to the nitrogen to which $R^2$ is attached; and
    $R^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—$C(O)OR^9$, —$R^{10}$—O—$R^{11}$—$C(O)N(R^6)R^7$, —$R^{10}$—O—$R^{11}$—$S(O)_pR^9$ (where p is 0, 1 or 2), —$R^{10}$—O—$R^{11}$—$N(R^6)R^7$, —$R^{10}$—O—$R^{11}$—$C(NR^{12})N(R^{12})H$, —$R^{10}$—OC(O)—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2).

47. The compound of claim 46 wherein:
    $R^1$, $R^4$ and $R^5$ are each hydrogen;
    $R^2$ is a bridged bicyclic aryl of formula (III):

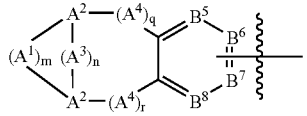

(III)

where:
    m and n are independently 1 to 2;
    q and r are independently 0 to 2;
    each $A^1$, $A^3$ and $A^4$ is independently $C(R^8)_2$;
    each $A^2$ is independently $C(R^8)$;
    $B^5$, $B^6$, $B^7$ and $B^8$ are each independently =$C(R^{13})$—, provided that one of $B^5$, $B^6$, $B^7$ and $B^8$ is a carbon directly bonded to the nitrogen to which $R^2$ is attached; and $R^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7'-dihydro-5H-benzo[2,3]azepino[4,5'-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5'-c]pyridazin-3-yl, 6,7-dihydro-5H-benzo[2,3]'thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—$OC(O)$—$R^9$, —$R^{10}$—$N(R^6)R^7$, —$R^{10}$—$C(O)R^9$, —$R^{10}$—$C(O)OR^9$, —$R^{10}$—$C(O)N(R^6)R^7$, —$R^{10}$—$N(R^6)C(O)OR^9$, —$R^{10}$—$N(R^6)C(O)R^9$, —$R^{10}$—$N(R^6)S(O)_tR^9$ (where t is 1 or 2), —$R^{10}$—$S(O)_tOR^9$ (where t is 1 or 2), —$R^{10}$—$S(O)_pR^9$ (where p is 0, 1 or 2), and —$R^{10}$—$S(O)_tN(R^6)R^7$ (where t is 1 or 2).

48. The compound of claim 47 which is 1-(6,7-dihydro-5H-benzo[6,7]cyclohepta[1,2-c]pyridazin-3-yl)-$N^3$-(7-pyrrolidin-1-yl-6,8-ethano-6,7,8,9-tetrahydro-5H-benzo[7]annulen-3-yl)-1H-1,2,4-triazole-3,5-diamine.

49. The compound of claim 45 wherein:
    $R^1$, $R^4$ and $R^5$ are each hydrogen;
    $R^2$ is a bridged bicyclic heteroaryl of formula (III):

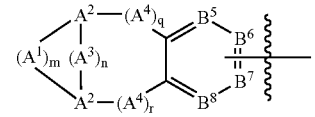

(III)

where:
    m and n are independently 1 to 2;
    q and r are independently 0 to 2;
    each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
    each $A^2$ is independently selected from the group consisting of $C(R^8)$ and N;
    $B^5$, $B^6$, $B^7$ and $B^8$ are each independently selected from the group consisting of =$C(R^{13})$— and =N—, provided that at least one of $A^1$, $A^3$ and $A^4$ is independently selected from the group consisting of O, $S(O)_p$ (where p is 0, 1 or 2), $P(O)_p$ (where p is 0, 1 or 2) and $N(R^9)$, or $A^2$ is =N— or one of $B^5$, $B^6$, $B^7$ and $B^8$ is =N—, and one of $B^5$, $B^6$, $B^7$ and $B^8$ is a carbon directly bonded to the nitrogen to which $R^3$ is attached; and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]

pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

50. The compound of claim 49 wherein:
R$^1$, R$^4$ and R$^5$ are each hydrogen;
R$^2$ is abridged bicyclic heteroaryl of formula (III):

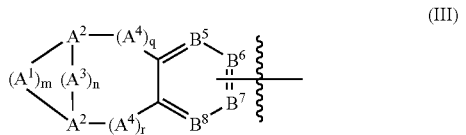

(III)

where:
m and n are independently 1 to 2;
q and r are independently 0 to 2;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that at least one of A$^1$, A$^3$ and A$^4$ is independently selected from the group consisting of O, S(O)$_p$ (where p is 0, 1 or 2), P(O)$_p$ (where p is 0, 1 or 2) and N(R$^9$), or A$^2$ is =N— or one of B$^5$, B$^6$, B$^7$ and B$^8$ is =N—, and one of B$^5$, B$^6$, B$^7$ and B$^8$ is a carbon directly bonded to the nitrogen to which R$^3$ is attached; and
R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

51. The compound of claim 1 which is a compound of formula (Ib):

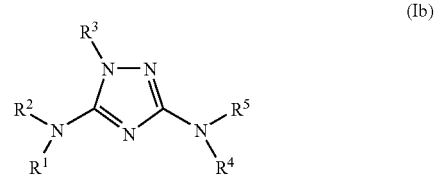

(Ib)

wherein:
R$^1$, R$^4$ and R$^5$ are independently selected from hydrogen, alkyl, aryl, aralkyl, —C(O)R$^9$ or —C(O)N(R$^6$)R$^7$;
one of R$^2$ and R$^3$ is selected from one of the following and the other is selected from the other two of the following:
a) a bicyclic aryl of formula (II) or a bicyclic heteroaryl of formula (II):

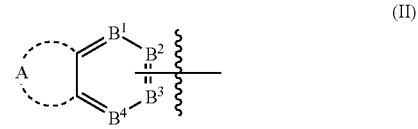

(II)

where:
A is an alkylene chain containing six to ten carbons, where one or two carbons of the alkylene chain is optionally replaced by —NR$^9$—, =N—, —O—, —S(O)$_p$ (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to which its corresponding R$^2$ or R$^3$ is attached and that only one or two of B$^1$, B$^2$, B$^3$ and B$^4$ can be =N—;

b) a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); or c) a bridged bicyclic aryl of formula (III) or a bridged bicyclic heteroaryl of formula (III):

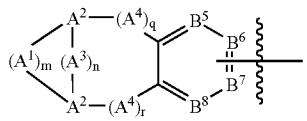

(III)

where:

m and n are independently 1 to 4;

q and r are independently 0 to 3;

each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);

each A$^2$ is independently selected from the group consisting of C(R$^8$) and N;

B$^5$, B$^6$, B$^7$ and B$^8$ are each independently selected from the group consisting of =C(R$^{13}$)— and =N—, provided that one of B$^5$, B$^6$, B$^7$ and B$^8$ is a carbon directly bonded to the nitrogen to which its corresponding R$^2$ or R$^3$ is attached;

each R$^6$ and R$^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{11}$—OR$^9$, —R$^{11}$—NO$_2$, —R$^{11}$—N(R$^9$)$_2$, —R$^{11}$—C(O)OR$^9$ and —R$^{11}$—C(O)N(R$^9$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, cyano, nitro, halo, haloalkyl, alkyl, optionally substituted cycloalkyl, optionally substituted cycloalkylalkyl, optionally substituted heteroaryl, optionally substituted heteroarylalkyl, optionally substituted heterocyclyl, optionally substituted heterocyclylalkyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), —R$^{10}$—S(O)$_t$N(R$^6$)R$^7$ (where t is 1 or 2), or two R$^8$'s on adjacent carbons can combine to form a double bond;

each R$^9$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl;

each R$^{10}$ is independently selected from the group consisting of a direct bond, an optionally substituted straight or branched alkylene chain, an optionally substituted straight or branched alkenylene chain and an optionally substituted straight or branched alkynylene chain;

each R$^{11}$ is independently selected from the group consisting of an optionally substituted straight or branched alkylene chain, an optionally substituted straight or branched alkenylene chain and an optionally substituted straight or branched alkynylene chain;

each $R^{12}$ is hydrogen, alkyl, cyano, nitro or —$OR^9$; and each $R^{13}$ is independently selected from the group consisting of hydrogen, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, optionally substituted heterocyclylalkyl, —$R^{10}$—$OR^9$, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t R^9$ (where t is 1 or 2), —$R^{10}$—S(O)$_t$O$R^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2);

as an isolated stereoisomer or a mixture thereof, or as a pharmaceutically acceptable salt thereof.

52. The compound of claim 51 wherein:

$R^1$, $R^4$ and $R^5$ are each hydrogen;

$R^2$ is a bicyclic aryl of formula (II) or a bicyclic heteroaryl of formula (II):

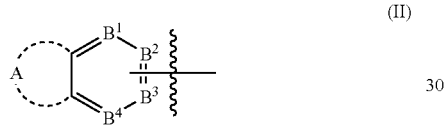

(II)

where:

A is an alkylene chain containing six to ten carbons, where one or two carbons of the alkylene chain is optionally replaced by —$NR^9$—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t R^9$ (where t is 1 or 2), —$R^{10}$—S(O)$_t$O$R^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2); and $B^1$, $B^2$, $B^3$ and $B^4$ are each independently selected from the group consisting of =C($R^{13}$)— and =N—, provided that one of $B^1$, $B^2$, $B^3$ and $B^4$ is a carbon directly bonded to the nitrogen to which its corresponding $R^2$ or $R^3$ is attached and that only one or two of $B^1$, $B^2$, $B^3$ and $B^4$ can be =N—; and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4, 5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t R^9$ (where t is 1 or 2), —$R^{10}$—S(O)$_t$O$R^9$ (where t is 1 or 2), —$R^{10}$—S(O)$_p R^9$ (where p is 0, 1 or 2), and —$R^{10}$—S(O)$_t$N($R^6$)$R^7$ (where t is 1 or 2).

53. The compound of claim 52 wherein:

$R^1$, $R^4$ and $R^5$ are each hydrogen;

$R^2$ is a bicyclic heteroaryl of formula (II):

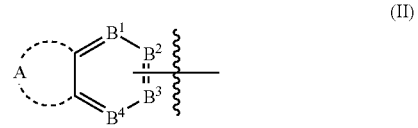

(II)

where:

A is an alkylene chain containing six carbons, where each carbon of the alkylene chain may be replaced by —N($R^9$)—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)O$R^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)O$R^9$, —$R^{10}$—C(O)N($R^6$)$R^7$, —$R^{10}$—N($R^6$)C(O)O$R^9$, —$R^{10}$—N($R^6$)C(O)$R^9$, —$R^{10}$—N($R^6$)S(O)$_t R^9$ (where t is 1 or 2), —$R^{10}$—S(O)$_t$O$R^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, one of B$^1$, B$^2$, B$^3$ and B$^4$ is a carbon directly bonded to the nitrogen to which R$^2$ is attached and that only one or two of B$^1$, B$^2$, B$^3$ and B$^4$ can be =N—; and R$^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

54. The compound of claim 53 wherein:
R$^1$, R$^4$ and R$^5$ are each hydrogen;
R$^2$ is a bicyclic heteroaryl of formula (II):

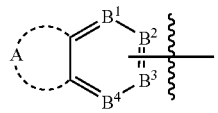

(II)

where:
A is an alkylene chain containing six carbons, where each carbon of the alkylene chain may be replaced by —N(R$^9$)—, =N—, —O—, —S(O)$_p$ (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— or =N—, provided that at least one carbon in A is replaced with —N(R$^9$)—, =N—, —O—, —S(O)$_p$— (where p is 0, 1 or 2) or —P(O)$_p$— (where p is 0, 1 or 2) or one of B$^1$, B$^2$, B$^3$ and B$^4$ is =N—, one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

55. The compound of claim 54 wherein:
R$^1$, R$^4$ and R$^5$ are each hydrogen;
R$^2$ is a bicyclic heteroaryl of formula (II):

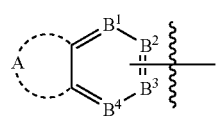

(II)

where:
A is an alkylene chain containing six carbons, where at least one carbon is replaced by —N(R$^9$)— and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently =C(R$^{13}$)—, provided that one of B$^1$, B$^2$, B$^3$ and B$^4$ is a carbon directly bonded to the nitrogen to which R$^2$ is attached; and R$^3$ is selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —R$^{10}$—OR$^9$, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2).

56. The compound of claim 55 which is 1-(6,7-dihydro-5H-benzo[6,7]cyclohepta[1,2-c]pyridazin-3-yl)-N$^5$-(1(2H)-oxo-3,4,5,6-tetrahydrobenzo[c]azocin-9-yl)-1H-1,2,4-triazole-3,5-diamine.

57. The compound of claim 51 wherein:
R$^1$, R$^4$ and R$^5$ are each hydrogen;
R$^2$ is a bicyclic aryl of formula (II) or a bicyclic heteroaryl of formula (II):

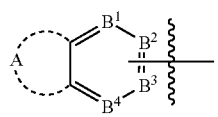

(II)

where:
A is an alkylene chain containing six to ten carbons, where one or two carbons of the alkylene or alkenylene chain is optionally replaced by —NR$^9$—, =N—, —O—, —S(O)$_p$— (where p is 0, 1 or 2) or —P(O)$_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—R$^6$, —R$^{10}$—OR$^9$, —R$^{10}$—O—R$^{11}$—OR$^9$, —R$^{10}$—O—R$^{11}$—O—R$^{11}$—OR$^9$, —R$^{10}$—O—R$^{11}$—CN, —R$^{10}$—O—R$^{11}$—C(O)OR$^9$, —R$^{10}$—O—R$^{11}$—C(O)N(R$^6$)R$^7$, —R$^{10}$—O—R$^{11}$—S(O)$_p$R$^9$ (where p is 0, 1 or 2), —R$^{10}$—O—R$^{11}$—N(R$^6$)R$^7$, —R$^{10}$—O—R$^{11}$—C(NR$^{12}$)N(R$^{12}$)H, —R$^{10}$—OC(O)—R$^9$, —R$^{10}$—N(R$^6$)R$^7$, —R$^{10}$—C(O)R$^9$, —R$^{10}$—C(O)OR$^9$, —R$^{10}$—C(O)N(R$^6$)R$^7$, —R$^{10}$—N(R$^6$)C(O)OR$^9$, —R$^{10}$—N(R$^6$)C(O)R$^9$, —R$^{10}$—N(R$^6$)S(O)$_t$R$^9$ (where t is 1 or 2), —R$^{10}$—S(O)$_t$OR$^9$ (where t is 1 or 2), —R$^{10}$—S(O)$_p$R$^9$ (where p is 0, 1 or 2), and —R$^{10}$—S(O)$_t$N(R$^6$)R$^7$ (where t is 1 or 2); and B$^1$, B$^2$, B$^3$ and B$^4$ are each independently selected from the group consisting of =C(R$^{13}$)— and =N—, provided that one of B$^1$, B$^2$, B$^3$ and B$^4$ is a carbon directly bonded to the nitrogen to R$^2$ is attached and that only one or two of B$^1$, B$^2$, B$^3$ and B$^4$ can be =N—; and R$^3$ is a bridged bicyclic aryl of formula (III) or a bridged bicyclic heteroaryl of formula (III):

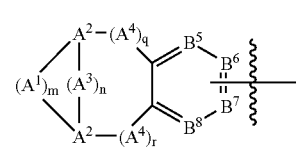

(III)

where:
m and n are independently 1 to 2;
q and r are independently 0 to 3;
each A$^1$, A$^3$ and A$^4$ is independently selected from the group consisting of C(R$^8$)$_2$, O, S(O)$_p$ (where p is 0, 1 or 2), P(O)$_p$ (where p is 0, 1 or 2) and N(R$^9$);
each A$^2$ is independently selected from the group consisting of C(R$^8$) and N;
B$^5$, B$^6$, B$^7$ and B$^8$ are each independently selected from the group consisting of =C(R$^{13}$)— and =N—, provided that one of B$^5$, B$^6$, B$^7$ and B$^8$ is a carbon directly bonded to the nitrogen to which R$^3$ is attached.

58. The compound of claim 51 wherein:
R$^1$, R$^4$ and R$^5$ are each hydrogen;
R$^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $R^3$ is a bicyclic aryl of formula (II) or a bicyclic heteroaryl of formula (II):

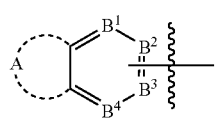

(II)

where:

A is an alkylene chain containing six to ten carbons, where each carbon of the alkylene chain may be replaced by $-N(R^9)-$, $=N-$, $-O-$, $-S(O)_p-$ (where p is 0, 1 or 2) or $-P(O)_p-$ (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, $=N-O-R^6$, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $B^1$, $B^2$, $B^3$ and $B^4$ are each independently selected from the group consisting of $=C(R^{13})-$ and $=N-$, provided that one of $B^1$, $B^2$, $B^3$ and $B^4$ is a carbon directly bonded to the nitrogen to which $R^3$ is attached and that only one or two of $B^1$, $B^2$, $B^3$ and $B^4$ can be $=N-$.

59. The compound of claim 51 wherein:

$R^1$, $R^4$ and $R^5$ are each hydrogen;

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-c]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, $-R^{10}-OR^9$, $-R^{10}-O-R^{11}-OR^9$, $-R^{10}-O-R^{11}-O-R^{11}-OR^9$, $-R^{10}-O-R^{11}-CN$, $-R^{10}-O-R^{11}-C(O)OR^9$, $-R^{10}-O-R^{11}-C(O)N(R^6)R^7$, $-R^{10}-O-R^{11}-S(O)_pR^9$ (where p is 0, 1 or 2), $-R^{10}-O-R^{11}-N(R^6)R^7$, $-R^{10}-O-R^{11}-C(NR^{12})N(R^{12})H$, $-R^{10}-OC(O)-R^9$, $-R^{10}-N(R^6)R^7$, $-R^{10}-C(O)R^9$, $-R^{10}-C(O)OR^9$, $-R^{10}-C(O)N(R^6)R^7$, $-R^{10}-N(R^6)C(O)OR^9$, $-R^{10}-N(R^6)C(O)R^9$, $-R^{10}-N(R^6)S(O)_tR^9$ (where t is 1 or 2), $-R^{10}-S(O)_tOR^9$ (where t is 1 or 2), $-R^{10}-S(O)_pR^9$ (where p is 0, 1 or 2), and $-R^{10}-S(O)_tN(R^6)R^7$ (where t is 1 or 2); and $R^3$ is a bridged bicyclic aryl of formula (III) or a bridged bicyclic heteroaryl of formula (III):

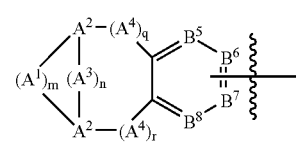

(III)

where:

m and n are independently 1 to 2;

q and r are independently 0 to 3;

each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;

each $A^2$ is independently selected from the group consisting of $C(R^8)$ or N;

$B^5$, $B^6$, $B^7$ and $B^8$ are each independently $=C(R^{13})-$ or $=N-$, provided that one of $B^5$, $B^6$, $B^7$ and $B^8$ is a carbon directly bonded to the nitrogen to which $R^3$ is attached.

60. The compound of claim 51 wherein:

$R^1$, $R^4$ and $R^5$ are each hydrogen;

$R^2$ is a bridged bicyclic aryl of formula (III) or a bridged bicyclic heteroaryl of formula (III):

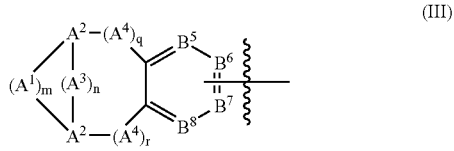

(III)

where:
m and n are independently 1 to 2;
q and r are independently 0 to 3;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of $C(R^8)$ and N;
$B^5$, $B^6$, $B^7$ and $B^8$ are each independently selected from the group consisting of =$C(R^{13})$— and =N—, provided that one of $B^5$, $B^6$, $B^7$ and $B^8$ is a carbon directly bonded to the nitrogen to which $R^2$ is attached; and $R^3$ is a bicyclic aryl of formula (II) or a bicyclic heteroaryl of formula (II):

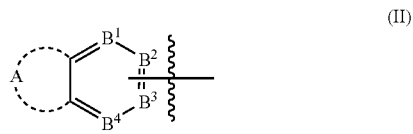

(II)

where:
A is an alkylene chain containing six to ten carbons, where each carbon of the alkylene chain may be replaced by —$N(R^9)$—, =N—, —O—, —$S(O)_p$— (where p is 0, 1 or 2) or —$P(O)_p$— (where p is 0, 1 or 2) and where each carbon in the alkylene chain is independently optionally substituted by one or two substituents selected from the group consisting of oxo, thioxo, cyano, nitro, halo, haloalkyl, alkyl, cycloalkyl, cycloalkylalkyl, optionally substituted heteroaryl, optionally substituted heteroarylalkyl, optionally substituted heterocyclyl, optionally substituted heterocyclylalkyl, =N—O—$R^6$, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t N(R^6)R^7$ (where t is 1 or 2); and $B^1$, $B^2$, $B^3$ and $B^4$ are each independently selected from the group consisting of =$C(R^{13})$— and =N—, provided that one of $B^1$, $B^2$, $B^3$ and $B^4$ is a carbon directly bonded to the nitrogen to which $R^3$ is attached and that only one or two of $B^1$, $B^2$, $B^3$ and $B^4$ can be =N—.

61. The compound of claim 51 wherein:

$R^1$, $R^4$ and $R^5$ are each hydrogen;

$R^2$ is a bridged bicyclic aryl of formula (III) or a bridged bicyclic heteroaryl of formula (III):

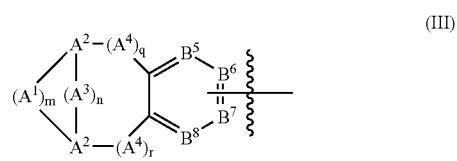

(III)

where:
m and n are independently 1 to 2;
q and r are independently 0 to 3;
each $A^1$, $A^3$ and $A^4$ is independently selected from the group consisting of $C(R^8)_2$, O, $S(O)_p$ (where p is 0, 1 or 2), $P(O)_p$ (where p is 0, 1 or 2) and $N(R^9)$;
each $A^2$ is independently selected from the group consisting of $C(R^8)$ and N;
$B^5$, $B^6$, $B^7$ and $B^8$ are each independently selected from the group consisting of =$C(R^{13})$— and =N—, provided that one of $B^5$, $B^6$, $B^7$ and $B^8$ is a carbon directly bonded to the nitrogen to which $R^2$ is attached; and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-benzo[6,7]cyclohepta[1,2-d]pyrimidin-4-yl, 6,7-dihydro-5H-benzo[6,7]cyclohepta[1,2-d]pyrimidin-2-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, 6,7-dihydro-5H-benzo[2,3]thiepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,7,8,9-tetrahydrospiro[cyclohepta[b]pyridine-6,2'-[1,3]dioxolane]-3-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl, and 6,7-dihydro-5H-benzo[6,7]cyclohepta[1,2-b]pyridin-2-yl, where each polycyclic heteroaryl is optionally substituted by one or more substituents selected from the group consisting of oxo, thioxo, cyano, nitro, halo, haloalkyl, alkyl, cycloalkyl, cycloalkylalkyl, optionally substituted aryl, optionally substituted aralkyl, optionally substituted heteroaryl, optionally substituted heterocyclyl, —$R^{10}$—$OR^9$, —$R^{10}$—O—$R^{11}$—$OR^9$, —$R^{10}$—O—$R^{11}$—O—$R^{11}$—$OR^9$, —$R^{10}$—O—$R^{11}$—CN, —$R^{10}$—O—$R^{11}$—C(O)$OR^9$, —$R^{10}$—O—$R^{11}$—C(O)N($R^6$)$R^7$, —$R^{10}$—O—$R^{11}$—S(O)$_p R^9$ (where p is 0, 1 or 2), —$R^{10}$—O—$R^{11}$—N($R^6$)$R^7$, —$R^{10}$—O—$R^{11}$—C(N$R^{12}$)N($R^{12}$)H, —$R^{10}$—OC(O)—$R^9$, —$R^{10}$—N($R^6$)$R^7$, —$R^{10}$—C(O)$R^9$, —$R^{10}$—C(O)$OR^9$, —$R^{10}$—C(O)N($R^6$)$R^7$, —$R^{10}$—N($R^6$)C(O)$OR^9$, —$R^{10}$—N($R^6$)C(O)$R^9$, —$R^{10}$—N($R^6$)S(O)$_t R^9$ (where t is 1 or 2), —$R^{10}$—S(O)$_t OR^9$ (where t is 1 or 2), —$R^{10}$—S(O)$_p R^9$ (where p is 0, 1 or 2), and —$R^{10}$—S(O)$_t N(R^6)R^7$ (where t is 1 or 2).

62. A pharmaceutical composition comprising a pharmaceutically acceptable excipient and a therapeutically effective amount of a compound of claim 1; as an isolated stereoisomer or a mixture thereof, or as a pharmaceutically acceptable salt thereof.

63. A method of inhibiting Axl catalytic activity in a mammal, wherein the method comprises administering to the mammal a compound of claim 1; as an isolated stereoisomer or a mixture thereof, or as a pharmaceutically acceptable salt thereof.

* * * * *

UNITED STATES PATENT AND TRADEMARK OFFICE
CERTIFICATE OF CORRECTION

PATENT NO.        : 7,935,693 B2
APPLICATION NO.   : 11/967163
DATED             : May 3, 2011
INVENTOR(S)       : Rajinder Singh et al.

It is certified that error appears in the above-identified patent and that said Letters Patent is hereby corrected as shown below:

Column 113, Lines 19-20:
"$R^{11}$-C(O)O$R^9$ and –$R^{11}$-C(O)N($R^9$)$_2$," should read, -- -$R^{11}$-C(O)O$R^9$ and –$R^{11}$-C(O)N($R^9$)$_2$,--.

Column 116, Lines 39-40:
"-$R^{10}$-S(O)$_p R^9$ (where p is 0, 1 or 2)," should read, -- -$R^{10}$-S(O)$_p R^9$ (where p is 0, 1 or 2), and--.

Column 119, Line 67:
"-$R^{10}$-N($R^6$)C(O)$_R^9$," should read, -- -$R^{10}$-N($R^6$)C(O)$R^9$,--.

Column 121, Lines 31-32:
"5,7,8,9-tetrahydrospiro[cyclohepta[b]pyridine-6, T-[1,3]dioxolane]-3-yl," should read, --5,7,8,9-tetrahydrospiro[cyclohepta[b]pyridine-6,2'-[1,3]dioxolane]-3-yl,--.

Column 125, Line 41:
"-S(O)$_p$- (where p is 0, 1 or 2) or –P(O)- (where" should read, -- -S(O)$_p$- (where p is 0, 1 or 2) or –P(O)$_p$- (where--.

Column 128, Line 62:
"selected from the group consisting of 0, S(O)$_p$" should read, --selected from the group consisting of O, S(O)$_p$--.

Column 130, Line 31:
"-N($R^9$)-, -O-, -S(O)$_p$- (where p is 0, 1 or 2)" should read, -- -N($R^9$)-, =N-, -O-, -S(O)$_p$- (where p is 0, 1 or 2)--.

Column 131, Line 5:
"1 or 2) or –P(O)- (where p is 0, 1 or 2) and where" should read, --1 or 2) or –P(O)$_p$- (where p is 0, 1 or 2) and where--.

Signed and Sealed this
Fourteenth Day of August, 2012

David J. Kappos
*Director of the United States Patent and Trademark Office*

Column 131, Line 24:
"-N(R$^9$)-, -O-, -S(O)$_p$- (where p is 0, 1 or 2)" should read, -- -N(R$^9$)-, =N-, -O-, -S(O)$_p$- (where p is 0, 1 or 2)--.

Column 142, Lines 20-21:
"(Z)-dibenzo[V][1,4]thiazepin-11-yl," should read, --(Z)-dibenzo[*b,f*][1,4]thiazepin-11-yl,--.

Column 144, Line 44:
"selected from the group consisting of 0, S(O)$_p$" should read, --selected from the group consisting of O, S(O)$_p$--.

Column 144, Lines 53-54:
"6,7-dihydro-5H-benzo[6,7]cycloheptal[1,2-a]pyrimidin-4-yl," should read, --6,7-dihydro-5H-benzo[6,7]cycloheptal[1,2-d]pyrimidin-4-yl,--.

Column 145, Line 36:
"selected from the group consisting of 0, S(O)$_p$" should read, --selected from the group consisting of O, S(O)$_p$--.

Column 149, Lines 4-5:
"one of B$^1$, B$^2$, B$^3$ and B$^4$ is a carbon directly bonded to the =N-." should read, --one of B$^1$, B$^2$, B$^3$ and B$^4$ is a carbon directly bonded to the nitrogen to which R$^3$ is attached and that only one or two of B$^1$, B$^2$, B$^3$ and B$^4$ can be =N-.--.

Column 150, Line 25:
"selected from the group consisting of 0, S(O)$_p$" should read, --selected from the group consisting of O, S(O)$_p$--.

Column 151, Line 23:
"selected from the group consisting of 0, S(O)$_p$" should read, --selected from the group consisting of O, S(O)$_p$--.

Column 152, Line 12:
"selected from the group consisting of 0, S(O)$_p$" should read, --selected from the group consisting of O, S(O)$_p$--.

Column 153, Line 12:
"selected from the group consisting of 0, S(O)$_p$" should read, --selected from the group consisting of O, S(O)$_p$--.

Column 153, Line 49:
"-N(R$^9$)-, -O-, -S(O)$_p$- (where p is 0, 1 or 2)" should read, -- -N(R$^9$)-, =N-, -O-, -S(O)$_p$- (where p is 0, 1 or 2)--.

Column 154, Lines 30-32:
"5,6,8,9-tetrahydrospiro[cycloheptal[b]pyridine-7,1'-[1,3]dioxolane]-3-yl," should read, --5,6,8,9-tetrahydrospiro[cycloheptal[b]pyridine-7,2'-[1,3]dioxolane]-3-yl,--.

Column 156, Lines 5-6:
"6,7'-dihydro-5H-benzo[2,3]azepino[4,5'-c]pyridazin-3-yl," should read, --6,7'-dihydro-5H-benzo[2,3]azepino[4,5-c]pyridazin-3-yl,--.

Column 156, Lines 8-9:
"6,7-dihydro-5H-benzo[2,3]oxepino[4,5'-c]pyridazin-3-yl," should read, --6,7-dihydro-5H-benzo[2,3]oxepino[4,5-c]pyridazin-3-yl,--.

Column 156, Lines 9-10:
"6,7-dihydro-5H-benzo[2,3]'thiepino[4,5-c]pyridazin-3-yl," should read, --6,7-dihydro-5H-benzo[2,3]thiepino[4,5-c]pyridazin-3-yl,--.

Column 156, Line 57:
"selected from the group consisting of 0, $S(O)_p$" should read, --selected from the group consisting of O, $S(O)_p$--.

Column 157, Line 56:
"selected from the group consisting of 0, $S(O)_p$" should read, --selected from the group consisting of O, $S(O)_p$--.

Column 160, Lines 22-23:
"-$R^{11}$-$OR^9$, -$R^{11}$-$NO_2$, -$R^{11}$-$N(R^9)_2$, -$R^{11}$-C(O)$OR^9$ and –$R^{11}$-C(O)N($R^9$)$_2$ or" should read, -- -$R^{11}$-$OR^9$, -$R^{11}$-CN, -$R^{11}$-$NO_2$, -$R^{11}$-$N(R^9)_2$, -$R^{11}$-C(O)$OR^9$ and –$R^{11}$-C(O)N($R^9$)$_2$ or--.

Column 161, Line 36:
"optionally replaced by –$NR^9$-, -O-, -$S(O)_p$-" should read, --optionally replaced by –$NR^9$-, =N-, -O-, -$S(O)_p$- --.

Column 168, Lines 8-9:
"6,7-dihydro-5H-benzo[6,7]cycloheptal[1,2-c]pyrimidin-2-yl," should read, --6,7-dihydro-5H-benzo[6,7]cycloheptal[1,2-*d*]pyrimidin-2-yl,--.